(12) United States Patent
Ungashe et al.

(10) Patent No.: US 8,211,896 B2
(45) Date of Patent: Jul. 3, 2012

(54) ARYL SULFONAMIDES

(75) Inventors: Solomon Ungashe, Fremont, CA (US); Zheng Wei, Redwood City, CA (US); J. J. Wright, Redwood City, CA (US); Andrew Pennell, San Fransisco, CA (US)

(73) Assignee: Chemocentryx, Inc., Mountain View, CA (US)

( * ) Notice: Subject to any disclaimer, the term of this patent is extended or adjusted under 35 U.S.C. 154(b) by 0 days.

(21) Appl. No.: 12/896,114

(22) Filed: Oct. 1, 2010

(65) Prior Publication Data

US 2011/0021523 A1 Jan. 27, 2011

Related U.S. Application Data

(63) Continuation of application No. 12/498,633, filed on Jul. 7, 2009, now abandoned, which is a continuation of application No. 12/251,829, filed on Oct. 15, 2008, now abandoned, which is a continuation of application No. 11/046,565, filed on Jan. 27, 2005, now Pat. No. 7,582,661, which is a continuation of application No. 10/716,170, filed on Nov. 17, 2003, now Pat. No. 6,939,885.

(60) Provisional application No. 60/427,670, filed on Nov. 18, 2002.

(51) Int. Cl.
| | |
|---|---|
| A61K 31/4427 | (2006.01) |
| A61K 31/4523 | (2006.01) |
| A61K 31/501 | (2006.01) |
| A61K 31/506 | (2006.01) |
| C07D 213/34 | (2006.01) |
| C07D 239/26 | (2006.01) |

(52) U.S. Cl. ........ 514/256; 544/335; 544/406; 546/314; 546/347; 514/252.1; 514/354; 514/358

(58) Field of Classification Search .................. 544/335, 544/406; 546/314, 347; 514/252.1, 256, 514/354, 358

See application file for complete search history.

(56) References Cited

U.S. PATENT DOCUMENTS

| | | | |
|---|---|---|---|
| 2,997,368 | A | 8/1961 | Barent et al. |
| 3,121,103 | A | 2/1964 | Keller et al. |
| 3,344,183 | A | 9/1967 | Reeder et al. |
| 3,442,946 | A | 5/1969 | Keller et al. |
| 3,534,062 | A | 10/1970 | Wright et al. |
| 3,551,427 | A | 12/1970 | Ott et al. |

(Continued)

FOREIGN PATENT DOCUMENTS

CH  491126  7/1970

(Continued)

OTHER PUBLICATIONS

Science IP Search Report (Mar. 1, 2005).

(Continued)

*Primary Examiner* — Kamal Saeed
*Assistant Examiner* — Janet L Coppins
(74) *Attorney, Agent, or Firm* — Oblon, Spivak, McClelland, Maier & Neustadt, L.L.P.

(57) ABSTRACT

Compounds are provided that act as potent antagonists of the CCR9 receptor, and which have been further confirmed in animal testing for inflammation, one of the hallmark disease states for CCR9. The compounds are generally aryl sulfonamide derivatives and are useful in pharmaceutical compositions, methods for the treatment of CCR9-mediated diseases, and as controls in assays for the identification of CCR9 antagonists.

78 Claims, 1 Drawing Sheet

U.S. PATENT DOCUMENTS

| | | | |
|---|---|---|---|
| 3,842,082 A | 10/1974 | Hunziker | |
| 4,166,452 A | 9/1979 | Generales, Jr. | |
| 4,256,108 A | 3/1981 | Theeuwes | |
| 4,265,874 A | 5/1981 | Bonsen et al. | |
| 4,372,975 A | 2/1983 | Mouzin et al. | |
| 4,954,518 A | 9/1990 | Takano et al. | |
| 4,992,091 A | 2/1991 | Vinogradoff et al. | |
| 4,997,940 A | 3/1991 | Vinogradoff et al. | |
| 5,021,591 A | 6/1991 | Vinogradoff et al. | |
| 5,071,468 A | 12/1991 | Astles et al. | |
| 5,093,364 A | 3/1992 | Richards et al. | |
| 5,155,121 A | 10/1992 | Niewohner et al. | |
| 5,163,995 A | 11/1992 | Van Heertum et al. | |
| 5,185,348 A | 2/1993 | Niewohner et al. | |
| 5,217,521 A | 6/1993 | Durr | |
| 5,338,755 A | 8/1994 | Wagnon et al. | |
| 5,481,005 A | 1/1996 | Wagnon et al. | |
| 5,541,186 A | 7/1996 | Breu et al. | |
| 5,571,775 A | 11/1996 | Van Heertum | |
| 5,589,478 A | 12/1996 | Yamada et al. | |
| 5,780,488 A | 7/1998 | Bergman et al. | |
| 5,973,148 A | 10/1999 | Ringer et al. | |
| 6,136,971 A | 10/2000 | Harrington et al. | |
| 6,200,995 B1 | 3/2001 | De la Brouse-Elwood | |
| 6,297,195 B1 | 10/2001 | Gesing et al. | |
| 6,297,239 B1 | 10/2001 | deSolms et al. | |
| 6,316,450 B1 | 11/2001 | Bromidge et al. | |
| 6,403,607 B1 | 6/2002 | Hidaka et al. | |
| 6,432,624 B1 | 8/2002 | Kikuchi et al. | |
| 6,653,332 B2 | 11/2003 | Jaen et al. | |
| 6,770,648 B2 | 8/2004 | McGee et al. | |
| 6,939,885 B2 | 9/2005 | Ungashe et al. | |
| 7,227,035 B2 | 6/2007 | Ungashe et al. | |
| 7,238,717 B2 | 7/2007 | Fleming et al. | |
| 7,282,502 B2 * | 10/2007 | Fleming et al. | 514/252.1 |
| 7,335,653 B2 | 2/2008 | Ungashe et al. | |
| 7,420,055 B2 | 9/2008 | Ungashe et al. | |
| 7,582,661 B2 | 9/2009 | Ugashe et al. | |
| 2002/0009116 A1 | 1/2002 | Kobayashi et al. | |
| 2002/0012680 A1 | 1/2002 | Patel | |
| 2002/0013314 A1 | 1/2002 | Zhu et al. | |
| 2002/0037905 A1 | 3/2002 | Dahl | |
| 2002/0037928 A1 | 3/2002 | Jaen et al. | |
| 2002/0052363 A1 | 5/2002 | Dinsmore et al. | |
| 2002/0065303 A1 | 5/2002 | Zhu et al. | |
| 2002/0072530 A1 | 6/2002 | Zhu et al. | |
| 2002/0103202 A1 | 8/2002 | Pinto | |
| 2003/0060460 A1 | 3/2003 | Ohuchida et al. | |
| 2003/0139390 A1 | 7/2003 | McGee et al. | |
| 2004/0167113 A1 | 8/2004 | Ugashe et al. | |
| 2005/0137193 A1 | 6/2005 | Ungashe et al. | |
| 2006/0111351 A1 | 5/2006 | Ungashe et al. | |
| 2007/0021466 A1 | 1/2007 | Ungashe et al. | |
| 2008/0293717 A1 | 11/2008 | Ugashe et al. | |
| 2009/0118307 A1 | 5/2009 | Ugashe et al. | |
| 2009/0163498 A1 | 6/2009 | Ungashe et al. | |
| 2009/0270616 A1 | 10/2009 | Ugashe et al. | |
| 2010/0227902 A1 | 9/2010 | Ungashe et al. | |

FOREIGN PATENT DOCUMENTS

| | | |
|---|---|---|
| CH | 561703 | 5/1973 |
| CH | 585222 | 2/1977 |
| DE | 2022187 | 11/1970 |
| DE | 2257443 | 5/1973 |
| DE | 3544409 A1 | 10/1986 |
| DE | 3825041 A1 | 2/1990 |
| EP | 0 015 214 B1 | 9/1980 |
| EP | 0 526 348 A1 | 2/1993 |
| EP | 556673 B1 | 2/1993 |
| EP | 0 613 894 A1 | 9/1994 |
| GB | 884847 | 12/1961 |
| GB | 1332697 | 10/1973 |
| JP | 61113060 | 5/1986 |
| JP | 04364168 | 12/1992 |
| JP | 06145145 | 5/1994 |
| JP | 2001089412 | 4/2001 |
| WO | WO 93/03013 | 2/1993 |
| WO | WO 94/20142 | 9/1994 |
| WO | WO 95/33462 | 12/1995 |
| WO | WO 96/08483 | 3/1996 |
| WO | WO 98/11218 | 3/1998 |
| WO | WO 98/28270 | 7/1998 |
| WO | WO 98/50029 | 11/1998 |
| WO | 99/17777 | 4/1999 |
| WO | WO 99/38845 | * 8/1999 |
| WO | WO99/38845 | 8/1999 |
| WO | WO 99/42465 | 8/1999 |
| WO | WO 99/55663 | 11/1999 |
| WO | WO 00/05214 | 2/2000 |
| WO | WO 00/62778 | 10/2000 |
| WO | WO 01/00579 | 1/2001 |
| WO | WO 01/00579 A1 | 1/2001 |
| WO | WO 01/09097 | 2/2001 |
| WO | WO 01/17971 | 3/2001 |
| WO | WO 01/19788 | 3/2001 |
| WO | WO 01/19798 | 3/2001 |
| WO | WO 01/32646 | 5/2001 |
| WO | WO 01/56607 | 8/2001 |
| WO | WO 01/56989 | 8/2001 |
| WO | WO 01/57003 | 8/2001 |
| WO | WO 01/57020 | 8/2001 |
| WO | WO 01/60319 | 8/2001 |
| WO | WO 01/60369 | 8/2001 |
| WO | WO 02/00633 | 1/2002 |
| WO | WO 02/18326 A1 | 3/2002 |
| WO | WO 02/30358 | 4/2002 |
| WO | WO 02/054867 | 7/2002 |
| WO | WO 02/055501 | 7/2002 |
| WO | WO 02/059080 | 8/2002 |
| WO | WO 03/099773 | 12/2003 |
| WO | WO 2004/046092 | 6/2004 |
| WO | WO 2004/058164 | 7/2004 |
| WO | WO 2004/099127 | 11/2004 |
| WO | WO 2005/004810 A2 | 1/2005 |
| WO | WO 2006/076644 | 7/2006 |
| WO | WO 2007/014054 | 2/2007 |

OTHER PUBLICATIONS

Search Report (Sep. 3, 2002).
Berman et al., Immunol. Invest., 17, pp. 625-677, 1988.
Campbell, et al., J. Exp., Med., 195(1), pp. 135-141 ,. 2002.
Dahinden, et al., J. Exp. Med., 179, pp. 751-756, 1994.
Dannhardt,-et. al., 37 Eur. J. Med.Chem., pp. 147-1 61, 2002.
Davidson et al., J Exp Med.; 184, pp. 241-251, 1996.
Kavanaugh et al., J. Immunol., 146, pp. 4149-4156, 1991.
Kontoyiannis et al., Immunity, 10, pp. 387-398, 1999.
Kosiewicz et al., J Clin Invest., 107(6), pp. 695-702, 2001.
Kunkel, et al., J. Exp. Med. 192(5), pp. 761-767, 2000.
Lothrop et at., J.Amer.Chem.Coc., CODEN:JACSAT, 63, pp. 2564-2567, 1941.
Murphy, Rev. Immun., 12, pp. 593-633, .1 994.
Neote, et al., Cell, 72, pp. 415-425, 1993.
Panwala, et al., J Immunol., 161, pp. 5733-44, 1998.
Papadakis, et al., J. Immunol., 165, pp. 5069-5076, 2000.
Powrie et al., Int Immunol., 5(11), pp. 1461-71, 1993.
Qiuping Z et al., Cancer Res., 63, pp. 6469-77, 2003.
Schaarschmidt; Herzenberg, ChemBer., CODEN:CHBEAM, 53, pp. 1388-1 399, 1920.
Schall, Cytokine, 3, pp. 165-183, 1991.
Schall, et al., Curr. Opin. Immunol., 6, pp. 865-873, 1994.
SciFinder Search Results (Feb. 19, 2004).
SciFinder Search Results (Feb. 20, 2004).
Silvestri et al., Medicinal Chemistry Research, 11 (4), pp. 195-21 8, 2002.
Street et.al., Journal of Chemical Research, Synopses, (5), pp. 154-55, 1987.
Targan et al., N. Engl J Med., 337(15), pp. 1029-35, 1997.
Uehara, et al., J. Immunol, 168(6), pp. 281 1-2819, 2002.
Ullmann; Bleier, Chem.Ber., CODEN:CHBEAM, 35, pp. 4273-4280, 1902.
Van Riper, et al., J. Exp. Med., 177, pp. 851-856, 1993.
Wurbel, et al., Blood, 98(9), pp. 2626-2632, 2001.

Youn BS, et al., Apoptosis, 7, pp. 271-276, 2002.
Zaballos, et al., J. Immunol., 162, pp. 5671-5675, 1999.
CAS Registry Record for CAS registry # 748147-95-7: Chemical Library; Supplier: Enamine; Sep. 20, 2004.
CAS Registry Record for CAS registry # 748147-95-7: Chemical Library; Enamine Screening Library; Jan. 1, 2009: Accession No. (AN): 2067790949 CHEMCATS.
CAS Registry Record for CAS registry # 748147-95-7: Chemical Library; Ambinter Stock Screening Collection; Feb. 20, 2009: Accession No. (AN): 2061972852 CHEMCATS.
CAS Registry Record for CAS registry # 748147-95-7: Chemical Library; Ryan Scientific Screening Library: Jan. 25, 2008: Accession No. (AN): 2043833780 CHEMCATS.
CAS Registry Record for CAS registry # 748147-95-7: Chemical Library; Aurora Screening Library; Feb. 9, 2009: Accession No. (AN): 2025798301 CHEMCATS.
Goerlitzer "Archiv der Pharmazie" Weinheim, Germany; pp. 254-261 1979.
SciFinder-Search Results, dated Jan. 24, 2006 (ethers).
Science IP Search Results, Mar. 29, 2006.
Science IP Search Results, Jun. 6, 2006.
SciFinder-Search Result-dated Aug. 27, 2007-212 pages.
Aug. 2007 Search results for Compounds Commercially available on May 2001 (MDL database SCD 200, released 4Q2000)—carbonyl linker—62 pages.
Aug. 2007 Search results for Compounds Commercially available on May 2001 (MDL database SCD 200, released 4Q2000)—sulfur linker—18 pages.
Aug. 2007 Search results for Compounds Commercially available on May 2001—61 pages.
Aug. 2007 SciFinder Search results—Search Result—Scientific Literature-76 pages. (includes on foreign publication).
Aug. 2007 SciFinder Search results-Search Result—dated Aug 27, 2007-51 pages.
Kajfez et al "Acta Pharmaceutica Jugoslavica" pp. 199-207, 1976.
Hunziker et al "European Journal of Medicinal Chemistry" pp. 391-398, 1981.
Haider, "Heterocycles" p. 2651, 1985.
Street, "J. Chem Res. 5" pp. 1247-1285, 1987.
Arcus et al "Journal of the Chemical Society, Abstracts" pp. 2098-2102, 1960.
Coombs et al "Journal of Medicinal Chemistry" pp. 1237-1245, 1973.
SciFinder-Search Result—dated Jan. 24, 2006 (ethers).
SciFinder—Search Result—dated Jan. 24, 2006 (ethers).
U.S. Appl. No. 12/551,640, filed Sep. 1, 2009, Ungashe, et al.

* cited by examiner

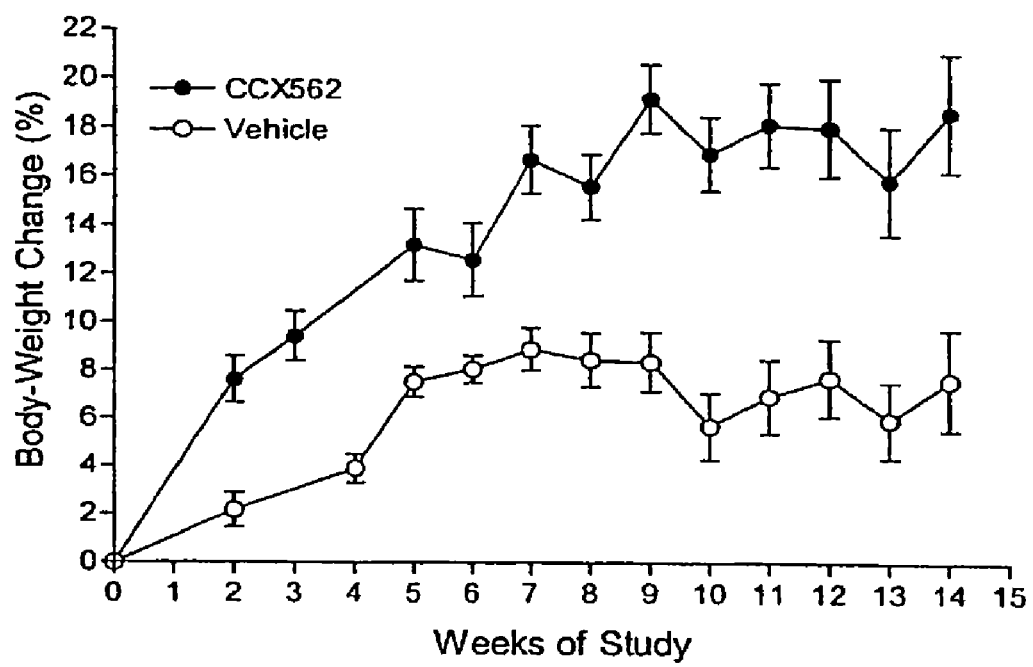

ARYL SULFONAMIDES

RELATED APPLICATIONS

This application is a continuation of U.S. Ser. No. 12/498,633 filed Jul. 7, 2009, abandoned, which is a continuation of U.S. Ser. No. 12/251,829 filed Oct. 15, 2008, abandoned, which is a continuation of U.S. Ser. No. 11/046,565 filed Jan. 27, 2005, now U.S. Pat. No. 7,582,661, which is a continuation of U.S. Ser. No. 10/716,170 filed Nov. 17, 2003, now U.S. Pat. No. 6,939,885, and claims priority to U.S. provisional application Ser. No. 60/427,670 filed Nov. 18, 2002. The disclosure of the priority application is incorporated by reference herein in its entirety.

BACKGROUND OF THE INVENTION

The present invention provides compounds, pharmaceutical compositions containing one or more of those compounds or their pharmaceutically acceptable salts, which are effective in inhibiting the binding or function of various chemokines, such TECK, to the CCR9 receptor. As antagonists or modulators for the CCR9 receptor, the compounds and compositions have utility in treating inflammatory and immune disorder conditions and diseases.

Chemokines are chemotactic cytokines that are released by a wide variety of cells and attract various types of immune system cells, such as macrophages, T cells, eosinophils, basophils and neutrophils, to sites of inflammation (reviewed in Schall, *Cytokine*, 3:165-183 (1991), Schall, of al., *Curr. Opin. Immunol.*, 6:865 873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ($[Ca^{2+}]$), granule exocytosis, integrin up-regulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

T lymphocyte (T cell) infiltration into the small intestine and colon has been linked to the pathogenesis of Coeliac diseases, food allergies, rheumatoid arthritis, human inflammatory bowel diseases (IBD) which include Crohn's disease and ulcerative colitis. Blocking trafficking of relevant T cell populations to the intestine can lead to an effective approach to treat human IBD. More recently, chemokine receptor 9 (CCR9) has been noted to be expressed on gut-homing T cells in peripheral blood, elevated in patients with small bowel inflammation such as Crohn's disease and celiac disease. The only CCR9 ligand identified to date, TECK (thymus-expressed chemokine) is expressed in the small intestine and the ligand receptor pair is now thought to play a pivotal role in the development of IBD. In particular, this pair mediates the migration of disease causing T cells to the intestine. See for example, Zaballos, et al., *J. Immunol.*, 162(10):5671-5675 (1999); Kunkel, et al., *J. Exp. Med.* 192(5):761-768 (2000); Papadakis, et al., *J. Immunol.*, 165(9):5069-5076 (2000); Papadakis, et al., *Gastroenterology*, 121(2):246-254 (2001); Campbell, et al., *J. Exp. Med.*, 195(1):135-141 (2002); Wurbel, et al., *Blood*, 98(9):2626-2632 (2001); and Uehara, et al., *J. Immunol*, 168(6):2811-2819 (2002).

The identification of compounds that modulate the function of CCR9 represents an attractive new family of therapeutic agents for the treatment of inflammatory and other conditions and diseases associated with CCR9 activation, such as inflammatory bowel disease.

BRIEF SUMMARY OF THE INVENTION

The present invention is directed to compounds and pharmaceutically acceptable salts thereof, compositions, and methods useful in modulating CCR9 chemokine activity. The compounds and salts thereof, compositions, and methods described herein are useful in treating or preventing CCR9-mediated conditions or diseases, including certain inflammatory and immunoregulatory disorders and diseases.

In one embodiment, the inventive compounds are of the formula (I):

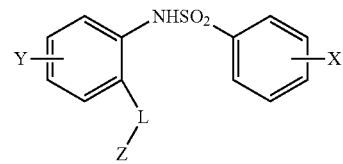

where X, Y and Z are as defined below. Salts of these compounds are also within the scope of the invention.

In another aspect, the present invention provides compositions useful in modulating CCR9 chemokine activity. In one embodiment, a composition according to the present invention comprises a compound according to the invention and a pharmaceutically acceptable carrier or excipient.

In yet another aspect, the present invention provides a method of modulating CCR9 function in a cell, comprising contacting the cell with a therapeutically effective amount of a compound or composition according to the invention.

In still another aspect, the present invention provides a method for modulating CCR9 function, comprising contacting a CCR9 protein with a therapeutically effective amount of a compound or composition according to the invention.

In still another aspect, the present invention provides a method for treating a CCR9-mediated condition or disease, comprising administering to a subject a safe and effective amount of a compound or composition according to the invention.

In addition to the compounds provided herein, the present invention further provides pharmaceutical compositions containing one or more of these compounds, as well as methods for the use of these compounds in therapeutic methods, primarily to treat diseases associated with CCR9 signaling activity.

BRIEF DESCRIPTION OF THE FIGURE

FIG. 1 is a graph showing in vivo efficacy for the CCR9 antagonist tested in Example 119. Closed triangle: vehicle; Open circle: CCR9 antagonist of the formula:

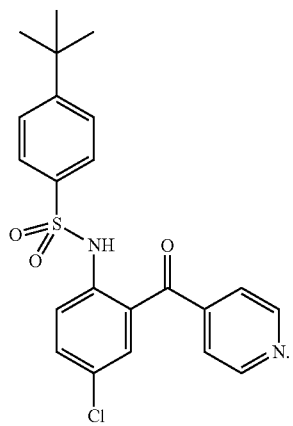

DETAILED DESCRIPTION OF THE INVENTION

General

The present invention is directed to compounds and salts thereof, compositions and methods useful in the modulation of chemokine receptor function, particularly CCR9 function. Modulation of chemokine receptor activity, as used herein in its various forms, is intended to encompass antagonism, agonism, partial antagonism, inverse agonism and/or partial agonism of the activity associated with a particular chemokine receptor, preferably the CCR9 receptor. Accordingly, the compounds of the present invention are compounds which modulate at least one function or characteristic of mammalian CCR9, for example, a human CCR9 protein. The ability of a compound to modulate the function of CCR9, can be demonstrated in a binding assay (e.g., ligand binding or agonist binding), a migration assay, a signaling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

Abbreviations and Definitions

When describing the compounds, compositions, methods and processes of this invention, the following terms have the following meanings, unless otherwise indicated.

When describing the compounds, compositions, methods and processes of this invention, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl and the like.

"Cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

"Alkylene" by itself or as part of another substituent means a divalent radical derived from an alkane, as exemplified by —CH$_2$CH$_2$CH$_2$CH$_2$—. Typically, alkyl (or alkylene) groups having 8 or fewer carbon atoms are preferred in the present invention.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl and the like.

"Alkoxy" and "alkylthio" (or thioalkoxy) are used in their conventional sense and refer to an alkyl groups attached to the remainder of the molecule via an oxygen atom or a sulfur atom, respectively. Examples of alkoxy and thioalkoxy include methoxy, ethoxy, isopropoxy, butoxy, cyclopentyloxy, thiomethoxy, and the like.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like.

"Aryl" refers to a polyunsaturated, aromatic hydrocarbon group having a single ring or multiple rings which are fused together or linked covalently. Aryl groups with 6-10 carbon atoms are preferred. Examples of aryl groups include phenyl and naphthalene-1-yl, naphthalene-2-yl, biphenyl and the like.

"Halo" or "halogen", by itself or as part of a substituent refers to a chlorine, bromine, iodine, or fluorine atom. Additionally, "haloalkyl" refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic group containing at least one heteroatom. "Heteroaryl" refers to an aromatic group containing at least one heteroatom. Each heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-3 nitrogen atoms, 0-1 sulfur atoms and 0-1 oxygen atoms. Examples of saturated and unsaturated heterocyclyl groups include pyrrolidine, imidazolidine, pyrazolidine, piperidine, 1,4-dioxane, morpholine, thiomorpholine, piperazine, 3-pyrroline and the like. Examples of unsaturated and aromatic heterocyl groups include pyrrole, imidazole, thiazole, oxazole, furan, thiophene, triazole, tetrazole, oxadiazole, pyrazole, isoxazole, isothiazole, pyridine, pyrazine, pyridazine, pyrimidine, triazine, indole, benzofuran, benzothiophene, benzimidazole, benzopyrazole, benzthiazole, quinoline, isoquinoline, quinazoline, quinoxaline and the like. Heterocyclyl and heteroaryl groups can be unsubstituted or substituted. For substituted groups, the substitution may be on a carbon or heteroatom. For example, when the substitution is =O, the resulting group may have either a carbonyl (—C(O)—) or a N-oxide (—N(O)—).

Suitable substituents for substituted alkyl, substituted alkenyl, substituted alkynyl and substituted cycloalkyl include -halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —S(O)R', —S(O)$_2$R', —S(O)$_2$NR'R", —NR'S(O)$_2$R", —CN, oxo (=O or —O—) and —NO$_2$ in a number ranging from zero to (2 m'+1), where m' is the total number of carbon atoms in such radical.

Suitable substituents for substituted aryl, substituted heteroaryl and substituted heterocyclyl include -halogen, unsubstituted or substituted alkyl, unsubstituted or substituted alkenyl, unsubstituted or substituted alkynyl, unsubstituted or substituted cycloalkyl, —OR', oxo (=O or —O), —OC(O) R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$) =NH, —NR'C(NH$_2$)=NH, —NH—C(NH$_2$)=NR', —S(O) R', —S(O)$_2$R', —S(O)$_2$NR'R", —NR'S(O)$_2$R" and —N$_3$ in a number ranging from zero to the total number of open valences on the aromatic ring system.

As used above, R', R" and R''' each independently refer to a variety of groups including hydrogen, halogen, unsubstituted or substituted $C_{1-8}$ alkyl, unsubstituted or substituted $C_{3-6}$ cycloalkyl, unsubstituted or substituted $C_{2-8}$ alkenyl, unsubstituted or substituted $C_{2-8}$ alkynyl, unsubstituted or substituted aryl, unsubstituted or substituted heteroaryl, unsubstituted or substituted heterocyclyl. Preferably, R', R" and R''' independently refer to a variety of groups selected from the group consisting of hydrogen, unsubstituted $C_{1-8}$ alkyl, unsubstituted heteroalkyl, unsubstituted aryl, aryl substituted with 1-3 halogens, unsubstituted $C_{1-8}$ alkyl, unsubstituted $C_{1-8}$ alkoxy, unsubstituted $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl).

Alternatively, two of the substituents on adjacent atoms of the aryl, heteroaryl or heterocycyl ring may optionally be replaced with a substituent of the formula -T-C(O)—$(CH_2)_q$—U—, wherein T and U are independently —NR'—, —O—, —$CH_2$— or a single bond, and q is an integer of from 0 to 2. Alternatively, two of the substituents on adjacent atoms of the aryl or heteroaryl ring may optionally be replaced with a substituent of the formula -A-$(CH_2)_r$—B—, wherein A and B are independently —$CH_2$—, —O—, —NR'—, —S—, —S(O)—, —$S(O)_2$—, —$S(O)_2NR'$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —$S(O)_2$—, or —$S(O)_2NR'$—. The substituent R' in —NR'— and —$S(O)_2NR'$— is selected from hydrogen or unsubstituted $C_{1-6}$ alkyl.

"Heteroatom" is meant to include oxygen (O), nitrogen (N), sulfur (S) and silicon (Si).

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M., et al, "Pharmaceutical Salts", *J. Pharmaceutical Science,* 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

"Therapeutically effective amount" refers to an amount sufficient to effect treatment when administered to a patient in need of treatment.

"Treating" or "treatment" as used herein refers to the treating or treatment of a disease or medical condition (such as a bacterial infection) in a patient, such as a mammal (particularly a human or a companion animal) which includes:

ameliorating the disease or medical condition, i.e., eliminating or causing regression of the disease or medical condition in a patient;

suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Compounds that Modulate CCR9 Activity

The present invention provides compounds that modulate CCR9 activity. Specifically, the invention provides compounds having anti-inflammatory or immunoregulatory activity. The compounds of the invention are thought to interfere with inappropriate T-cell trafficking by specifically modulating or inhibiting a chemokine receptor function. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

Without intending to be bound by any particular theory, it is believed that the compounds provided herein interfere with the interaction between a chemokine receptor and one or more cognate ligands. In particular, it is believed that the compounds interfere with the interaction between CCR9 and a CCR9 ligand, such as TECK. Compounds contemplated by the invention include, but are not limited to, the exemplary compounds provided herein and salts thereof.

For example, compounds of this invention act as potent CCR9 antagonists, and this antagonistic activity has been further confirmed in animal testing for inflammation, one of the hallmark disease states for CCR9. Accordingly, the compounds provided herein are useful in pharmaceutical compositions, methods for the treatment of CCR9-mediated diseases, and as controls in assays for the identification of competitive CCR9 antagonists.

CCR9 Antagonists as Treatments of Cancer

In additional to inflammatory diseases, cancers that are caused by uncontrolled proliferation of T cells may be treated with a CCR9 antagonist. Certain types of cancer are caused by T cells expressing chemokine receptor CCR9. For example, thymoma and thymic carcinoma are diseases in which cancer cells are found in the tissues of the thymus, an organ where lymphocyte development occurs. T cells in the thymus, called thymocytes, are known to express functional CCR9; its ligand is highly expressed in the thymus. Another example is the acute lymphocytic leukemia (ALL), also called acute lymphoblastic leukemia and acute, is a common leukemia, which can occur in children as well as adults. Recent studies have shown that T cells in patients with ALL selectively express high level of CCR9 (Qiuping Z et al., Cancer Res. 2003, 1; 63(19):6469-77)

Chemokine receptors have been implicated in cancer. Although the exact mechanisms of chemokine receptors' involvements have yet to be full understood, such receptors are known to promote the growth of cancer cells (proliferation), facilitate the spread of cancer cells (metastasis) or help them resist program cell death (apoptosis). For example, CCR9 in a cancer T cell line MOLT-4 provides the cells with a survival signal, allowing them to resist apoptosis (Youn B S, et al., Apoptosis. 2002 June; 7(3):271-6). In the cases of thymoma, thymic carcinoma and acute lymphocytic leukemia, it is likely that CCR9 plays a key in the survival and proliferation these cells. Thus, blocking the signaling of CCR9 should help prevent their expansion and metastasis.

Compounds of the Invention

The compounds provided herein have the general formula (I):

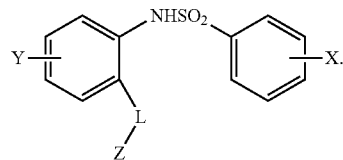

X Substituents

X represents from 1 to 4 substituents independently selected from the group consisting of halogen, —CN, —NO$_2$, —OH, —OR$^1$, —C(O)R$^1$, —CO$_2$R$^1$, —O(CO)R$^1$, —C(O)NR$^1$R$^2$, —OC(O)NR$^1$R$^2$, —SR$^1$, —SOR$^1$, —SO$_2$R$^1$, —SO$_2$NR$^1$R$^2$, —NR$^1$R$^2$, —NR$^1$C(O)R$^2$, —NR$^1$C(O)$_2$R$^2$, —NR$^1$SO$_2$R$^2$, —NR$^1$(CO)NR$^1$R$^2$, unsubstituted or substituted C$_{1-8}$ alkyl, unsubstituted or substituted C$_{2-8}$ alkenyl, unsubstituted or substituted C$_{2-8}$ alkynyl, unsubstituted or substituted C$_{3-8}$ cycloalkyl, unsubstituted or substituted C$_{6-10}$ aryl, unsubstituted or substituted 5- to 10-membered heteroaryl, and unsubstituted or substituted 3- to 10-membered heterocyclyl.

When X is substituted C$_{1-8}$ alkyl, substituted C$_{3-8}$ cycloalkyl, substituted C$_{2-8}$ alkenyl, or substituted C$_{2-8}$ alkynyl, it may have from 1-5 substituents independently selected from the group consisting of halogen, —OH, —CN, —NO$_2$, =O, —OC(O)R$^1$, —C(O)R$^1$, —CONR$^1$R$^2$, —OC(O)NR$^1$R$^2$, —NR$^2$C(O)R$^1$, —NR$^1$C(O)NR$^2$R$^3$, —CO$_2$R$^1$, —NR$^1$R$^2$, —NR$^2$CO$_2$R$^1$, —SR$^1$, —SOR$^1$, —SO$_2$R$^1$, —SO$_2$NR$^1$R$^2$, —NR$^1$SO$_2$R$^2$, unsubstituted or substituted aryl, unsubstituted or substituted heteroaryl, and unsubstituted or substituted heterocyclyl.

When X is substituted C$_{6-10}$ aryl, substituted 5- to 10-membered heteroaryl, or substituted 3- to 10-membered heterocyclyl, it may have from 1-4 substituents independently selected from the group consisting of halogen, unsubstituted or substituted C$_{1-8}$ alkyl, unsubstituted or substituted C$_{1-8}$ haloalkyl, —CN, —NO$_2$, —OH, —OR$^1$, =O, —OC(O)R$^1$, —CO$_2$R$^1$, —C(O)R$^1$, —CONR$^1$R$^2$, —OC(O)NR$^1$R$^2$, —NR$^2$C(O)R$^1$, —NR$^1$C(O)NR$^2$R$^3$, —NR$^1$R$^2$, —NR$^2$CO$_2$R$^1$, —SR$^1$, —SOR$^1$, —SO$_2$R$^1$, —SO$_2$NR$^1$R$^2$, and —NR$^1$SO$_2$R$^2$. Suitable substituted C$_{1-8}$ alkyl include those defined above in paragraph [0051].

R$^1$, R$^2$ and R$^3$ are each independently selected from the group consisting of hydrogen, C$_{1-6}$ haloalkyl, C$_{1-6}$ alkyl, C$_{3-6}$ cycloalkyl, C$_{2-6}$ alkenyl, C$_{2-6}$ alkynyl, C$_{6-10}$ aryl, 5- to 10-membered heteroaryl, aryl-C$_{1-4}$ alkyl, aryl-C$_{1-4}$ alkyl, and aryloxy-C$_{1-4}$ alkyl. Each can be unsubstituted or substituted with from 1-3 substituents independently selected from the group consisting of halogen, —OH, —OR', —OCOHNR', —OCONR'$_2$, —SH, —SR', —SO$_2$NH$_2$, —CONH$_2$, —NHC(O)NH$_2$, NR'C(O)NH$_2$, —CO$_2$H, —CN, —NO$_2$, —NH$_2$, —NHR' and —NR'$_2$, —S(O)R', —S(O)$_2$R', —CO$_2$R', —CONR'$_2$, —CONHR', —C(O)R', —NR'COR', —NHCOR', —NR'CO$_2$R', —NHCO$_2$R', —CO$_2$R', —NR'C(O)

NR'$_2$, —NHC(O)NR'$_2$, —NR'C(O)NHR', —NHC(O)NHR', —NR'SO$_2$R', —NHSO$_2$R', —SO$_2$NR'$_2$, and —SO$_2$NHR'. Alternatively, two of R$^1$, R$^2$ and R$^3$ together with the atom(s) to which they are attached, may form a 5-, 6- or 7-membered ring.

Y Substituents

Y represents from 1 to 3 substituents, each independently selected from the group consisting of halogen, —CN, —NO$_2$, —OH, —OR$^4$, —C(O)R$^4$, —CO$_2$R$^4$, —SR$^4$, —SOR$^4$, —SO$_2$R$^4$, and unsubstituted or substituted C$_{1-4}$ alkyl.

When Y is a substituted C$_{1-4}$ alkyl, it may have from 1 to 3 substituents independently selected from the group consisting of halogen, —OH, —OR$^4$, —CN, —NO$_2$, =O, —OC(O)R$^4$, —CO$_2$R$^4$, —C(O)R$^4$, —CONR$^4$R$^5$, —OC(O)NR$^4$R$^5$, —NR$^4$C(O)R$^5$, —NR$^4$C(O)NR$^5$R$^6$, —NR$^4$R$^5$, —NR$^4$CO$_2$R$^5$, —SR$^4$, —SOR$^4$, —SO$_2$R$^4$, —SO$_2$NR$^4$R$^5$, and —NR$^4$SO$_2$R$^5$.

R$^4$, R$^5$ and R$^6$ are each independently selected from the group consisting of hydrogen, unsubstituted or substituted C$_{1-6}$ haloalkyl, unsubstituted or substituted C$_{1-6}$ alkyl, unsubstituted or substituted C$_{3-6}$ cycloalkyl, unsubstituted or substituted C$_{2-6}$ alkenyl, and unsubstituted or substituted C$_{2-6}$ alkynyl. Each can be unsubstituted or substituted with from 1 to 3 substituents independently selected from the group consisting of —OH, —OR', —SH, —SR', —CN, —NO$_2$, —NH$_2$, —NHR', —NR'$_2$, —S(O)R', —S(O)$_2$R', —CO$_2$R', —CONHR', —CONR'$_2$, and —C(O)R'. Additionally, two of R$^4$, R$^5$ and R$^6$ together with the atom(s) to which they are attached, may form a 5-, 6- or 7-membered ring.

Linkers

L is —C(O)—, —S—, —SO— or —S(O)$_2$—.

Z Substituents

Z represents either unsubstituted or substituted monocyclic or bicyclic C$_{5-10}$ heteroaryl or unsubstituted or substituted monocyclic or bicyclic C$_{3-10}$ heterocyclyl.

When Z is a substituted heteroaryl or substituted heterocyclyl, it may have from 1 to 5 substituents independently selected from the group consisting of halogen, unsubstituted or substituted C$_{1-8}$ alkyl, unsubstituted or substituted C$_{1-8}$ cycloalkyl, unsubstituted or substituted C$_{2-8}$ alkenyl, unsubstituted or substituted C$_{2-8}$ alkynyl, unsubstituted or substituted C$_{1-8}$ alkoxy, =O, —CN, —NO$_2$, —OH, —OR$^7$, —OC(O)R$^7$, —CO$_2$R$^7$, —C(O)R$^7$, —CONR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —SOR$^7$, —SO$_2$R$^7$, —SO$_2$NR$^7$R$^8$, —NR$^7$SO$_2$R$^8$, unsubstituted or substituted C$_{6-10}$ aryl, unsubstituted or substituted heteroaryl and unsubstituted or substituted heterocyclyl.

Suitable substituted C$_{1-8}$ alkyl, C$_{3-8}$ cycloalkyl, C$_{2-8}$ alkenyl, C$_{2-8}$ alkynyl and C$_{1-8}$ alkoxy substituents on Z may have from 1 to 5 substituents independently selected from the group consisting of halogen, —OH, —OR$^7$, —CN, —NO$_2$, =O, —CN, —NO$_2$, —OC(O)R$^7$, —CO$_2$R$^7$, —C(O)R$^7$, —CONR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —SOR$^7$, —SO$_2$R$^7$, —SO$_2$NR$^7$R$^8$, —NR$^7$SO$_2$R$^8$, unsubstituted or substituted phenyl, unsubstituted or substituted 5- or 6-membered heteroaryl, or unsubstituted or substituted 3- to 6-membered heterocyclyl.

Suitable substituted aryl, heteroaryl and heterocyclyl substituents on Z may have from 1 to 5 substituents independently selected from the group consisting of halogen, —OH, —OR$^7$, —CN, —NO$_2$, =O, —CN, —NO$_2$, —OC(O)R$^7$, —OC(O)R$^7$, —CO$_2$R$^7$, —C(O)R$^7$, —CONR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —SOR$^7$, —SO$_2$R$^7$, —SO$_2$NR$^7$R$^8$, —NR$^7$SO$_2$R$^8$ and unsubstituted or substituted C$_{3-6}$ heterocyclyl.

R$^7$, R$^8$ and R$^9$ are each independently hydrogen, unsubstituted or substituted C$_{1-6}$ haloalkyl, unsubstituted or substituted C$_{1-6}$ alkyl, unsubstituted or substituted C$_{3-6}$ cycloalkyl, unsubstituted or substituted C$_{2-6}$ alkenyl, unsubstituted or substituted C$_{2-6}$ alkynyl, unsubstituted or substituted phenyl or unsubstituted or substituted heteroaryl, unsubstituted or substituted aryl-C$_{1-4}$ alkyl, and unsubstituted or substituted aryloxy-C$_{1-4}$ alkyl. Each can be substituted with from 1 to 3 substituents independently selected from the group consisting of halogen, —OH, —OR', —OCONHR', —OCONR'$_2$, —SH, —SR', —SO$_2$NH$_2$, —CONH$_2$, —NHC(O)NH$_2$, NR'C(O)NH$_2$, —CO$_2$H, —CN, —NO$_2$, —NH$_2$, —NHR' and —NR'$_2$, —S(O)R', —S(O)$_2$R', —CO$_2$R', —CONR'$_2$, —CONHR', —C(O)R', —NR'COR', —NHCOR', —NR'CO$_2$R', —NHCO$_2$R', —CO$_2$R', —NR'C(O)NR'$_2$, —NHC(O)NR'$_2$, —NR'C(O)NHR', —NHC(O)NHR', —NR'SO$_2$R', —NHSO$_2$R', —SO$_2$NR'$_2$, and —SO$_2$NHR'. R' is defined above. It is preferably, unsubstituted or substituted C$_{1-6}$ alkyl. Alternatively, two of R$^7$, R$^8$ and R$^9$ together with the atom(s) to which they are attached, may form a 5-, 6- or 7-membered ring.

Known Compounds

Compounds of the formula (I) where X is methyl when Z is 2-thiophene, 2-(3-hydroxy-1H-indole) or 3-(1-methylpyridinium) are known, but not as CCR9 antagonists.

Preferred X Substituents

X preferably represents from 1 to 3 substituents independently selected from the group consisting of halogen, —CN, —NO$_2$, —OH, —OR$^1$, —C(O)R$^1$, —CO$_2$R$^1$, —O(CO)R$^1$, —OC(O)NR$^1$R$^2$, —SR$^1$, —SOR$^1$, —SO$_2$R$^1$, —NR$^1$R$^2$, —NR$^1$C(O)R$^2$, —NR$^1$C(O)$_2$R$^2$, —NR$^1$(CO)NR$^1$R$^2$, unsubstituted or substituted C$_{1-8}$ alkyl, unsubstituted or substituted C$_{2-8}$ alkenyl, unsubstituted or substituted C$_{2-8}$ alkynyl, unsubstituted or substituted C$_{3-8}$ cycloalkyl, unsubstituted or substituted C$_{6-10}$ aryl, unsubstituted or substituted 5- or 6-membered heteroaryl, or unsubstituted or substituted 4- to 7-membered heterocyclyl.

X more preferably represents 1 or 2 substituents independently selected from the group consisting of —NO$_2$, —OR$^1$, —C(O)R$^1$, —SO$_2$R$^1$, —NR$^1$R$^2$, unsubstituted or substituted C$_{1-8}$ alkyl, unsubstituted or substituted phenyl, unsubstituted or substituted 5- or 6-membered heteroaryl, or unsubstituted or substituted 5- or 6-membered heterocyclyl. More preferably, at least one X substituent is situated para to the sulfonamido bond as defined in formula (I).

When X is substituted C$_{1-8}$ alkyl or substituted C$_{3-8}$ cycloalkyl, it preferably has from 1 to 3 substituents independently selected from the group consisting of halogen, —OH, —CN, =O, —OC(O)R$^1$, —C(O)R$^1$, —CONR$^1$R$^2$, —NR$^2$C(O)R$^1$, —CO$_2$R$^1$, —NR$^1$R$^2$, —SR$^1$, —SOR$^1$, —SO$_2$R$^1$, —NR$^1$SO$_2$R$^2$, unsubstituted or substituted aryl, and unsubstituted or substituted heteroaryl. When X is a substituted C$_{1-8}$alkyl, it more preferably has from 1 to 3 substituents independently selected from the group consisting of halogen, —OH, —CN, =O, —OC(O)R$^1$, —OR$^1$, —C(O)R$^1$, —CONR$^1$R$^2$, —NR$^2$C(O)R$^1$, —CO$_2$R$^1$, —NR$^1$R$^2$, —SO$_2$R$^1$, unsubstituted or substituted aryl, and unsubstituted or substituted heteroaryl.

When X is substituted C$_{6-10}$ aryl or substituted heteroaryl, it preferably has from 1 to 3 substituents independently selected from the group consisting of halogen, —CN, —OH, —OR$^1$, =O, —OC(O)R$^1$, —CO$_2$R$^1$, —C(O)R$^1$, —CONR$^1$R$^2$, —NR$^2$C(O)R$^1$, —NR$^1$R$^2$, —SR', —SOR$^1$, —SO$_2$R$^1$, —NR$^1$SO$_2$R$^2$, unsubstituted or substituted C$_{1-8}$ alkyl, and C$_{1-8}$ unsubstituted or substituted haloalkyl. When X is a substituted phenyl or substituted 5- or 6-membered heteroaryl, it is more preferably has from 1 to 3 substituents independently selected from the group consisting of halogen, —OH, —OR$^1$, —C(O)R$^1$, —CONR$^1$R$^2$, —NR$^2$C(O)R$^1$, —NR$^1$R$^2$, —SO$_2$R$^1$, unsubstituted or substituted C$_{1-8}$ alkyl, and unsubstituted or substituted C$_{1-8}$ haloalkyl.

When X is a substituted 4- to 7-membered heterocyclyl, it preferably has from 1 to 3 substituents independently selected from the group consisting of unsubstituted or substituted C$_{1-8}$ alkyl, C$_{1-8}$ haloalkyl, —OR$^1$, —OH, —OC(O)R$^1$, —CO$_2$R$^1$, —C(O)R$^1$, —CONR$^1$R$^2$, —NR$^1$R$^2$, —SO$_2$R$^1$, and —NR$^1$SO$_2$R$^2$. When X is a 5- or 6-membered heterocyclyl, it more preferably has 1 to 2 substituents independently selected from the group consisting of unsubstituted or substituted C$_{1-8}$ alkyl, unsubstituted or substituted C$_{1-8}$ haloalkyl, unsubstituted or substituted C$_{1-8}$ haloalkyl, —OR$^1$, —OH, —C(O)R$^1$, —CONR$^1$R$^2$, —NR$^1$R$^2$, and —SO$_2$R$^1$.

Preferred Y Substituents

Y preferably represents from 1 to 3 substituents independently selected from the group consisting of halogen, —CN, —NO$_2$, —OR$^4$, —C(O)R$^4$, —SR$^4$, —CF$_3$, —SOR$^4$, and —SO$_2$R$^4$. Y more preferably represents from 1 to 3 substituents independently selected from the group consisting of halogen, —CN, —NO$_2$, —CF$_3$, and —SO$_2$R$^4$. Y most preferably represents 1 or 2 substituents where at least halogen is present and optionally another substituent selected from the group consisting of —CN, —NO$_2$, —OH, —OR$^4$, —C(O)R$^4$, —CO$_2$R$^4$, —SOR$^4$, —SO$_2$R$^4$ and unsubstituted or substituted C$_{1-4}$ alkyl. Most preferably, at least one Y substituent is located para to the sulfonamide bond as defined in formula (I), and one Y substituent is halogen.

When Y is substituted alkyl, it preferably has from 1 to 3 substituents independently selected from the group consisting of halogen, —OH, —OR$^4$, —CN, —NO$_2$, =O, —OC(O)R$^4$, —CO$_2$R$^4$, —C(O)R$^4$, —CONR$^4$R$^5$, —NR$^4$C(O)R$^5$, —NR$^4$R$^5$, —NR$^4$, —SR$^4$, —SOR$^4$, —SO$_2$R$^4$, and —NR$^4$SO$_2$R$^5$.

Preferred Linkers

L is preferably —C(O)—.

Preferred Z Substituents

Z preferably represents an unsubstituted or substituted 5- or 6-membered heteroaryl.

When Z is a substituted 5- or 6-membered heteroaryl, it preferably has from 1 to 3 substituents independently selected from the group consisting of halogen, unsubstituted or substituted C$_{1-8}$ alkyl, unsubstituted or substituted C$_{3-8}$ cycloalkyl, unsubstituted or substituted C$_{2-8}$ alkenyl, unsubstituted or substituted C$_{2-8}$ alkynyl, unsubstituted or substituted C$_{1-8}$ alkoxy, =O, —CN, —NO$_2$, —OH, —OR$^7$, —OC(O)R$^7$, —CO$_2$R$^7$, —C(O)R$^7$, —CONR$^7$R$^8$, —NR$^7$C(O)R$^8$, —NR$^7$R$^8$, —SR$^7$, —SOR$^7$, —SO$_2$R$^7$, —SO$_2$NR$^7$R$^8$, —NR$^7$SO$_2$R$^8$, unsubstituted or substituted phenyl, unsubstituted or substituted 5- or 6-membered heteroaryl, and unsubstituted or substituted 3- to 7-membered heterocyclyl. If present, one substituent is preferably located ortho to one of the heteroatoms in the ring or is directly connected to a ring heteroatom.

Z more preferably represents unsubstituted or substituted 6-membered heteroaryl with carbon and up to 3 nitrogen atoms and with from 1 to 3 substituents independently selected from the group consisting of halogen, C$_{1-8}$ alkyl, C$_{3-8}$ cycloalkyl, C$_{2-8}$ alkenyl, C$_{2-8}$ alkynyl, C$_{1-8}$ alkoxy, =O, —CN, —NO$_2$, —OH, —OR$^7$, —OC(O)R$^7$, —CO$_2$R$^7$, —C(O)R$^7$, —CONR$^7$R$^8$, —NR$^7$C(O)R$^8$, —NR$^7$R$^8$, —SR$^7$, —SOR$^7$, —SO$_2$R$^7$, —SO$_2$NR$^7$R$^8$, —NR$^7$SO$_2$R$^8$, unsubstituted or substituted phenyl, unsubstituted or substituted 5- and 6-membered heteroaryl, and unsubstituted or substituted 3- to 6-membered heterocyclyl. In this embodiment, Z can be any unsubstituted or substituted chemically allowed regioisomers of pyridyl, pyrimidinyl, pyridazinyl, pyrazinyl and the like and their respective N-oxides. In preferred embodiments, Z is pyridinyl with from 0 to 3 substituents; pyrimidinyl with from 0 to 3 substituents; pyrazinyl with from 0 to 3 substituents; or pyridazinyl with from 0 to 3 substituents (especially, where one ring nitrogen has a =O substituent).

Z most preferably represents unsubstituted or substituted 6-membered heteroaryl with carbon and 1 to 2 nitrogen atoms and with 1 or 2 substituents independently selected from the group consisting of halogen, C$_{1-6}$ alkyl, C$_{1-6}$ alkoxy, =O, —CN, —NO$_2$, —OH, —OR$^7$, —C(O)R$^7$, —CONR$^7$R$^8$, —NR$^7$C(O)R$^8$, —NR$^7$R$^8$, —SR$^7$, —SOR$^7$, —SO$_2$R$^7$, —SO$_2$NR$^7$R$^8$, —NR$^7$SO$_2$R$^8$, 5- or 6-membered heteroaryl and a 3- to 7-membered heterocyclyl. In this embodiment, Z can be any chemically allowed regioisomers of pyridyl, pyrimidinyl, pyridazinyl, pyrazinyl and the like, and their respective N-oxides.

When the substituent on Z is substituted C$_{1-8}$ alkyl, substituted C$_{3-8}$ cycloalkyl, substituted C$_{2-8}$ alkenyl, substituted C$_{2-8}$ alkynyl or substituted C$_{1-8}$ alkoxy groups, it preferably has from 1 to 3 substituents independently selected from the group consisting of halogen, —OH, —OR$^7$, =O, —CO$_2$R$^7$, —C(O)R$^7$, —CONR$^7$R$^8$, —NR$^7$C(O)R$^8$, —NR$^7$R$^8$, —SR$^7$, —SOR$^7$, —SO$_2$R$^7$, —NR$^7$SO$_2$R$^8$, unsubstituted or substituted phenyl, unsubstituted or substituted 5- or 6-membered heteroaryl, and unsubstituted or substituted 3- to 6-membered heterocyclyl. More preferably, it has from 1 to 3 substituents independently selected from the group consisting of halogen, —OH, —OR$^7$, =O, —C(O)R$^7$, —CO$_2$R$^7$, —CONR$^7$R$^8$, —NR$^7$C(O)R$^8$, —NR$^7$R$^8$, —SR$^7$, —SOR$^7$, —SO$_2$R$^7$, —SO$_2$NR$^7$R$^8$, —NR$^7$SO$_2$R$^8$, and 3- to 6-membered heterocyclyl.

When the substituent on Z is substituted phenyl or substituted heteroaryl, it preferably has from 1 to 3 substituents independently selected from the group consisting of halogen, —OH, —CN, —NO$_2$, =O, —CN, —NO$_2$, —OC(O)R$^7$, —CO$_2$R$^7$, —C(O)R$^7$, —CONR$^7$R$^8$, —NR$^7$C(O)R$^8$, —NR$^7$R$^8$, —SR$^7$, —SOR$^7$, —SO$_2$R$^7$, —NR$^7$SO$_2$R$^8$, unsubstituted or substituted C$_{1-8}$ alkyl, unsubstituted or substituted C$_{1-8}$ haloalkyl, unsubstituted or substituted C$_{3-8}$ cycloalkyl, and 3- to 6-membered heterocyclyl.

When the substituent on Z is substituted heterocyclyl, it preferably has from 1 to 2 substituents independently selected from the group consisting of unsubstituted or substituted C$_{1-8}$ alkyl, C$_{1-8}$ haloalkyl, —OR$^7$, —OH, —C(O)R$^7$, —CONR$^7$R$^8$, —NR$^7$R$^8$, and —SO$_2$R$^7$.

Preferred Compounds

In several preferred embodiments, the compounds are represented by the following formulae:

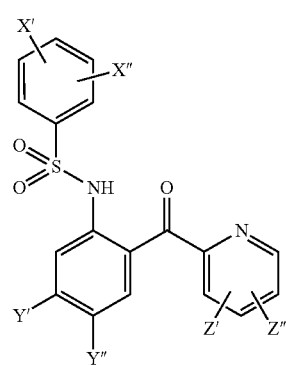

IIa

-continued
IIb
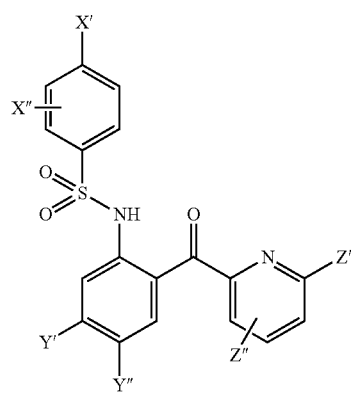
IIc
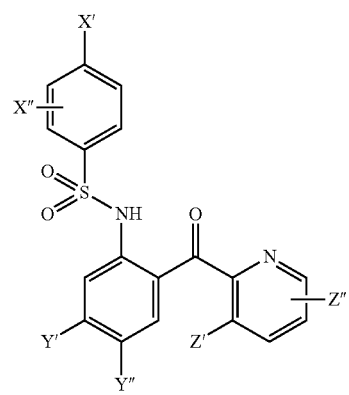
IId
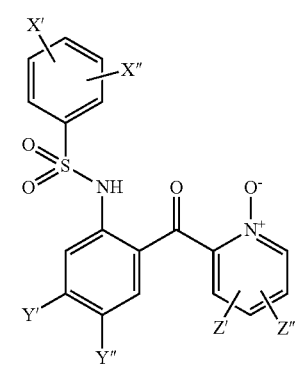
IIe
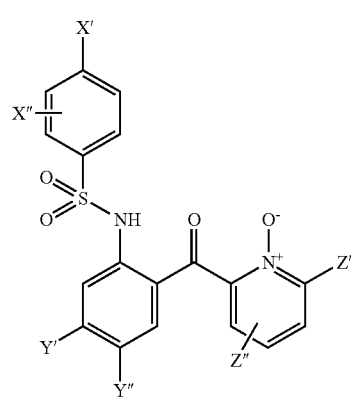
IIf
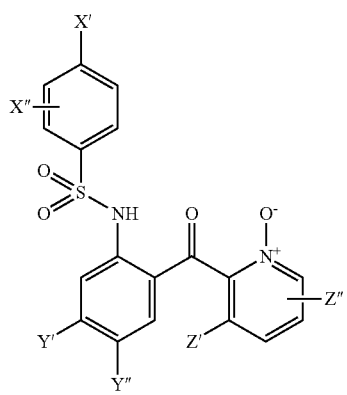
IIIa
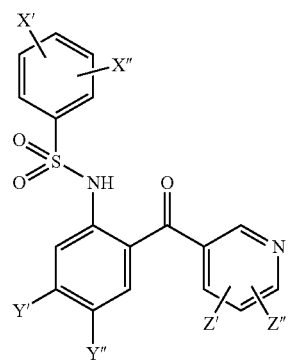
IIIb
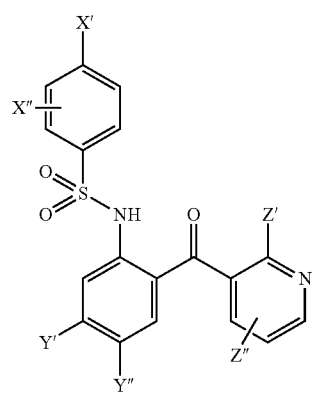
IIIc
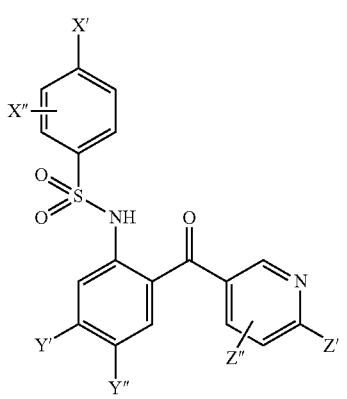

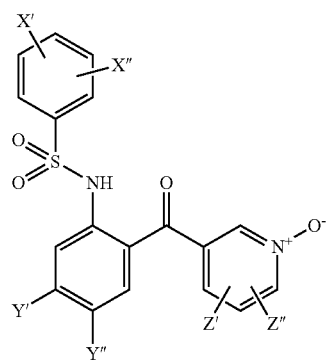
IIId
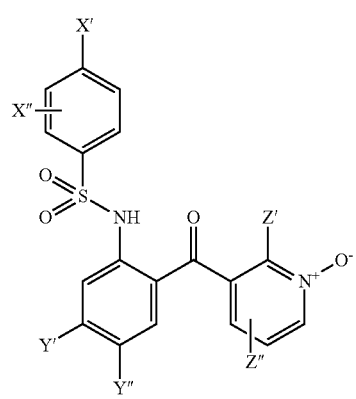
IIIe
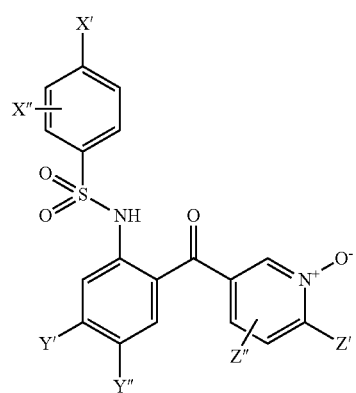
IIIf
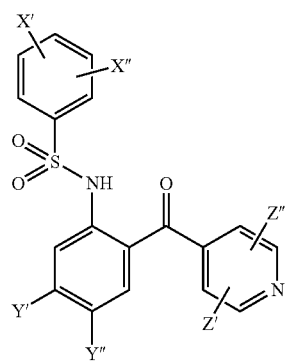
IVa
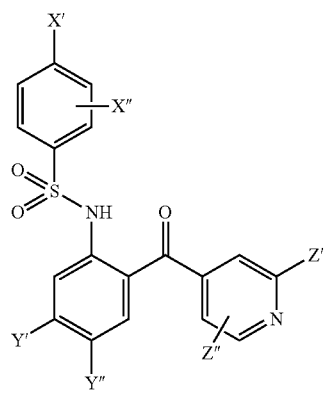
IVb
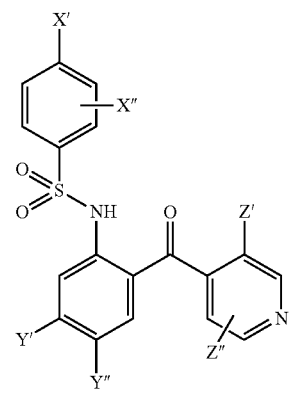
IVc
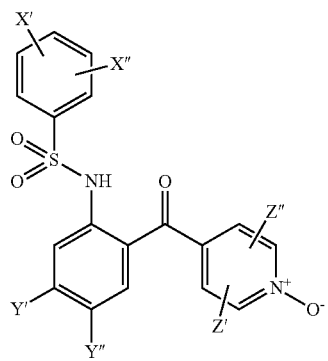
IVd
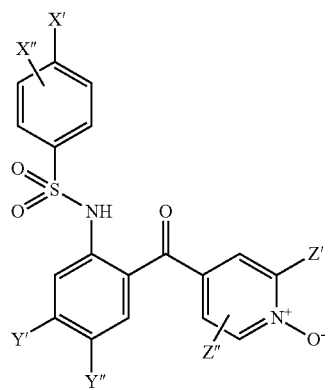
IVe 17
-continued IVf
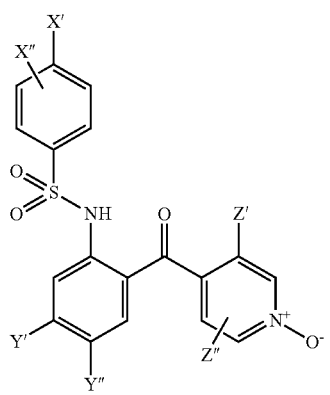

V
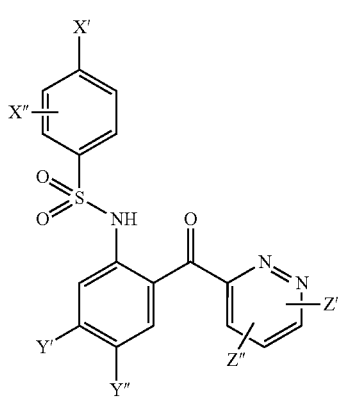

VI
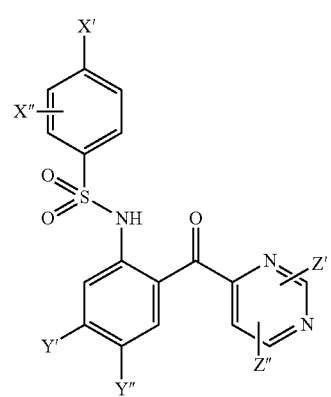

VII
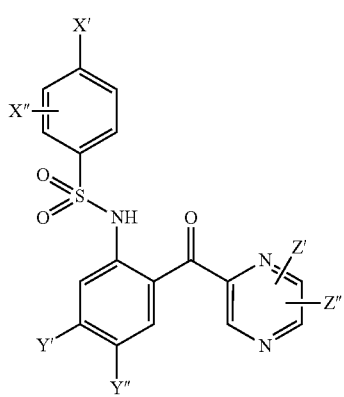

18
-continued

VIII
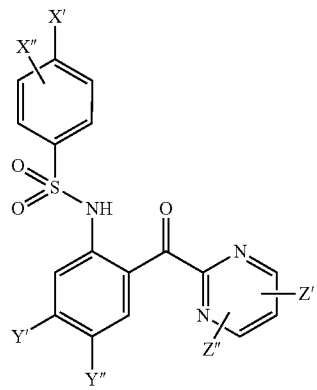

IX
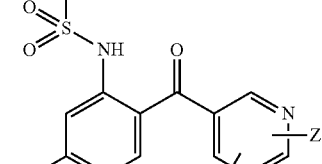

X
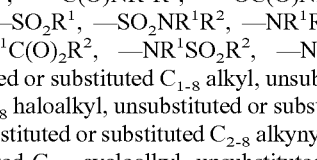

In each of the above formulae, X' and X" are each independently selected from the group consisting of hydrogen, halogen, —CN, —NO$_2$, —OH, —OR$^1$, —C(O)R$^1$, —CO$_2$R$^1$, —O(CO)R$^1$, —C(O)NR$^1$R$^2$, —OC(O)NR$^1$R$^2$, —SR$^1$, —SOR$^1$, —SO$_2$R$^1$, —SO$_2$NR$^1$R$^2$, —NR$^1$R$^2$, —NR$^1$C(O)R$^2$, —NR$^1$C(O)$_2$R$^2$, —NR$^1$SO$_2$R$^2$, —NR$^1$(CO)NR$^1$R$^2$, unsubstituted or substituted C$_{1-8}$ alkyl, unsubstituted or substituted C$_{1-8}$ haloalkyl, unsubstituted or substituted C$_{2-8}$ alkenyl, unsubstituted or substituted C$_{2-8}$ alkynyl, unsubstituted or substituted C$_{3-8}$ cycloalkyl, unsubstituted or substituted C$_{6-10}$ aryl, unsubstituted or substituted 5- to 10-membered heteroaryl, and unsubstituted or substituted 3- to 10-membered heterocyclyl, with the proviso that X' and X" cannot both be hydrogen simultaneously.

In one preferred embodiment, X' and X" are each independently selected from the group consisting of hydrogen, —NO$_2$, —OR$^1$, —C(O)R$^1$, —SO$_2$R$^1$, —NR$^1$R$^2$, unsubstituted or substituted C$_{1-8}$ alkyl, unsubstituted or substituted $C_{1-8}$ haloalkyl, unsubstituted or substituted $C_{3-8}$ cycloalkyl, unsubstituted or substituted $C_{2-8}$ alkenyl, unsubstituted or substituted phenyl, unsubstituted or substituted 5- or 6-membered heteroaryl, unsubstituted or substituted 5- or 6-membered heterocyclyl, with the proviso that X' and X" cannot both be hydrogen simultaneously.

In another preferred embodiment, X' and X" are each independently selected from the group consisting of hydrogen, —$CF_3$, —$CH=CH_2$, isoamyl, phenylacetylene, t-butyl, ethyl (Et), i-propyl ($^i$Pr), —$C(CH_3)_2CH_2CH_3$, hydroxybutyl, —$C(CH_3)_2CH_2CH_2OH$, —$CH_2CH_2CO_2Me$, —$OCF_3$, —OMe, —O-$^i$Pr, —C(O)Me, —$SO_2$Me, phenyl (Ph), —OEt, pyrazole, oxazole, and morpholinyl, with the proviso that X' and X" cannot both be hydrogen simultaneously.

In each of the above formulae, Y' and Y" are each independently selected from the group consisting of hydrogen, halogen, —CN, —$NO_2$, —OH, —$OR^4$, —$C(O)R^4$, —$CO_2R^4$, —$SR^4$, —$SOR^4$, —$SO_2R^4$, unsubstituted or substituted $C_{1-4}$ alkyl, and unsubstituted or substituted $C_{1-4}$ haloalkyl, with the proviso that Y' and Y" cannot both be hydrogen simultaneously.

In one preferred embodiment, Y' and Y" are each independently hydrogen or halogen, with the proviso that one or both are halogen. More preferably, Y' is hydrogen and Y" is chloro; Y' and Y" are both fluoro; Y' is hydrogen and Y" is fluoro; or Y' is hydrogen and Y" is bromo. Most preferably, one halogen atom is para to the sulfonamide bond in formula (I).

In each of the above formulae, Z' and Z" are each independently selected from the group consisting of hydrogen, halogen, unsubstituted or substituted $C_{1-8}$ alkyl, unsubstituted or substituted $C_{3-8}$ cycloalkyl, unsubstituted or substituted $C_{2-8}$ alkenyl, unsubstituted or substituted $C_{2-8}$ alkynyl, unsubstituted or substituted $C_{1-8}$ alkoxy, =O, —CN, —$NO_2$, —OH, —$OR^7$, —$OC(O)R^7$, —$CO_2R^7$, —$C(O)R^7$, —$CONR^7R^8$, —$OC(O)NR^7R^8$, —$NR^7C(O)R^8$, —$NR^7C(O)NR^8R^9$, —$NR^7R^8$, —$NR^7CO_2R^8$, —$SR^7$, —$SOR^7$, —$SO_2R^7$, —$SO_2NR^7R^8$, —$NR^7SO_2R^8$, unsubstituted or substituted $C_{6-10}$ aryl, unsubstituted or substituted 5- or 6-membered heteroaryl and unsubstituted or substituted 3- to 7-membered heterocyclyl.

In one preferred embodiment, Z' and Z" are each independently selected from the group consisting of hydrogen, halogen, unsubstituted or substituted $C_{1-8}$ alkyl, unsubstituted or substituted $C_{3-8}$ cycloalkyl, —CN, —OH, —$OR^7$, —$C(O)R^7$, —$CO_2R^7$, —$OC(O)R^7$, —$CONR^7R^8$, —$NR^7R^8$, —$NR^7CO_2R^8$, —$SR^7$, —$SOR^7$, —$SO_2R^7$, —$NR^7SO_2R^8$, unsubstituted or substituted $C_{6-10}$ aryl, and unsubstituted or substituted 5- or 6-membered heterocyclyl.

In a more preferred embodiment, Z' and Z" are each independently hydrogen, halogen, —CN, —$OR^7$, —$NR^7R^8$, —$SR^7$ (e.g., thiomethyl), —$SOR^7$, and —$SO_2R^7$ (e.g., methylsulfonyl), unsubstituted or substituted $C_{1-6}$ alkoxyl (e.g., methoxy), unsubstituted or substituted $C_{1-6}$ alkyl (e.g., methyl), unsubstituted or substituted phenyl, or unsubstituted or substituted 5- or 6-membered heterocyclyl.

Compositions that Modulate CCR9 Activity

In another aspect, the present invention provides compositions that modulate CCR9 activity. Generally, the compositions for modulating chemokine receptor activity in humans and animals will comprise a pharmaceutically acceptable excipient or diluent and a compound having the formula provided above as formula (I).

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 20020012680, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients; for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non toxic parenterally acceptable diluent or solvent, for example as a solution in 1,3-butane diol. Among the acceptable vehicles and solvents that may be employed are water, Ringers solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered viaocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

Methods of Treating CCR9-mediated Conditions or Diseases

In yet another aspect, the present invention provides methods of treating or preventing a CCR9-mediated condition or disease by administering to a subject having such a condition or disease a therapeutically effective amount of any compound of formula (I) above. Compounds for use in the present methods include those compounds according to formula (I), those provided above as embodiments, those specifically exemplified in the Examples below, and those provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR9-mediated condition or disease" and related phrases and terms refer to a condition or disease characterized by inappropriate, i.e., less than or greater than normal, CCR9 functional activity. Inappropriate CCR9 functional activity might arise as the result of CCR9 expression in cells which normally do not express CCR9, increased CCR9 expression (leading to, e.g., inflammatory and immunoregulatory disorders and diseases) or decreased CCR9 expression. Inappropriate CCR9 functional activity might also arise as the result of TECK secretion by cells which normally do not secrete TECK, increased TECK expression (leading to, e.g., inflammatory and immunoregulatory disorders and diseases) or decreased TECK expression. A CCR9-mediated condition or disease may be completely or partially mediated by inappropriate CCR9 functional activity. However, a CCR9-mediated condition or disease is one in which modulation of CCR9 results in some effect on the underlying condition or disease (e.g., a CCR9 antagonist results in some improvement in patient well being in at least some patients).

The term "therapeutically effective amount" means the amount of the subject compound that will elicit the biological or medical response of a cell, tissue, system, or animal, such as a human, that is being sought by the researcher, veterinarian, medical doctor or other treatment provider.

Diseases and conditions associated with inflammation, immune disorders, infection and cancer can be treated or prevented with the present compounds, compositions, and methods. In one group of embodiments, diseases or conditions, including chronic diseases, of humans or other species can be treated with inhibitors of CCR9 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8)

asthma and respiratory allergic diseases such as allergic asthma, allergic rhinitis, hypersensitivity lung diseases and the like, (9) autoimmune diseases, such as fibromyalgia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (13) immune mediated food allergies such as Coeliac (Celiac) disease (14) pulmonary fibrosis and other fibrotic diseases, and (15) irritable bowel syndrome.

In another group of embodiments, diseases or conditions can be treated with modulators and agonists of CCR9 function. Examples of diseases to be treated by modulating CCR9 function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is means to include bone marrow transplant conditions and solid organ (e.g., kidney, liver, lung, heart, pancreas or combination thereof) transplant conditions.

Preferably, the present methods are directed to the treatment of diseases or conditions selected from inflammatory bowel disease including Crohn's disease and Ulcerative Colitis, allergic diseases, psoriasis, atopic dermatitis and asthma, autoimmune disease such as rheumatoid arthritis and immune-mediated food allergies such as Coelaic disease.

Depending on the disease to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non toxic pharmaceutically acceptable carriers, adjuvants and vehicles appropriate for each rouse of administration. The present invention also contemplates administration of the compounds and compositions of the present invention in a depot formulation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In still other embodiments, the present methods are directed to the treatment of allergic diseases, wherein a compound or composition of the invention is administered either alone or in combination with a second therapeutic agent, wherein said second therapeutic agent is an antihistamine. When used in combination, the practitioner can administer a combination of the compound or composition of the present invention and a second therapeutic agent. Also, the compound or composition and the second therapeutic agent can be administered sequentially, in any order.

In yet other embodiments, the present methods are directed to the treatment of psoriasis wherein a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a β2-agonist and a corticosteroid.

The compounds and compositions of the present invention can be combined with other compounds and compositions having related utilities to prevent and treat the condition or disease of interest, such as inflammatory conditions and diseases, including inflammatory bowel disease, allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

EXAMPLES

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

Compounds within the scope of this invention can be synthesized as described below, using a variety of reactions known to the skilled artisan. A sample of useful routes to both the benzophenone and heteroaryl derived subunits and to fully elaborated sulfonamide molecules of formula (I) within this claim are provided below. In the descriptions of the syntheses that follow, some precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

Compounds of the invention can be prepared using conventional synthetic methodology. Examples of approaches that may be taken to synthesize these compounds are shown below. Nonetheless, one skilled in the art will recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are within the scope of the invention.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Preparation of CCR9 Modulators

The following examples are offered to illustrate, but not to limit, the claimed invention.

Additionally, those skilled in the art will recognize that the molecules claimed in this patent may be synthesized using a variety of standard organic chemistry transformations.

Certain general reaction types employed widely to synthesize target compounds in this invention are summarized in, the examples. Specifically, generic procedures for sulfonamide formation, pyridine N-oxide formation and 2-aminophenyl-arylmethanone synthesis via Friedel-Crafts type approaches are given, but numerous other standard chemistries are described within and were employed routinely.

While not intended to be exhaustive, representative synthetic organic transformations which can be used to prepare compounds of the invention are included below.

These representative transformations include; standard functional group manipulations; reduction such as nitro to amino; oxidations of functional groups including alcohols and pyridines; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Buckvald, Suzuki and Sonigashira reactions; halogenations and other electrophilic aromatic substitution reactions; diazonium salt formations and reactions of these species; etherifications; cyclative condensations, dehydrations, oxidations and reductions leading to heteroaryl groups; aryl metallations and transmetallations and reaction of the ensuing aryl-metal species with an electrophile such as an acid chloride or Weinreb amide; amidations; esterifications; nucleophilic substitution reactions; alkylations; acylations; sulfonamide formation; chlorosulfonylations; ester and related hydrolyses, and the like.

Example 1

General Procedure for the Preparation of N-Aryl-benzenesulfonamides

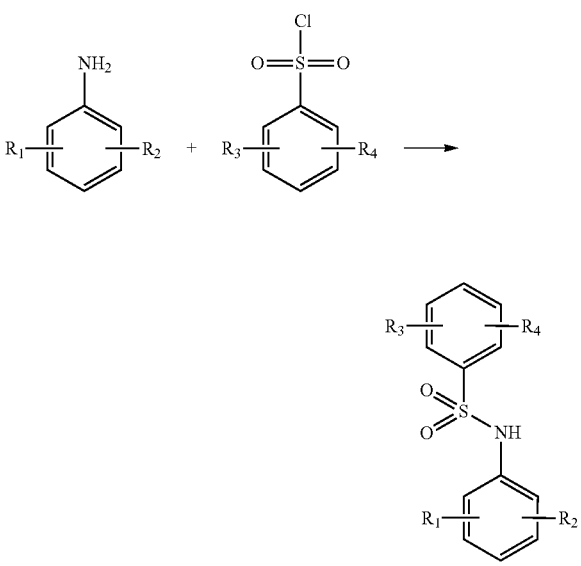

To the desired aniline (0.5 mmol) dissolved in pyridine and cooled in an ice-water bath was added a solution of an aryl sulfonyl chloride (0.5 mmol) dissolved in cold pyridine. The reaction mixture was then heated to 60° C. with gentle shaking for 16 h. Evaporation of the solvent with standard workup followed by either flash chromatography or reversed phase HPLC yielded the corresponding N-aryl-benzenesulfonamides.

Example 2

General Procedure for the Synthesis of (2-Amino-phenyl)-pyridinyl-methanones

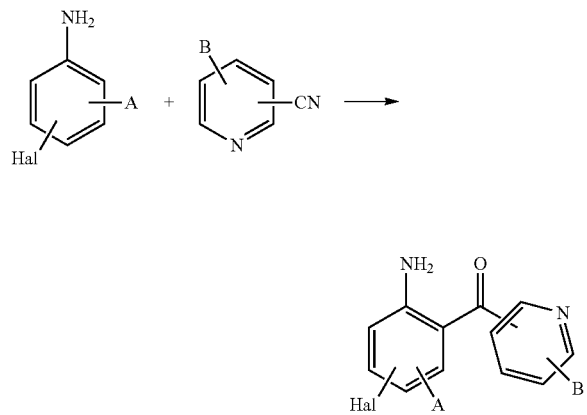

To 12.5 mL 1 M BCl$_3$ (12 mmol, 1.2 eq.) in methylene chloride stirred at 0° C. was added a solution of the desired haloaniline (10 mmol, 1.0 eq.) in 15 mL of TCE drop wise over 20 minutes. After 10 minutes the desired cyanopyridine (11 mmol, 1.1 eq.) was added followed by AlCl$_3$ (15 mmol, 1.5 eq.). The reaction was brought to RT, stirred for an hour then heated at 80-90° C. until all of the DCM was distilled off. The reaction mixture was then refluxed at 160° C. for 4 hours, cooled to RT and stirred overnight. 10 mL 3 M HCl were carefully added and the mixture was refluxed at 120° C. for 2-3 hours while reaction progress was monitored by LC/MS. The crude reaction was cooled to RT and 100 mL water were added. The crude mixture was extracted with DCM (2×50 mL), the aqueous layer was set aside and the organic layer was back extracted with 50 mL 1 M HCl (aq.). All aqueous layers were combined, brought to pH 12 with 3 M NaOH (aq.) and extracted with DCM (4×50 mL). The DCM layer was dried on Na$_2$SO$_4$, filtered and concentrated by rotary evaporation. The crude product was washed liberally with Et$_2$O and dried under vacuum, and further purified by conventional techniques such as column chromatography when necessary.

Example 3

General Procedure for the Synthesis of Sulfonamide Pyridine-N-Oxides

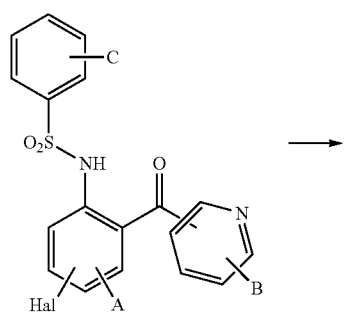

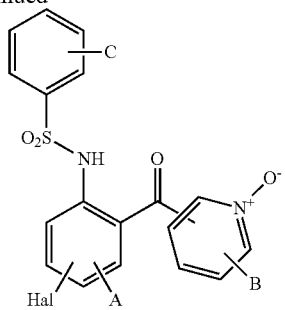

The desired N-Aryl-benzenesulfonamide (250 μmol) was dissolved in 2 mL DCM and m-CPBA (1.0-1.5 eq) was then added. The reaction was shaken at RT and monitored by LC-MS. Additional m-CPBA was added as needed in aliquots until the reaction was complete. In most cases the reaction required 15-24 h rxn time. Standard workup led to the isolation of crude products, which were purified by column chromatography.

Example 4

Synthesis of (2-Amino-5-chloro-phenyl)-pyridin-4-yl-methanone

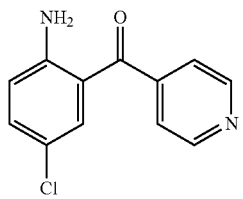

A solution of 4-chloroaniline (2.0 g, 16 mmol) in 30 mL of TCE was added drop wise to a solution of BCl$_3$ (1M in DCM) (24 ml, 24 mmol) with ice bath cooling, over a period of 15 min and the reaction mixture stirred at that temperature for an additional 10 min. 4-Cyanopyridine (2.0 g, 19 mmol) and AlCl$_3$ (3.0 g, 22 mmol) were added with ice-water cooling. The solution was allowed to warm to room temperature and stirred for 30 min. The resulting solution was refluxed at 160° C. for 4 h and stirred at room temperature overnight. The reaction mixture was then treated with 30 mL of 3N HCl and the mixture was refluxed at 110° C. for 1.5 h. The reaction mixture was allowed to cool down to room temperature and the solution was adjusted to pH12 with 6N NaOH and then diluted water and DCM. The resulting two layers were separated and the aqueous layer was extracted with DCM three times and the organic layers combined and dried over sodium sulfate. After removal of the solvent, the resulting solid was washed with ether to yield (2-amino-5-chloro-phenyl)-pyridin-4-yl-methanone (2.8 g, 75%).

Example 5

Synthesis of (2-Amino-5-chloro-phenyl)-(6-methyl-pyridin-2-yl)methanone

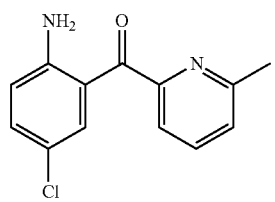

To 20 mL 1M BCl3 (20 mmol, 2.3 eq.) in DCM stirred at 0° C. was added a solution of 1.1 g 4-chloroaniline (8.6 mmol, 1.0 eq.) in 15 mL of TCE drop wise over five minutes. After 10 minutes 1.1 g of 2-cyano-6-methylpyridine (1.1 eq.) were added to the reaction mixture and after 2 minutes 1.6 g AlCl₃ (12 mmol, 1.4 eq.) was added. After 5 minutes the reaction was brought to RT, stirred for an hour then heated at 160° C. for 17 hours. 100 mL 3M HCl were added and the reaction is monitored by LC/MS. After 6 hours the reaction was removed from heat, cooled to RT and 300 mL water were added. The crude mixture was extracted with DCM (1×500 mL), the aqueous layer was set aside and the organic layer was back extracted with 300 mL 3M HCl (aq.). All aqueous layers were combined, brought to pH 11 with 3M NaOH (aq.) and extracted with DCM. The DCM layer was dried on Na₂SO₄, filtered and concentrated by rotary evaporation. Preparatory chromatography afforded the product as a cream colored solid which was converted to its HCl salt before being characterized. ¹H NMR: δ (ppm): 2.83 (s, 3H), 7.32 (d, J=2.0 Hz, 1H), 7.34 (d, J=1.6 Hz, 1H), 7.49 (d, J=7.6 Hz, 1H), 7.82-7.85 (m, 2H), 7.99 (t, J=7.6 Hz, H), 8.27 (d, J=7.6 Hz, 1H), 10.83 (s, 1H). MS: (M+H)/z=247.0

Example 6

Synthesis of (5-chloro-2-nitro-phenyl)-(6-chloro-pyridin-3-yl)-methanol

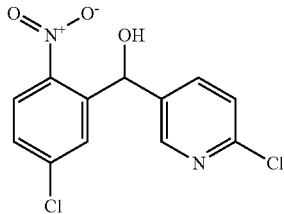

A solution of 1.0 g 2-chloro-5-iodopyridine (4.1 mmol, 1.0 eq.) in 10 mL anhyd. THF was stirred at −40° C. to −50° C. After five minutes, 2.2 mL of 2.1 M ⁱPrMgBr/THF (4.6 mmol, 1.1 eq.) were added drop wise over 1 minute and the reaction mixture is maintained at −40 to −50° C. for 30 minutes. 1.3 g 2-nitro-5-chlorobenzaldehyde (7.0 mmol, 1.7 eq.) was then added and the reaction was maintained at −50° C. After 1 hour, the reaction was allowed to warm to −10° C., and quenched with 50 mL saturated brine after a further fifteen minutes. The crude product was extracted with EtOAc, dried on Na₂SO₄ and concentrated by rotary evaporation to yield desired product. MS: (M+H)/z=298.9

Example 7

Synthesis of (5-Chloro-2-nitro-phenyl)-(6-chloro-pyridin-3-yl)-methanone

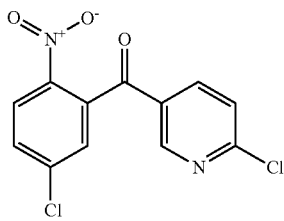

To (5-Chloro-2-nitro-phenyl)-(6-chloro-pyridin-3-yl)-methanol was added an excess (ca. 2 eq.) of PDC in DCM. The suspension was shaken at room temperature overnight. The reaction was monitored by LC-MS, another 1-2 eq. of PDC was added and the reaction was shaken for another 6 hours. The crude product was filtered through Celite and purified by flash chromatography (silica gel, DCM). ¹H NMR (CDCl₃): δ (ppm): 7.50 (d, J=2.4 Hz, 1H), 7.79 (d, J=8.0 Hz, 1H), 7.68 & 7.70 (dd, J=8.8 Hz, 2.0 Hz, 1H), 8.09-8.11 (m, 1 H), 8.24 (d, J=8.8 Hz, 1 H), 8.57 (d, J=2.0 Hz, 1 H. MS: (M+H)/z=296.9

Example 8

Synthesis of (2-Amino-5-chloro-phenyl)-(6-chloro-pyridin-3-yl)-methanone

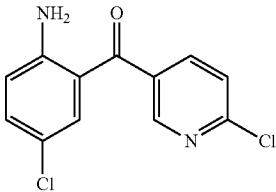

3-(5-chloro-2-nitrophenyl)-pyridinylmethanone was added to a mixture of concentrated HCl, DMF, SnCl₂ and heated at 130° C. The reaction was monitored by LC/MS and removed from heat after 2 h. The crude reaction was treated with aq. K₂CO₃, extracted into DCM and concentrated by rotary evaporation. The crude product was purified by preparatory chromatography. MS: (M+H)/z=267.0

Example 9

Synthesis of N-(4-Chloro-phenyl)-2,2-dimethyl-propionamide

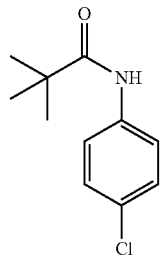

To a solution of 4-chloroaniline (5.0 g, 39.2 mmol) in 25 mL pyridine was added 5.3 mL (43.1 mmol) of pivaloyl chloride and the reaction mixture stirred overnight at room temperature. The mixture was poured into vigorously stirring 6M HCl, and the solids were collected by vacuum filtration, washed well with H₂O, and dried in vacuo to yield the title compound. 1H NMR (CDCl3) δ 7.47 (d, J=9.2 Hz, 2H) 7.30 (s, 1H) 7.27 (d, J=8.8 Hz, 2H) 1.32 (s, 9H) MS (ES) m/z=212.1

Example 10

Synthesis of N-[4-chloro-2-(hydroxy-pyridin-3-yl-methyl)-phenyl]-2,2-dimethyl-propionamide

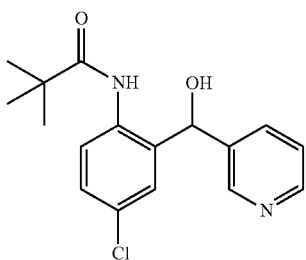

N-(4-Chloro-phenyl)-2,2-dimethyl-propionamide (3.0, 14.2 mmol) was dissolved in 15 mL THF in a dry 100 mL flask fitted with a rubber septa and nitrogen inlet and cooled to 0° C. in ice water bath for 25 minutes. A solution of 2.5M BuLi in hexane (17.0 mL, 42.6 mmol) was added and the mixture stirred for 45 minutes. To the thick yellow precipitate that formed was added a solution of pyridine-3-carboxaldehyde (3.03 g, 28.4 mmol) in 15 mL THF. The ice bath was removed and the mixture was allowed to stir at room temperature for 45 minutes and the reaction was quenched with 25 mL $H_2O$. The mixture was transferred to a separating funnel, and the aqueous phase was discarded. The organics were dried in vacuo to yield product as an orange oil. 1H NMR (CDCl3) δ 8.85 (m, 1H) 8.54 (m, 1H) 8.42 (m, 1H) 8.10 (dd, J=8.8 Hz, 2.8 Hz, 1H) 7.50 (d, J=8.0 Hz, 1H) 7.31 (m, 1H) 7.23 (m, 1H) 7.10 (m, 1H) 5.85 (m, 1H) 1.70 (d, 1H) 1.08 (s, 9H); MS (ES) m/z=319.1 (MH)+

Example 11

Synthesis of N-[4-chloro-2-(pyridine-3-carbonyl)-phenyl]-2,2-dimethyl-propionamide

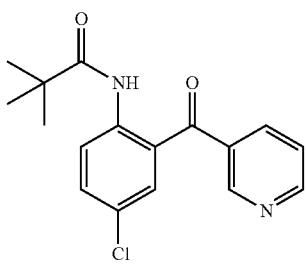

N-[4-chloro-2-(hydroxy-pyridin-3-yl-methyl)-phenyl]-2,2-dimethyl-propionamide (1.0 g, 3.14 mmol) was dissolved in 5 mL pyridine and treated with $CrO_3$ (0.75 g, 7.5 mmol, 2.39 eq). The mixture was stirred under $N_2$ at room temperature for five hours, diluted with 20 mL 1:2 EtOAc/$H_2O$, and filtered through Celite. The aqueous phase was separated and discarded, then the organics dried under vacuum yielding product (680 mg, 70%). 1H NMR (CDCl3) δ 11.06 (s, 1H) 8.92 (d, J=2.4 Hz, 1H) 8.84 (d, J=8.0 Hz, 1H) 8.73 (d, J=9.2 Hz, 1H) 8.00 (d, J=8.0 Hz, 1H) 7.56 (dd, J=11.2 Hz, 2.0 Hz, 1H) 7.48 (m, 2H) 1.36 (s, 9H) MS (ES) m/z=317.1 (MH)+

Example 12

Synthesis of (2-amino-5-chloro-phenyl)-pyridin-3-yl-methanone

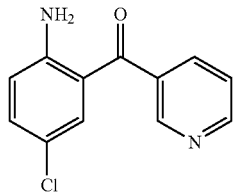

N-[4-chloro-2-(pyridine-3-carbonyl)-phenyl]-2,2-dimethyl-propionamide (0.65 g) was suspended in 5 mL of 70% $H_2SO_4$ and heated at 95° C. in oil bath overnight. After cooling to room temperature the solution was added drop wise with stirring to 20 mL of 40% NaOH solution placed in an ice-water bath. The fine yellow precipitate formed was collected by vacuum filtration, washed well with water and dried under vacuum to give 370 mg of product. 1H NMR (CDCl3) δ 8.84 (dd, J=2.4 Hz, 0.8 Hz, 1H) 8.77 (dd, J=4.8 Hz, 2.0 Hz, 1H) 7.93 (dt, J=8.4 Hz, 2.0 Hz, 1H) 7.43 (m, 1H) 7.35 (d, J=2.0 Hz, 1H) 7.25 (d, J=0.8 Hz, 1H) 6.71 (d, J=8.8 Hz, 1H) 6.21 (s, 2H) MS (ES) m/z=233.0 (MH)+

Example 13

Synthesis of 2-methyl-isonicotinonitrile

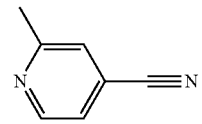

Dimethyl sulfate (18.3 mL, 192.4 mmol) was added to stirring 2-picoline-N-oxide (20 g) over a 10 minute period. The reaction was exothermic and the material quickly became homogeneous. The mixture was heated in a 60° C. oil bath for 2 hours, then the volatiles were removed under vacuum and the pale yellow oil was diluted with 25 mL $H_2O$ and added drop wise over 10 minutes to 160 mL of 25% (w/v) KCN/$H_2O$. After stirring for 3.5 hours the yellow precipitate formed was collected by vacuum filtration and purified by column chromatography (EtOAc/Hexane) to yield 13.0 g of product (60%). 1H NMR (CDCl3) δ 8.66 (d, J=4.8 Hz, 1H) 7.37 (s, 1H) 7.31 (d, J=4.4 Hz, 1H) 2.62 (s, 3H) 2.62 (s, 3H); MS (ES) m/z=119.0

Example 14

Synthesis of (2-amino-5-chloro-phenyl)-(2-methyl-pyridin-4-yl)-methanone

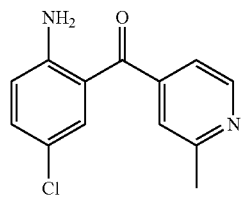

The title compound was prepared according to the general procedure for the Synthesis of (2-Amino-phenyl)-aryl-methanones, using 4-chloro-phenylamine (1.8 g, 14.2 mmol) and 2-methyl-isonicotinonitrile (2.0 g, 16.9 mmol). 1H NMR (CDCl3) δ 8.64 (d, J=4.8 Hz, 1H) 7.28 (m, 3H) 7.20 (d, J=6.0 Hz, 1H) 6.70 (d, J=12.4 Hz, 1H) 6.28 (s, 2H) 2.66 (s, 3H) MS (ES) m/z=247.0

Example 15

Synthesis of (2-amino-5-chloro-phenyl)-pyridin-2-yl-methanone

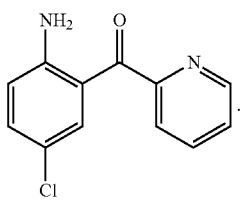

To a solution of 2-bromopyridine (5 ml, 52 mmol) in Et$_2$O (60 ml) was added 40 ml of a n-butyllithium (1.6M in hexane, 64 mmol) drop wise at −40° C. over 30 min under a nitrogen atmosphere. The resulting yellow solution was stirred for a further 1 hr at −50° C. to −30° C. In a separate flask, a solution of 2-amino-5-chlorobenzoic acid (2.05 g, 12 mmol) in dry THF (90 ml), under nitrogen atmosphere and with ice-cooling, was added in one portion to the solution prepared as described above. The reaction mixture was stirred for 2 hrs at 0° C. and then chlorotrimethylsilane (30 ml) was added at 0° C. with stirring. The reaction mixture was allowed to warm to room temperature and 1 N HCl aq (100 ml) was added. The resulting two-phase system was separated. The aqueous phase was adjusted to pH12 with 6N NaOH solution and extracted with ethyl acetate (2×150 ml). The combined organic extractions were dried over Na$_2$SO$_4$. After removal of solvent, the residue was purified by the flash chromatography using ethyl acetate/hexane (1:4) as eluent. Crystallization of the product from Et$_2$O/hexane mixture gave 1.26 g (45%) of desired product as yellow solid. $^1$H-NMR (DMSO-d$_6$, 500 MHz): δ 6.90 (1H, d, J=9 Hz), 7.31 (1H, dd, J=9 and 2.5 Hz), 7.40 (2H, br), 7.53 (1H, d, J=2.5 Hz), 7.61 (1H, m), 7.79 (1H, d, J=8 Hz), 8.03 (1H, m), 8.69 (1H, m). MS: (ESI$^+$): 233.2 (M+1).

Example 16

Synthesis of (2-Amino-5-chloro-phenyl)-(3-methyl-pyridin-4-yl)-methanone

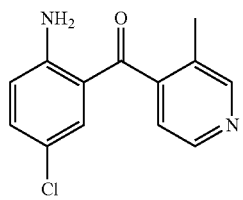

To a solution of 3-picoline (50 g, 0.48 mol) in glacial acetic acid (150 ml) was added hydrogen peroxide (25 ml) at RT. The mixture was heated to 90° C. for 3 hr. The mixture was cooled to RT and more hydrogen peroxide (18.5 ml) was added slowly. The mixture was again heated to 90° C. for 19 hr. The excess peroxide was carefully decomposed using Pd—C (2.5 g) at 0° C. Pd—C was removed by filtration, and the filtrate was concentrated and crude 3-methylpyridine-1-oxide was purified by fractional distillation in vacuo.

A solution of 3-methylpyridine-1-oxide (10 g, 0.092 mol) in methyl iodide (15 ml) was left at it for 18 hr and the solid was filtered. The filtrate was diluted with diethyl ether and extracted with water (40 ml). The solid was re-dissolved in the aqueous extract, 1,4-dioxane (50 ml) was added, followed by potassium cyanide (15 g, 0.23 mol) and the mixture was stirred at RT for 3 hr. The product was extracted with chloroform. The chloroform layer was washed with water, brine and dried over sodium sulfate. The solvent was removed in vacuo and the crude product was purified by fractional distillation (61-62° C./0.2 mm) to yield a white low melting solid.

BCl$_3$ (24 ml, 1M in DCM, 0.024 mol) was added slowly to a solution of 4-chloroaniline (2 g, 0.016 mol) in 30 ml of trichloroethylene over a period of 15 min. at 0° C. and stirred at this temperature for an additional 10 min. 4-Cyano-3-methylpyridine (2.2 g, 0.019 mol) and AlCl$_3$ (3 g, 0.022 mol) were added at 0° C. The solution was allowed to warm to RT and stirred for 30 min. The solution was then heated at 80-90° C. for 1 hr. and the DCM was distilled off. The resulting solution was refluxed at 115° C. for 4 hr and stirred at RT overnight. 3N HCl (20 ml) was added and the mixture refluxed at 100° C. for 2 hr. The reaction mixture was cooled to 0° C. and adjusted to pH-12 with 6N NaOH. The reaction mixture was extracted with DCM, and the DCM layer washed with water, brine and dried over Na$_2$SO$_4$. The solvent was removed, and the crude was purified by column chromatography over silica gel to yield a yellow solid.

Example 17

Synthesis of (2-Amino-4,5-difluoro-phenyl)-pyridin-4-yl-methanone

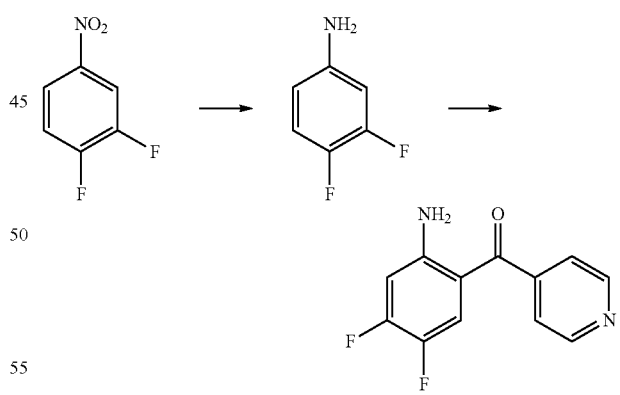

Iron powder (28.1 g, 0.502 mol) was added as small portions to 1,2-difluoro nitrobenzene (20.0 g, 0.126 mol) in methanol (200 ml) and heated to 60° C. Ammonium chloride (48.4 g, 0.91 mol) in water (100 ml) was added drop wise and the reaction mixture refluxed for 5 hr. The reaction mixture was filtered over Celite and washed with methanol. Methanol was removed, and the aqueous layer was extracted with ethylacetate, washed with brine, dried over sodium sulphate and concentrated to yield 1,2-difluoro-4-aminobenzene (7 g, 43%).

BCl₃ (6.2 ml, 1M in DCM) was added drop wise to 1,2-difluoro-4-aminobenzene (0.5 g, 0.004 mol) in trichloroethylene (6.5 ml) at 0° C. and this mixture stirred for 15 min. 4-Cyanopyridine (0.48 g, 0.005 mol) was added and the solution was warmed to RT and stirred for 30 min. The solution was then heated at 80-90° C. for 1 h. The resulting solution was refluxed at 160° C. for 4 hr and stirred at RT over night. 3N HCl was added to the reaction mixture and refluxed at 110° C. for 1.5 h. The reaction mixture was cooled to RT and made basic (pH=12) with 6N NaOH. The reaction mixture was diluted with water and DCM. The resulting two layers were separated and the aqueous layer was extracted with DCM, dried over sodium sulphate and concentrated. The compound was purified by column chromatography using silica gel to yield title compound (0.25 g, 27%).

Example 18

Synthesis of (6-Amino-2,3-difluoro-phenyl)-pyridin-4-yl-methanone

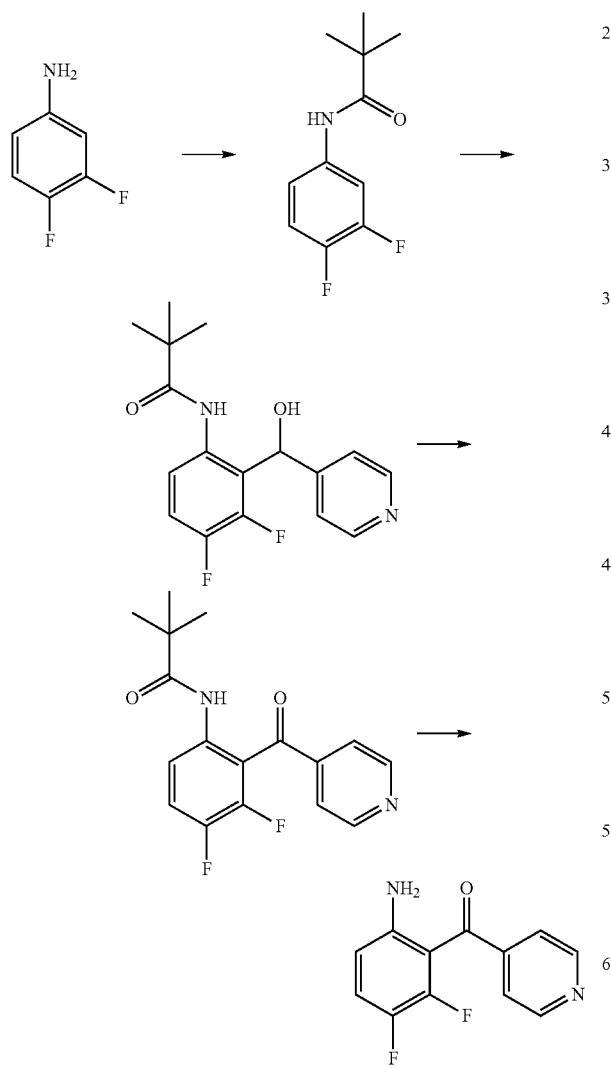

To 3,4-Difluoroaniline (2.0 g, 0.0153 mol) and triethylamine (3.1 g, 0.0307 mol) in dry benzene (100 ml) was added trimethylacetylchloride (2.3 g, 0.0184 mol) slowly at 0° C. and the reaction mixture stirred at RT overnight. The reaction mixture was then quenched with water and extracted with ethyl acetate. The organic layer was washed with water, brine, dried over sodium sulfate and concentrated. Compound was recrystallized from petroleum ether yielding 3.2 g, 98%.

This protected 3,4-difluoroaniline (2.7 g, 0.0126 mol) was taken in dry THF (25 ml) and under nitrogen t-butyllithium (2.02 g, 0.032 mol) was added drop wise at −78° C. Stirring was continued at −78° C. for 2 h. 4-Pyridine carboxaldehyde (3.55 g, 0.033 mol) dissolved in dry THF (10 ml) was added slowly. The reaction mixture was warmed to room temperature and stirred over night. The reaction mixture was then quenched with water and extracted with ether. The organic layer was washed with brine, dried over sodium sulfate and concentrated. Compound was purified by column chromatography to yield carbinol (2.6 g, 65%).

To carbinol (2.6 g, 0.0031 mol) in 17.3 ml of pyridine was added a suspension of chromium trioxide (0.705 g, 0.007 mol) in pyridine (6.0 ml) under a nitrogen atmosphere. The resulting mixture was allowed to stir at RT over night. The reaction mixture was poured into water and extracted with ether. The ether extract was washed with brine, dried over sodium sulfate and concentrated. The compound was purified by column chromatography to yield the protected precursor to the title compound (1.7 g, 65.8%).

To this pivaloyl protected amino ketone (1.7 g, 0.0053 mol) was added 70% sulfuric acid (14.6 ml) and the reaction mixture heated to 95-100° C. overnight. The reaction mixture was basified by using 10% sodium hydroxide and extracted with dichloromethane. The organic layer was washed with water, brine, dried over sodium sulfate and concentrated. The product obtained was purified by column chromatography to yield title compound (0.58 g, 46.4%).

Example 19

Synthesis of (2-Amino-5-chloro-4-methoxy-phenyl)-pyridin-4-yl-methanone

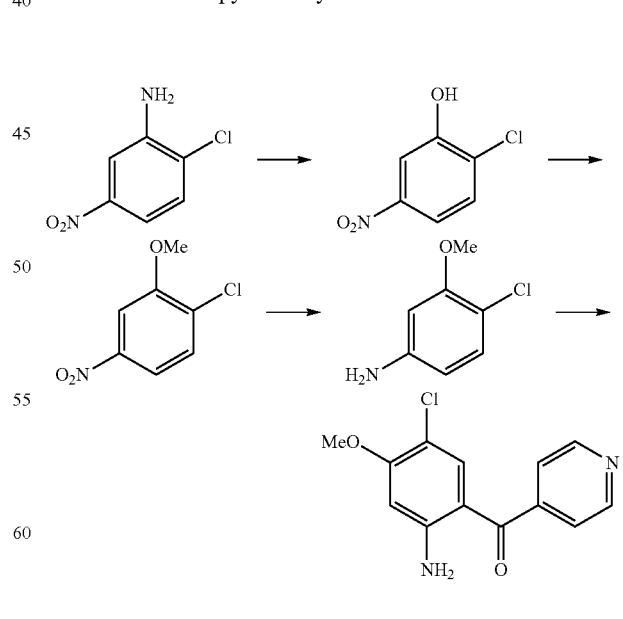

5-Nitro-2-chloro aniline (50.0 g, 0.289 mol) in 30% sulfuric acid (300 ml) was stirred at RT for 2 h. Sodium nitrite (21.0 g, 0.304 mol) in water (50 ml) was added slowly at 0° C. After 15 mins, this solution was added slowly to dilute sulfuric acid (50%, 250 ml) at 110° C. Stirring was continued for 15 min. The reaction mixture was cooled to RT, ice water was added, extracted with ethylacetate, washed with water, brine and dried over Na$_2$SO$_4$. The phenol product obtained upon concentration was purified by column chromatography. Yield 12.0 g, 24.0%.

K$_2$CO$_3$ (23.84 g, 0.172 mol) was added to 2-chloro-5-nitrophenol (10.0 g, 0.058 mol) in acetonitrile (100 ml) at RT. After cooling to 0° C., methyl iodide (19.6 g, 0.138 mol) was added slowly and the reaction mixture stirred at RT overnight. Water (100 ml) was added and the aqueous layer extracted with ethyl acetate. The organic layer was washed with water, brine and dried over Na$_2$SO$_4$. The product obtained upon concentration was purified by column chromatography to yield the anisole (6.0 g, 55.55%).

2-Chloro-5-nitro anisole (6.0 g, 0.032 mol) in MeOH (45 ml) was added slowly to stannous chloride (15.1 g, 0.08 mol) in conc. HCl (110 ml) at 40° C. and the temperature was slowly raised to 50° C. Stirring was continued for 2 h. After cooling to RT, the reaction mixture was basified with 50% NaOH solution, extracted by ethyl acetate, washed with water, then brine and dried over Na$_2$SO$_4$. 3-Methoxy-4-chloroaniline was obtained upon concentration and was purified further by column chromatography. Yield: 4.0 g, 79.36%.

To 3-Methoxy-4-chloroaniline (2.0 g, 0.0126 mol) in trichloroethylene (30 ml) was added BCl$_3$ (2.18 g, 1 M solution in DCM, 0.0188 mol) at 0° C. After stirring for 10 min, 4-cyanopyridine (1.6 g, 0.0153 mol) and AlCl$_3$ (2.35 g, 0.018 mol) were added and the temperature was raised to RT, with further stirring for 30 min. The temperature was raised further to 85° C. and maintained at the same temperature for 1 h. DCM was distilled off and the solution was stirred at 115° C. for 4 h and then at RT over night. 3N HCl was added at RT and the reaction mixture refluxed for 1.5 h. The reaction mixture was allowed to cool and made basic using NaOH (6 N), diluted with water and extracted with DCM, washed with water, brine and dried over Na$_2$SO$_4$. The crude title compound was obtained upon concentration and was purified by column chromatography. Yield: 0.50 g, 15%.

Example 20

Synthesis of (2-Amino-5-chloro-phenyl)-pyrimidin-4-yl-methanone

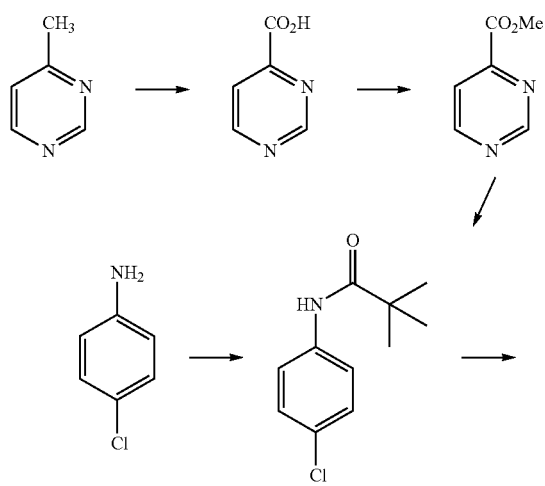

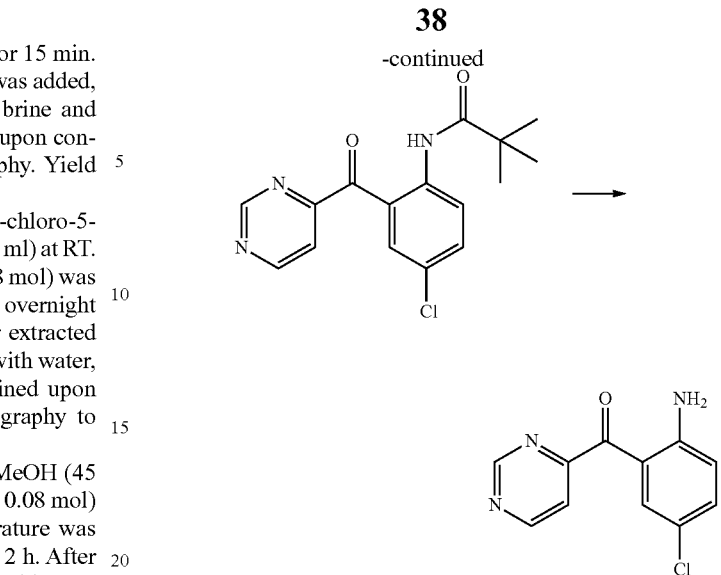

To 4-Methyl pyrimidine (5.0 g, 0.053 mol) in pyridine (55 ml) was added selenium dioxide (8.82 g, 0.079 mol) at RT with stirring. The reaction mixture was stirred at 55° C. for 2 h and at 80° C. for 3.5 hr. After cooling to RT and stirring over night, the reaction mixture was filtered and the residue was washed with pyridine. The combined pyridine solution was concentrated and the carboxylic acid obtained was washed with water to remove traces of selenium dioxide. Yield: 5.3 g, 80.5%.

To Pyrimidine-4-carboxylic acid (5.0 g, 0.04 mol) in methanol (170 ml) was added conc. HCl (2 ml) at RT. After refluxing overnight, the reaction mixture was cooled to RT and neutralized with 10% sodium bicarbonate solution and concentrated. The ester was extracted with diethyl ether, dried over Na$_2$SO$_4$ and concentrated to get the methyl ester as a yellow solid, yield: 3.3 g, 57.55%.

Trimethyl acetylchloride (11.30 g, 0.093 mol) was added to a benzene (500 ml) solution of triethylamine (15.75 g, 0.155 mol) and 4-chloroaniline (10.0 g, 0.078 mol) at 0° C. The reaction mixture was warmed to RT and stirred for 3 h. The reaction mixture was then quenched with water, extracted with ethyl acetate, washed with water, brine solution and dried over Na$_2$SO$_4$. The solid product obtained was crystallized from pet ether. Yield: 14.0 g, 84.43%.

To N-(4-chlorophenyl)-2,2-dimethyl propanamide (3.5 g, 0.0165 mol) in THF (50 ml) at 0° C. was added n-butyl lithium in hexane (2.64 g, 1.2 M, 0.041 mol). Stirring was continued at 0° C. for 2 h, the reaction then cooled to −70° C., pyrimidine-4-methyl carboxylate (3.18 g, 0.023 mol) in THF (25 ml) was then added slowly and the solution was warmed to RT and stirred overnight. Diethyl ether (50 ml) and water (50 ml) were added and the organic layer was separated. The aqueous layer was further extracted with ether. The combined ether layers were washed with water, brine and dried over Na$_2$SO$_4$. The product obtained upon concentration was purified by column chromatography. Yield: 1.7 g, 32.69%.

The protected amino ketone (1.7 g, 0.0054 mol) in sulfuric acid (10 ml, 70%) was heated at 95° C. over night. The reaction mixture was cooled to RT and basified with 10% NaOH, extracted with DCM, washed with water, brine and dried over Na$_2$SO$_4$. The product obtained upon concentration was purified by column chromatography using basic alumina to yield title compound (0.20 g, 16%).

Example 21

Synthesis of (6-Amino-3-chloro-2-methoxy-phenyl)-pyridin-4-yl-methanone

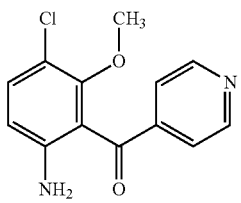

5-Nitro-2-chloro aniline (50.0 g, 0.289 mol) in 30% sulfuric acid (300 ml) was stirred at RT for 2 h. Sodium nitrite (21.0 g, 0.304 mol) in water (50 ml) was added slowly at 0° C. and maintained at this temperature for 15 min. This diazotized solution was added slowly to dilute sulfuric acid (50%, 250 ml) at 110° C. Stirring was continued for 15 min. After cooling to RT, ice water was added, the mixture extracted with ethylacetate, washed with water, brine and dried over Na$_2$SO$_4$. The product obtained upon concentration was purified by column chromatography. Yield 12.0 g, 24.0%.

To K$_2$CO$_3$ (23.84 g, 0.172 mol) and 2-chloro-5-nitrophenol (10.0 g, 0.0576 mol) in acetonitrile (100 ml) was added methyl iodide (19.60 g, 0.138 mol) at 0° C. The reaction mixture was warmed to RT and stirred overnight. Water was added and extracted with ethyl acetate. The organic layer was washed with water, brine and dried over Na$_2$SO$_4$. The product obtained upon concentration was purified by column chromatography. Yield: 6.0 g, 55.55%.

2-Chloro-5-nitro anisole (6.0 g, 0.032 mol) in MeOH (45 ml) was added slowly to stannous chloride (15.1 g, 0.08 mol) in conc. HCl (110 ml) at 40° C. and the temperature was slowly raised to 50° C. Stirring was continued for 2 h, the reaction cooled to RT, basified with 50% NaOH solution and extracted by ethyl acetate. The organic layer was washed with water, brine and dried over Na$_2$SO$_4$. The product obtained upon concentration was purified by column chromatography. Yield: 4.0 g, 79.36%.

To triethylamine (3.83 g, 0.037 mol) and 3-methoxy-4-chloro aniline (3.0 g, 0.0190 mol) in benzene (50 ml) was added trimethylacetylchloride (2.75 g, 0.022 mol) slowly at 0° C. The temperature was raised to RT and stirred overnight. The reaction mixture was added to ice and extracted with ethyl acetate. The organic layer was washed with water, brine, dried over Na$_2$SO$_4$ and concentrated. Yield: 3.7 g, 80.43%.

To N-pivaloyl-3-methoxy-4-chloroaniline (1.50 g, 0.0062 mol) in THF (30 ml) was added n-butyl lithium (1.0 g, 0.0156 mol) at 0° C. and the reaction stirred for 2 hr. After cooling to −70° C., methyl isonicotinate (1.3 g, 0.0094 mol) in THF (12 ml) was added slowly. The reaction was warmed to rt and stirred overnight and then quenched with water and extracted with ether. The water layer was further extracted and the combined ether layers were washed with water, brine and dried over Na$_2$SO$_4$. The product obtained upon concentration was purified by column chromatography. Yield 0.50 g, 23.25%.

The protected ketone from step 5 (0.500 g, 0.0014 mol) was suspended in concentrated HCl (5 ml) at RT, then the temperature was raised to 95° C. and the mixture stirred overnight. The mixture was cooled to RT, basified with 20% NaOH solution and extracted with DCM. The combined organic layer was washed with water, brine and dried over Na$_2$SO$_4$. The product obtained upon concentration was purified by column chromatography using basic alumina to yield title compound (0.140 g, 37.33%).

Example 22

Synthesis of (2-Amino-5-chloro-phenyl)-(2-methyl-pyridin-4-yl)-methanone

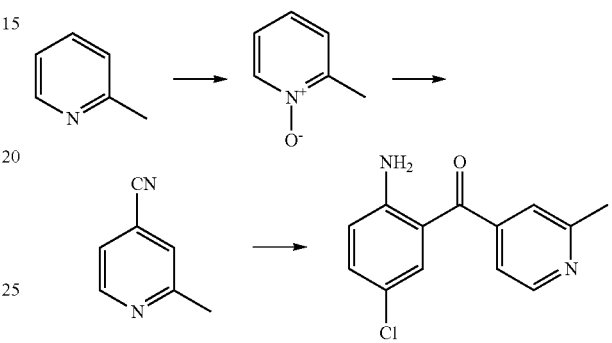

To a solution of 2-picoline (50 g, 0.48 mol) in glacial acetic acid (150 ml) was added hydrogen peroxide (25 ml) at RT. The mixture was heated to 90° C. for 3 hr. The mixture was cooled to RT and more hydrogen peroxide (18.5 ml) was added slowly. The mixture was again heated to 90° C. for 19 hr. The excess peroxide was cautiously decomposed using Pd—C (2.5 g) at 0° C. Pd—C was filtered, the filtrate was concentrated and the crude 2-methylpyridine-1-oxide was purified by fractional distillation under vacuum. Yield: 40 g, 69%.

A solution of 2-methylpyridine-1-oxide (10 g, 0.092 mol) in methyl iodide (15 ml) was stirred at RT for 18 hr. The solid was filtered. The filtrate was diluted with diethyl ether, extracted with water (40 ml). The solid was re-dissolved in the aqueous layer, 1,4-dioxane (50 ml) was added, followed by potassium cyanide (15 g, 0.23 mol). The mixture was stirred at RT for 3 hr. The product was extracted with chloroform. The chloroform layer was washed with water, brine and dried over sodium sulfate. The solvent was removed under vacuo and the crude material was purified by fractional distillation (61-62° C./0.2 mm) to yield a white low melting solid (6 g, 35%).

BCl$_3$ (24 ml, 1M in DCM, 0.024 mol) was added slowly to a solution of 4-chloroaniline (2 g, 0.016 mol) in 30 ml of trichloroethylene over a period of 15 min. at 0° C. and stirred at this temperature for an additional 10 min. 4-Cyano-2-methylpyridine (2.2 g, 0.019 mol) and AlCl$_3$ (3 g, 0.022 mol) were added at 0° C. The solution was warmed to RT and stirred for 30 min. The solution was then heated at 80-90° C. for 1 h and the DCM was distilled off. The resulting solution was refluxed at 115° C. for 4 hr and stirred at RT over night. 3N HCl (20 ml) was added to the mixture and refluxed at 100° C. for 2 hr. The reaction mixture was cooled to 0° C. and was made basic (pH-12) with 6N NaOH and the reaction mixture was extracted with DCM. The DCM layer was washed with water, brine and dried over Na$_2$SO$_4$. The solvent was removed, the crude was purified by column chromatography (silica gel) to yield title compound as yellow solid (1.55 g, 40%).

Example 23

Synthesis of (2-Amino-4-chloro-phenyl)-pyridin-4-yl-methanone

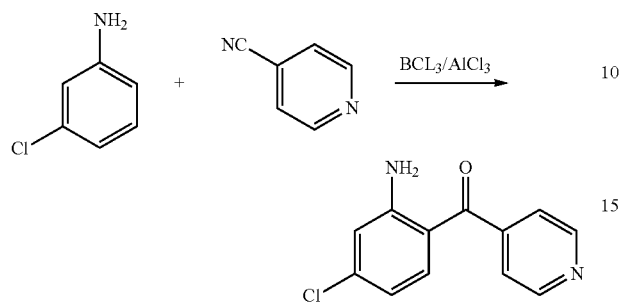

le;.2qTo BCl$_3$ (1M in DCM) (24 mL, 24 mmol), cooled to 0° C., a solution of 3-chloroaniline (2.0 g, 16 mmol) in 30 mL of TCE was added drop wise over a period of 15 min and the mixture stirred at that temperature for an additional 10 min. 4-cyanopyridine (2.0 g, 19 mmol) and AlCl$_3$ (3.0 g, 22 mmol) was added under ice-water cooling. The solution was allowed to warm to it and stirred for 30 min. The solution was then heated at 80-90° C. for 1 h and the DCM distilled off. The resulting solution was refluxed at 160° C. for 4 h and stirred at it overnight. 3N HCl (20 ml approx.) was added to the reaction mixture and then refluxed at 110° C. for 1.5 hr. The reaction mixture was cooled to rt and the solution was made basic (pH 12) with 6N NaOH. The reaction mixture was diluted with water and DCM. The resulting two layers were separated and the aqueous layer was extracted with DCM (3×150 mL), and dried (Na$_2$SO$_4$). After removal of solvent, the solid was washed with Et$_2$O to give 650 mg (24%) of desired product.

Example 24

Synthesis of (2-Amino-3-chloro-phenyl)-pyridin-4-yl-methanone

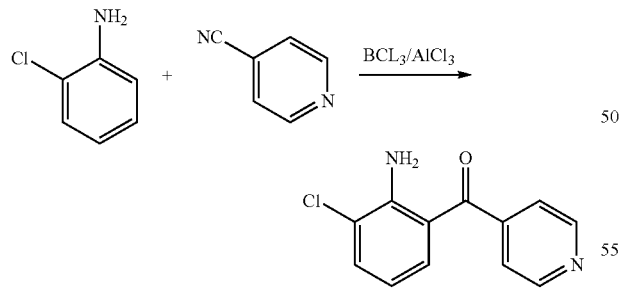

To a solution of BCl$_3$ (1M in DCM) (24 mL, 24 mmol), cooled to 0° C., was added a solution of 2-chloroaniline (2.0 g, 16 mmol) in 30 mL of TCE drop wise over a period of 15 min and the reaction stirred for an additional 10 min. 4-cyanopyridine (2.0 g, 19 mmol) and AlCl$_3$ (3.0 g, 22 mmol) were added under ice-water cooling. The solution was allowed to warm to it and stirred for 30 min. The solution was then heated at 80-90° C. for 1 h and the DCM distilled off. The resulting solution was refluxed at 160° C. for 4 h and stirred at it overnight. 3N HCl (20 ml approx.) was added to the reaction mixture and refluxed at 110° C. for 1.5 hr. The reaction mixture was cooled to rt and the solution was made basic (pH 12) with 6N NaOH. The reaction mixture was diluted with water and DCM. The resulting layers were separated and the aqueous layer was extracted with DCM (3×150 mL), and the combined organic layers dried (Na$_2$SO$_4$). After removal of solvent, the solid was washed with Et$_2$O to give 600 mg (21%) of desired product.

Example 25

Synthesis of (2-Amino-5-bromo-phenyl)-pyridin-4-yl-methanone

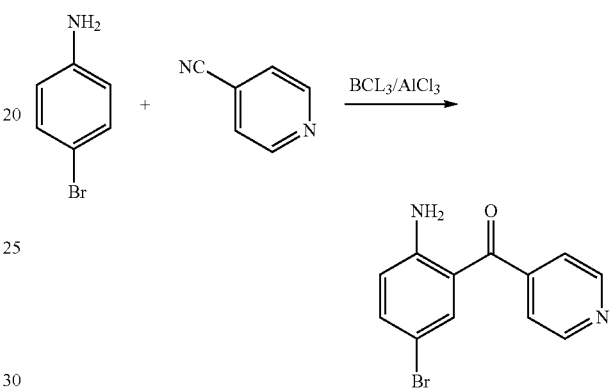

To a solution of BCl$_3$ (1M in DCM) (18 mL, 18 mmol), cooled to 0° C., was added drop wise over a period of 15 min a solution of 4-bromoaniline (2 g, 11.6 mmol) in 30 mL of TCE and the mixture stirred for an additional 10 min. 4-cyanopyridine (2.0 g, 19 mmol) and AlCl$_3$ (3.0 g, 22 mmol) were added under ice-water cooling. The solution was warmed to it and stirred for 30 min. The solution was then heated at 80-90° C. for 1 h and the DCM distilled off. The resulting solution was refluxed at 160° C. for 4 h and stirred at it overnight. 3N HCl (20 ml approx.) was added to the reaction mixture and refluxed at 110° C. for 1.5 hr. The reaction mixture was allowed to cool down and the solution was made basic (pH 12) with 6N NaOH. The reaction mixture was diluted with water and DCM. The resulting two layers were separated and the aqueous layer was extracted with DCM (3×150 mL), and the combined organic layers dried (Na$_2$SO$_4$). After removal of solvent, the solid was washed with Et$_2$O to give 1.050 g of desired product.

Example 26

Synthesis of (2-amino-5-fluoro-phenyl)-pyridin-4-yl-methanone

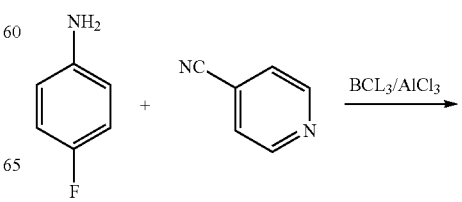

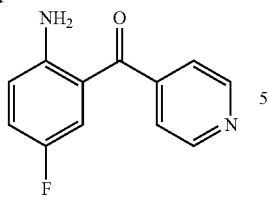

To a solution of BCl$_3$ (1M in DCM) (27 mL, 27 mmol), cooled to 0° C., was added drop wise over a period of 15 min a solution of 4-fluoroaniline (2.0 g, 18 mmol) in 30 mL of TCE and the mixture stirred at that temperature for an additional 10 min. 4-cyanopyridine (2.6 g, 25 mmol) and AlCl$_3$ (3.0 g, 22 mmol) were added under ice-water cooling. The solution was allowed to warm to it and then stirred for 30 min. The solution was then heated at 80-90° C. for 1 h and the DCM distilled off. The resulting solution was refluxed at 160° C. for 4 h and stirred at it overnight. 3N HCl (20 ml approx.) was added to the reaction mixture and refluxed at 110° C. for 1.5 hr. The reaction mixture was allowed to cool down and the solution was made basic (pH 12) with 6N NaOH. The reaction mixture was diluted with water and DCM. The resulting two layers were separated and the aqueous layer was extracted with DCM (3×150 mL), and the combined organic layers dried (Na$_2$SO$_4$). After removal of solvent, the solid was washed with Et$_2$O to give 1.05 g (27%) of desired product.

Example 27

Synthesis of (2-Amino-5-chloro-phenyl)-(1-methyl-1H-imidazol-2-yl)-methanone

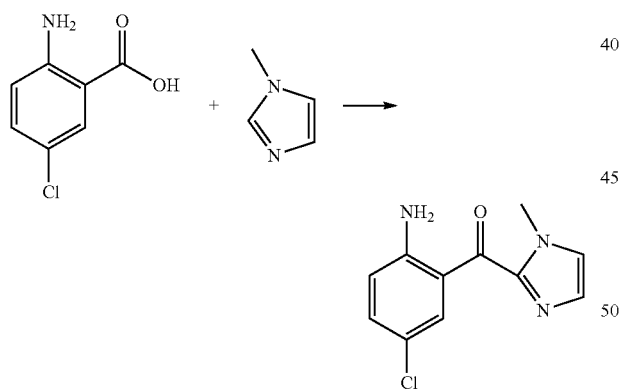

To a solution of "BuLi (0.0730 mol) in hexane was added N-methyl imidazole (0.0608 mol) drop wise at −40° C. over 30 min under a nitrogen atmosphere. The resulting yellow solution was stirred for a further 3 hr at rt, and then refluxed for 1 h. 2-amino-5-chlorobenzoic acid (1.74 g, 0.01014 mole) in dry ether (60 ml) was then added to the reaction mixture. The reaction mixture was stirred overnight at rt. To the reaction mixture was added saturated NH$_4$Cl solution and the resulting mixture extracted with ethyl acetate (2×150 ml). The combined organic layers were dried over Na$_2$SO$_4$. After removal of solvent, the residue was purified by the flash chromatography using ethyl acetate/hexane (1:4) as eluent. Crystallization of the product from Et$_2$O/hexane mixture gave 300 mg (13.7%) of product as yellow solid.

Example 28

Synthesis of (2-Amino-5-chloro-phenyl)-(2-methyl-pyridin-3-yl methanone

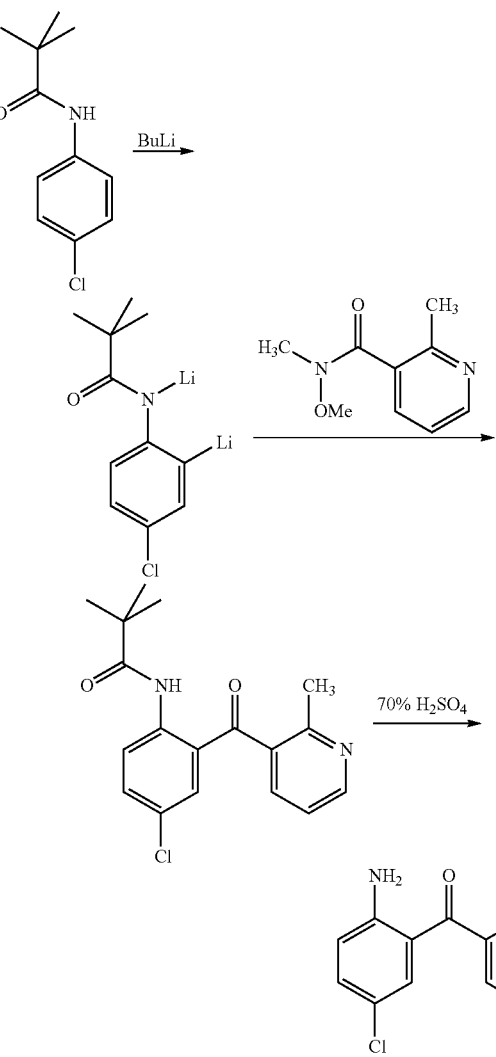

Trimethylacetyl chloride (35 g) was added drop wise to a solution of 4-chloroaniline (31.9 g) in dry pyridine and the reaction was stirred under nitrogen overnight. About half of the pyridine was removed by rotary evaporation, then the mixture was treated with 6M hydrochloric acid and extracted with ethyl acetate. The extracts were washed with saturated aqueous NaHCO$_3$ and with water, then were dried (MgSO$_4$), filtered and concentrated by rotary evaporation. The resulting crystalline product was vacuum filtered and dried at high vacuum to constant weight, resulting in a good yield of N-(4-chloro-phenyl)-2,2-dimethyl-propionamide as fine needles. EDC (10 g) and 2-methyl-nicotinic acid (7.15 g) were magnetically stirred in acetonitrile-THF with N,O-dimethylhydroxylamine hydrochloride (9.75 g) and triethylamine (25 mL). After stirring overnight at ambient temperature, the resulting white suspension was added to ice water and extracted with ethyl acetate (3×100 mL). The extracts were dried, filtered, and concentrated to give a light amber oil.

To a magnetically stirred solution of N-(4-chloro-phenyl)-2,2-dimethyl-propionamide (3.16 g, 14.9 mmol) in dry THF was added 2.5M n-butyllithium in hexane at −40° C. and the mixture was stirred at 0° C. for 2 h and a suspension of white solid resulted. A solution of the Weinreb amide (1.80 g, 10.0 mmol) in dry THF was added drop wise and the reaction was stirred at ambient temp overnight. The mixture was diluted with water and extracted with ethyl acetate and the organic layer was dried (MgSO4), filtered and concentrated. Chromatography on silica gel (20-30% EtOAc/Hexane) provided the desired N-[4-Chloro-2-(2-methyl-pyridine-3-carbonyl)-phenyl]-2,2-dimethyl-propionamide as a waxy bright yellow solid (2.28 g, 6.89 mmol): $^1$H NMR (CDCl3) δ 11.71 (s, 1H, NH), 8.82 (d, 1H, J=9.2 Hz), 8.67 (dd, 1H, J=4.8 Hz, J=1.8 Hz), 7.55 (m, 2H), 7.28 (d, 1H, J=2.5 Hz), 7.25 (m, 1H), 2.54 (s, 3H), 1.39 (s, 9H).

The N-[4-chloro-2-(2-methyl-pyridine-3-carbonyl)-phenyl]-2,2-dimethyl-propionamide intermediate (2.28 g, 6.89 mmol) was magnetically stirred with 70% sulfuric acid and heated at 75° C. and progress of the solvolysis was monitored by LC/MS. The reaction was allowed to cool to ambient temperature, and was washed with ether-hexane to remove oily by-products. The acidic aqueous layer was cooled in an ice bath and aqueous NaOH was added drop wise to basify the mixture. The product was extracted with ethyl acetate and the extracts were washed with saturated aqueous NaHCO3 (2×100 mL), with saturated aqueous sodium chloride, dried (MgSO4), filtered and concentrated. The bright yellow product crystallized on standing: $^1$H NMR (CDCl3) δ 8.54 (dd, 1H, J=5.2 Hz, J=1.6 Hz), 7.45 (dd, 1H, J=7.6 Hz, J=1.5 Hz), 7.15 (m, 2H), 7.00 (d, 1H, J=2.6 Hz), 6.61 (d, 1H, J=9.1 Hz), 6.39 (br s, 2H), 2.42 (s, 3H).

Example 29

Synthesis of (2-Amino-5-chloro-phenyl)-(6-methyl-pyridin-3-yl)-methanone

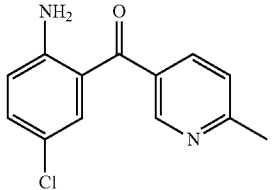

The title compound was prepared using procedures described above for the synthesis of 2-amino-5-chloro-phenyl)-(2-methyl-pyridin-3-yl)-methanone.

Example 30

Synthesis of N-[4-Chloro-2-(pyridine-4-carbonyl)-phenyl]-4-oxazol-5-yl-benzenesulfonamide

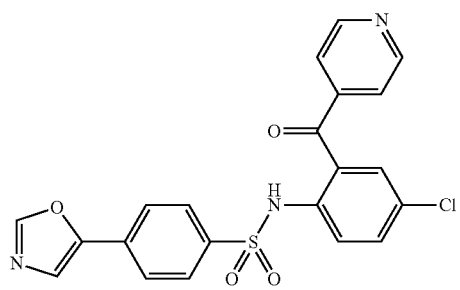

The title compound was prepared according to the general procedure for the synthesis of N-Aryl-benzenesulfonamides previously described using 116 mg of (2-Amino-5-chloro-phenyl)-pyridin-4-yl-methanone and 122 mg 4-oxazol-5-yl-benzenesulfonyl chloride. Purification by purification by reversed phase HPLC gave pure product. $^1$H-NMR (400 MHz, CDCl$_3$): δ 7.21 (dd, H, J=1.5, 4.4 Hz), 7.30 (d, 1H, J=2.5 Hz), 7.42 (s, 1H), 7.54 (dd, 1H, J=2.5, 8.8 Hz), 7.61 (d, 2H, J=8.4 Hz), 7.77 (s, 1H), 7.78 (d, 2H, J=8.4 Hz), 7.95 (s, 1H), 8.69 (d, 2H, J=5.8 Hz), 10.06 (br, 1H). MS: m/z 440.9 (M$^+$+1).

Example 31

Synthesis of 4-tert-Butyl-N-[4-chloro-2-(pyridine-4-carbonyl)-phenyl]-benzenesulfonamide

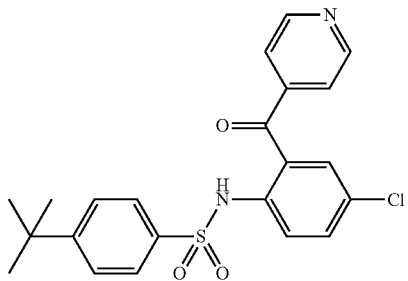

The title compound was prepared according to the general procedure for the synthesis of N-Aryl-benzenesulfonamides previously described using 116 mg of (2-Amino-5-chloro-phenyl)-pyridin-4-yl-methanone and 116 mg of 4-tert-Butyl-benzenesulfonyl chloride. $^1$H-NMR (400 MHz, CDCl$_3$): δ 1.25 (s, 9H), 7.02 (d, 1H, J=8.4 Hz), 7.44 (m, 3H), 7.66 (d, 2H, J=8.4), 7.79 (d, 1H, J=2.4 Hz), 8.11 (d, 2H, J=6.4), 8.88 d, 2H, J=6.0 Hz), 10.51 (s, 1H). MS: m/z 429.9 (M$^+$+1).

Example 32

Synthesis of 4-tert-Butyl-N-[4-chloro-2-(1-oxy-pyridine-4-carbonyl)-phenyl]-benzenesulfonamide

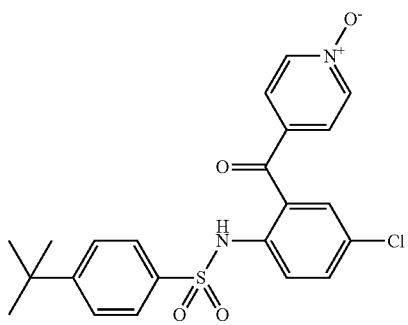

4-tert-Butyl-N-[4-chloro-2-(pyridine-4-carbonyl)-phenyl]-benzenesulfonamide (107 mg, 0.25 mmol) was dissolved in 4 mL DCM and m-chloroperoxybenzoic (0.26 mmol) was added. The mixture was stirred at room temperature for 16 h. The solvent was evaporated on a rotary evaporator and the product was purified by reversed phase HPLC to yield title compound. $^1$H-NMR (400 MHz, CDCl$_3$): δ 1.24 (s, 9H), 7.32-7.4 (m, 5H), 7.52 (dd, 1H, J=8.8, Hz, 2.4 Hz), 7.63 (d, 2H, J=8.8 Hz), 7.74 (d, 1H, J=8.8 Hz), 8.18 (d, 2H, J=7.6 Hz), 9.60 (s, 1H). MS: m/z 445.9 (M$^+$+1).

Example 33

Synthesis of N-[4-Chloro-2-(pyridine-2-carbonyl)-phenyl]-4-methoxy-benzenesulfonamide

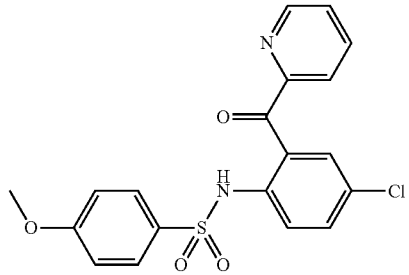

The title compound was prepared according to the general procedure for the synthesis of N-Aryl-benzenesulfonamides previously described using 116 mg of (2-Amino-5-chloro-phenyl)-pyridin-2-yl-methanone and 101 mg of 4-methoxy-benzenesulfonyl chloride. $^1$H-NMR (400 MHz, CDCl$_3$): δ 3.75 (s, 3H), 6.76 (m, 2H, 7.45 (m, 2H), 7.63 (m, 2H), 7.71 (d, 1H, J=8.8 Hz), 7.78 (m, 1H), 7.88 (m, 2H), 8.64 (m, 1H), 10.24 (s, 1H). MS: m/z 403.9 (M$^+$+1).

Example 34

Synthesis of N-[4-Chloro-2-(pyridine-4-carbonyl)-phenyl]-4-methoxy-benzenesulfonamide

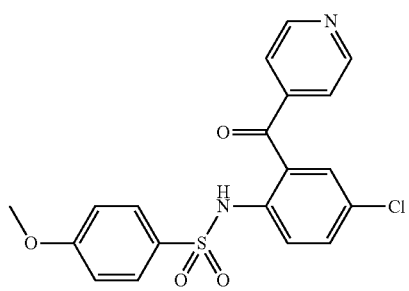

The title compound was prepared according to the general procedure for the synthesis of N-Aryl-benzenesulfonamides previously described using 116 mg of (2-Amino-5-chloro-phenyl)-pyridin-4-yl-methanone and 101 mg of 4-methoxy-benzenesulfonyl chloride. $^1$H-NMR (400 MHz, CDCl$_3$): δ 3.74 (s, 3H), 6.77 (d, 2H, J=8.8 Hz), 7.21 (m, 2H), 7.27 (d, 1H, J=2 Hz), 7.52 (dd, 1H, J=8.8 Hz, 2.8 Hz), 7.63 (m, 2H), 7.76 (d, 1H, J=8.8 Hz), 8.76 (d, 2H, J=5.6 Hz), 9.88 (s, 1H). MS: m/z 403.9 (M$^+$+1).

Example 35

Synthesis of N-[4-Bromo-2-(pyridine-4-carbonyl)-phenyl]-4-methoxy-benzenesulfonamide

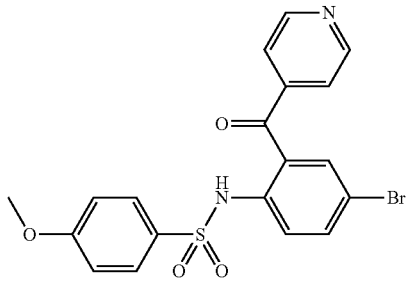

The title compound was prepared according to the general procedure for the synthesis of N-Aryl-benzenesulfonamides previously described using 138 mg of (2-amino-5-bromo-phenyl)-pyridin-4-yl-methanone and 101 mg of 4-methoxy-benzenesulfonyl chloride. $^1$H-NMR (400 MHz, CDCl$_3$): δ 3.69 (s, 3H), 6.68 (d, 2H, J=8.8 Hz), 7.36-7.47 (m, 4H), 7.46, 7.55-7.69 (m, 5H), 9.65 (s, 1H). MS: m/z 448.3 (M$^+$+1).

Example 36

Synthesis of 4-tert-Butyl-N-[4-fluoro-2-(pyridine-4-carbonyl)-phenyl]-benzenesulfonamide

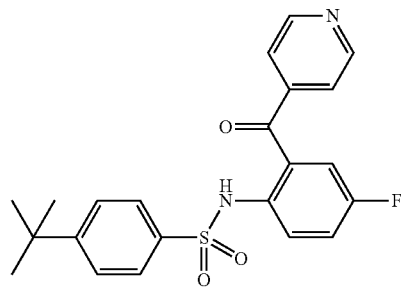

The title compound was prepared according to the general procedure for the synthesis of N-Aryl-benzenesulfonamides previously described using 108 mg of (2-Amino-5-fluoro-phenyl)-pyridin-4-yl-methanone and 116 mg of 4-tert-butyl-benzenesulfonyl chloride. $^1$H-NMR (400 MHz, CDCl$_3$): δ 1.25 (s, 9H), 6.98 (dd, 1H, J=8.8 Hz, 3.2 Hz), 7.30-7.38 (m, 3H), 7.43 (m, 2H), 7.62 (m, 2H), 7.80 (dd, 1H, 9.2 Hz, 4.8 Hz), 8.82 (d, 2H, 4.8 Hz), 9.82 (s, 1H). MS: m/z 413.5 (M$^+$+1).

Example 37

Synthesis of N-[4-Bromo-2-(pyridine-4-carbonyl)-phenyl]-4-tert-butyl-benzenesulfonamide

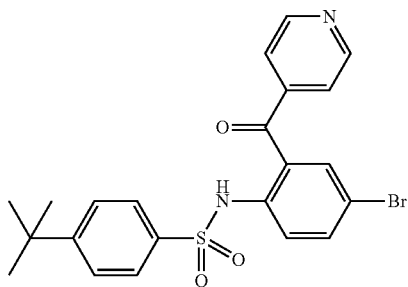

The title compound was prepared according to the general procedure for the synthesis of N-Aryl-benzenesulfonamides previously described using 138 mg of (2-Amino-5-bromo-phenyl)-pyridin-4-yl-methanone and 116 mg of 4-tert-butyl-benzenesulfonyl chloride. $^1$H-NMR (400 MHz, CDCl$_3$): δ 1.27 (3, 9H), 7.41 (m, 3H), 7.50 (dd, 2H, J=4.8 Hz, 1.6 Hz), 7.67-72 (m, 4H), 8.85 (d, 2H, J=6 Hz), 10.19 (s, 1H). MS: m/z 473.9 (M$^+$+1).

Example 38

Synthesis of 4-tert-Butyl-N-[5-chloro-2-(pyridine-4-carbonyl)-phenyl]-benzenesulfonamide

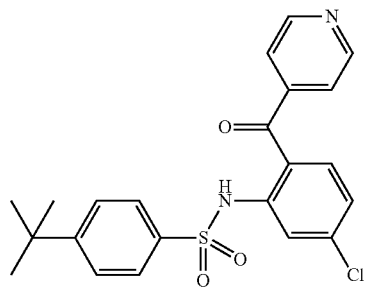

The title compound was prepared according to the general procedure for the synthesis of N-Aryl-benzenesulfonamides previously described using 116 mg of (2-amino-4-chloro-phenyl)-pyridin-4-yl-methanone and 116 mg of 4-tert-butyl-benzenesulfonyl chloride. $^1$H-NMR (400 MHz, CDCl$_3$): δ 1.30 (s, 9H), 7.04 (d, 1H, J=8.4 Hz), 7.25 (d, 1H, J=8.4 Hz), 7.45-7.52 (m, 4H), 7.74 (dd, 2H, J=8.8 Hz, 1.6 Hz), 7.52 (dd, 2H, J=4.4 Hz, 1.6 Hz), 7.78 (m, 2H), 7.84 (d, 1.6 Hz), 8.84 (d, 2H, J=5.6 Hz), 10.61 (s, 1H). MS: m/z 429.0 (M$^+$+1).

Example 39

Synthesis of N-[4-Bromo-2-(pyridine-4-carbonyl)-phenyl]-4-trifluoromethoxy-benzenesulfonamide

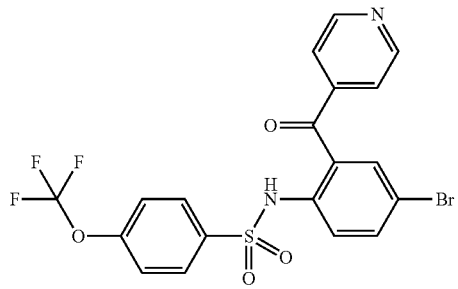

The title compound was prepared according to the general procedure for the synthesis of N-Aryl-benzenesulfonamides previously described using 138 mg of (2-Amino-5-bromo-phenyl)-pyridin-4-yl-methanone and 130 mg of 4-trifluoromethoxy-benzenesulfonyl chloride. $^1$H-NMR (400 MHz, CDCl$_3$): δ 7.21 (d, 2H, J=8.8 Hz), 7.35 (m, 2H), 7.45 (s, 1H), 7.70 (m, 2H), 7.83 (m, 2H), 8.82 (dd, 2H, J=4.8 Hz, 1.6 Hz), 10.21 (s, 1H). MS: m/z 502.3 (M$^+$+1).

Example 40

Synthesis of 4-Bromo-N-[4-chloro-2-(pyridine-4-carbonyl)-phenyl]-benzenesulfonamide

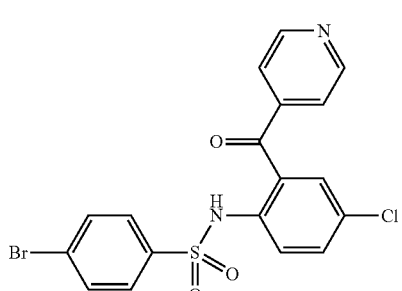

The title compound was prepared according to the general procedure for the synthesis of N-Aryl-benzenesulfonamides previously described using 116 mg of (2-amino-5-chloro-phenyl)-pyridin-4-yl-methanone and 122 mg of 4-bromo-benzenesulfonyl chloride. $^1$H-NMR (400 MHz, CDCl$_3$): δ

7.21 (d, 1H, J=2.4 Hz), 7.49-7.61 (m, 5H), 7.73 (d, 1H, J=8.8 Hz), 8.86 (dd, 2H, J=4.4 Hz, 1.2 Hz), 10.00 (s, 1H). MS: m/z 451.9 (M⁺+1)

Example 41

Synthesis of N-[4-Chloro-2-(pyridine-4-carbonyl)-phenyl]-3-cyano-benzenesulfonamide

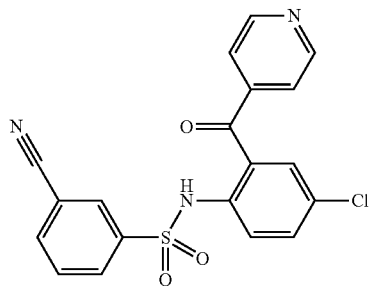

The title compound was prepared according to the general procedure for the synthesis of N-Aryl-benzenesulfonamides previously described using 116 mg of (2-amino-5-chloro-phenyl)-pyridin-4-yl-methanone and 100 mg of 3-cyano-benzenesulfonyl chloride. ¹H-NMR (400 MHz, CDCl₃): δ 7.36 (d, 1H, J=2.4 Hz), 7.57-7.62 (m, 4H), 7.68 (d, 1H, J=8.8 Hz), 7.80 (m, 1H), 8.04 (m, 2H), 8.90 (dd, 2H, J=4.8 Hz, 1.6 Hz), 10.3 (b, 1H). MS: m/z 398.8 (M⁺+1).

Example 42

Synthesis of N-[4-Chloro-2-(pyridine-4-carbonyl)-phenyl]-4-methanesulfonyl-benzenesulfonamide

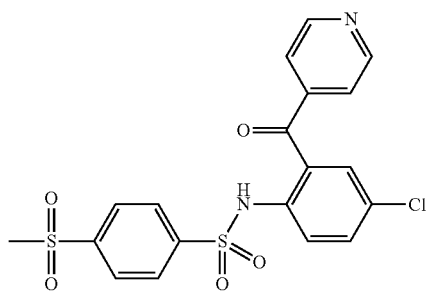

The title compound was prepared according to the general procedure for the synthesis of N-Aryl-benzenesulfonamides previously described using 116 mg of (2-amino-5-chloro-phenyl)-pyridin-4-yl-methanone and 127 mg of 4-methane-sulfonyl-benzenesulfonyl chloride. ¹H-NMR (400 MHz, CDCl₃): δ 3.06 (s, 3H), 7.31 (d, 1H, J=2.0 Hz), 7.45 (m, 2H), 7.58 (dd, 1H, J=8.8 Hz, 2.8 Hz), 7.99 (b, 4H), 8.88 (dd, 2H, J=4.8 Hz, 1.6 Hz), 10.29 (b, 1H). MS: m/z 451.9 (M⁺+1).

Example 43

Synthesis of 4-tert-Butyl-N-[4-chloro-2-(pyrimidine-4-carbonyl)-phenyl]-benzenesulfonamide

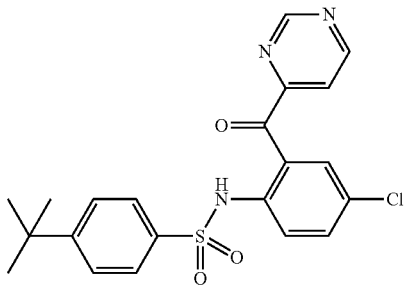

The title compound was prepared according to the general procedure for the synthesis of N-Aryl-benzenesulfonamides previously described using 116 mg of (2-Amino-5-chloro-phenyl)-pyrimidin-4-yl-methanone and 116 mg of 4-tert-butyl-benzenesulfonyl chloride. ¹H-NMR (400 MHz, CDCl₃): δ 1.23 (s, 9H), 7.40 (d, 2H, J=8.4 Hz), 7.51 (dd, 1H, J=8.8 Hz, 2 Hz), 7.71-7.80 (m, 6H), 9.03 (d, 1H, J=4.8 Hz), 9.33 (d, 1.2 Hz), 10.91 (b, 1H). MS: m/z 434.0 (M⁴+1).

Example 44

Synthesis of Biphenyl-4-sulfonic acid [4-chloro-2-(pyridine-4-carbonyl)-phenyl]-amide

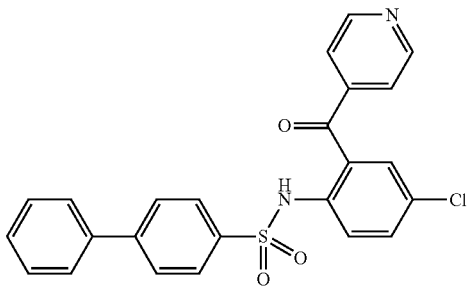

The title compound was prepared according to the general procedure for the synthesis of N-Aryl-benzenesulfonamides previously described using 116 mg of (2-amino-5-chloro-phenyl)-pyridin-4-yl-methanone and 126 mg of biphenyl-4-sulfonyl chloride. ¹H-NMR (400 MHz, CDCl₃): δ 7.24 (m, 1H), 7.36 (m, 2H), 7.42 (m, 5H), 7.56 (m, 3H), 7.77-7.84 (m, 3H), 8.73 (d, 2H, J=4.4 Hz), 10.01 (s, 1H). MS: m/z 449.0 (M⁺+1).

Example 45

Synthesis of 4-tert-Butyl-N-[4-chloro-2-(3-methyl-pyridine-4-carbonyl)-phenyl]-benzenesulfonamide

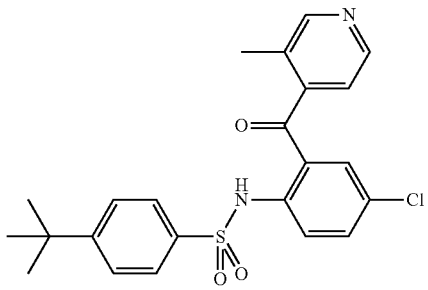

The title compound was prepared according to the general procedure for the synthesis of N-Aryl-benzenesulfonamides previously described using 123 mg of (2-Amino-5-chloro-phenyl)-(3-methyl-pyridin-4-yl)-methanone and 116 mg of 4-tert-butyl-benzenesulfonyl chloride. ¹H-NMR (400 MHz, CDCl₃): δ 1.32 (s, 9H), 2.19 (s, 3H), 7.04 (d, 1H, J=1.4 Hz), 7.21 (d, 1H, J=5.2 Hz), 7.48 (d, 2H, J=8.8 Hz), 7.52 (dd, 1H, J=8.8 Hz, 2.4 Hz), 7.77-7.83 (m, 3H), 8.64 (d, 1H, J=5.2 Hz), 8.71 (s, 1H), 10.75 (s, 1H). MS: m/z 443.0 (M⁺+1).

Example 46

Synthesis of N-[4-Chloro-2-(pyridine-4-carbonyl)-phenyl]-4-trifluoromethyl-benzenesulfonamide

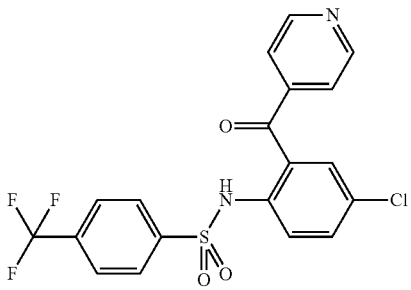

The title compound was prepared according to the general procedure for the synthesis of N-Aryl-benzenesulfonamides previously described using 116 mg of (2-amino-5-chloro-phenyl)-pyridin-4-yl-methanone and 122 mg of 4-Trifluoromethyl-benzenesulfonyl chloride. ¹H-NMR (400 MHz, CDCl₃): δ 7.31 (d, 1H, J=2.8 Hz), 7.36 (m, 2H), 7.54-7.59 (m, 2H), 7.73 (d, 1H, J=8.0 Hz), 7.77 (d, 1H, J=9.2 Hz), 7.97 (d, 1H, J=8.0 Hz), 8.00 (s, 1H), 8.82 (dd, 2H, J=6.0 Hz, 1.2 Hz), 10.16 (s, 1H). MS: m/z 441.8 (M⁺+1).

Example 47

Synthesis of 4-tert-Butyl-N-[4,5-difluoro-2-(pyridine-4-carbonyl)-phenyl]-benzenesulfonamide

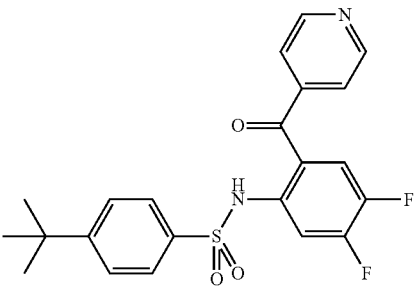

The title compound was prepared according to the general procedure for the synthesis of N-Aryl-benzenesulfonamides previously described using 117 mg of (2-Amino-4,5-difluoro-phenyl)-pyridin-4-yl-methanone and 116 mg of 4-tert-butyl-benzenesulfonyl chloride. ¹H-NMR (400 MHz, CDCl₃): δ 1.28 (s, 9H), 7.17 (t, 1H, J=8.4 Hz), 7.45 (d, 2H, J=8.4 Hz), 7.54 (d, 2H, J=4.4 Hz), 7.64 (dd, 1H, J=11.6 Hz, 6.8 Hz), 7.72 (d, 2H, J=8.4 Hz), 8.85 (d, 2H, J=5.2 Hz), 10.42 (s, 1H). MS: m/z 431.1 (M⁺+1).

Example 48

Synthesis of 4-tert-Butyl-N-[4-chloro-2-(6-morpholin-4-yl-pyridine-3-carbonyl)-phenyl]benzenesulfonamide

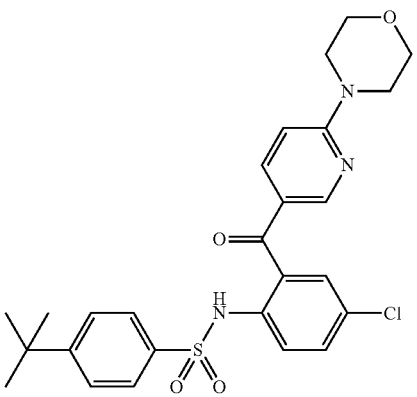

The title compound was prepared according to the general procedure for the synthesis of N-Aryl-benzenesulfonamides previously described using 158 mg of (2-Amino-5-chloro-phenyl)-(6-morpholin-4-yl-pyridin-3-yl)-methanone and 116 mg of 4-tert-butyl-benzenesulfonyl chloride. ¹H-NMR (400 MHz, CDCl₃): δ 1.22 (s, 3H), 3.76 (t, 4H, J=4.6 Hz), 3.857 (t, 4H, J=4.6H), 8.78 (d, 1H, J=9.2 Hz), 7.30 (m, 2H), 7.34 (m, 1H), 7.46 (m, 1H), 7.54-7.56 (m, 3H), 7.99 (d, 1H, J=9.2 Hz), 8.16 (v, 1H), 9.29 (s, 1H). MS: m/z 515.1 (M⁺+1).

Example 49

Synthesis of N-[4-Chloro-2-(6-methyl-pyridine-3-carbonyl)-phenyl]-4-oxazol-5-yl-benzenesulfonamide

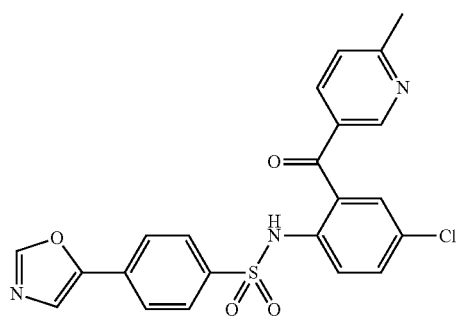

The title compound was prepared according to the general procedure for the synthesis of N-Aryl-benzenesulfonamides previously described using 123 mg of (2-Amino-5-chlorophenyl)-(6-methyl-pyridin-3-yl)-methanone and 122 mg of 4-oxazol-5-yl-benzenesulfonyl chloride. $^1$H-NMR (400 MHz, CDCl$_3$): δ 2.63 (s, 3H), 7.33 (m, 2H), 7.37 (s, 1H), 7.56 (m, 3H), 7.67-7.3 (m, 3H), 7.94 (m, 1H), 7.97 (s, 1H), 8.52 (b, 1H), 9.45 (s, 1H). MS: m/z 454.1 (M$^+$+1).

Example 50

Synthesis of 4-tert-Butyl-N-[4-chloro-2-(2-methyl-sulfanyl-pyridine-4-carbonyl)-phenyl]-benzenesulfonamide

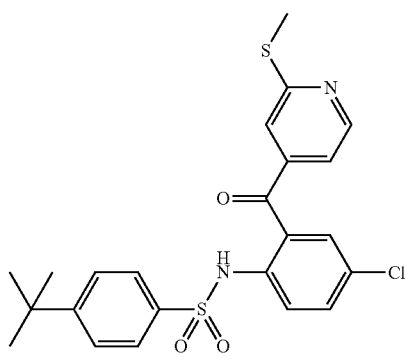

4-tert-Butyl-N-[4-chloro-2-(2-chloro-pyridine-4-carbonyl)-phenyl]-benzenesulfonamide (475 mg, 1.0 mmol) was dissolved in 10 mL dry THF and treated with solid sodium thiomethoxide (355 mg, 5 mmol) and the mixture heated at 70° C. for 16 h. The solvent was concentrated to about 2 mL and added to 5 mL cold 1M HCl. The light yellow solid precipitate was collected by filtration and product was purified by HPLC. $^1$H-NMR (400 MHz, CDCl$_3$): δ 1.26 (s, 9H), 2.61 (s, 3H), 6.86 (d, 1H, J=5.2 Hz), 7.18 (s, 1H), 7.28 (d, 1H, J=2.4 Hz), 7.39 (d, 2H, J=8.8 Hz), 7.51 (dd, 1H, J=8.8 Hz, 2.4 Hz), 7.67 (m, 2H), 7.76 (d, 1H, J=8.8 Hz), 8.56 (d, 1H, J=5.2 Hz), 10.13 (s, 1H). MS: m/z 476.1 (M$^+$+1).

Example 51

Synthesis of N-[4-Chloro-2-(2-methyl-pyridine-4-carbonyl)-phenyl]-4-oxazol-5-yl-benzenesulfonamide

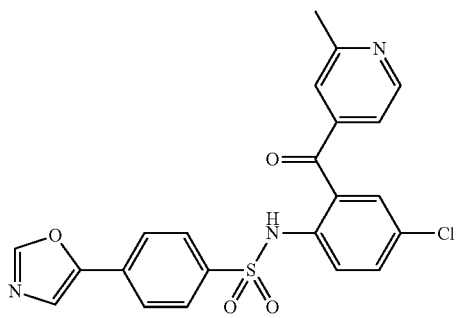

The title compound was prepared according to the general procedure for the synthesis of N-Aryl-benzenesulfonamides previously described using 123 mg of (2-Amino-5-chlorophenyl)-(2-methyl-pyridin-4-yl)-methanone and 122 mg of 4-oxazol-5-yl-benzenesulfonyl chloride. $^1$H-NMR (400 MHz, CDCl$_3$): δ 2.78 (s, 3H), 7.29 (d, 1H, J=2.8 Hz), 7.45 (m, 2H), 7.48 (s, 1H), 7.55 (dd, 1H, J=9.2 Hz, 2.8 Hz)), 7.67 (m, 3H), 7.83 (d, 2H, J=8.4 Hz), 8.03 (s, 1H), 8.81 (d, 1H, J=5.6 Hz), 10.10 (s, 1H). MS: m/z 454.9 (M$^+$+1).

Example 52

Synthesis of N-[4-Chloro-2-(1-oxy-pyridine-4-carbonyl)-phenyl]-4-(2-hydroxy-1,1-dimethyl-ethyl)-benzenesulfonamide

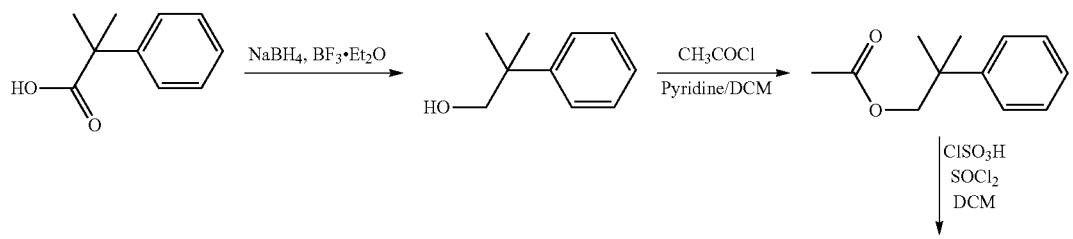

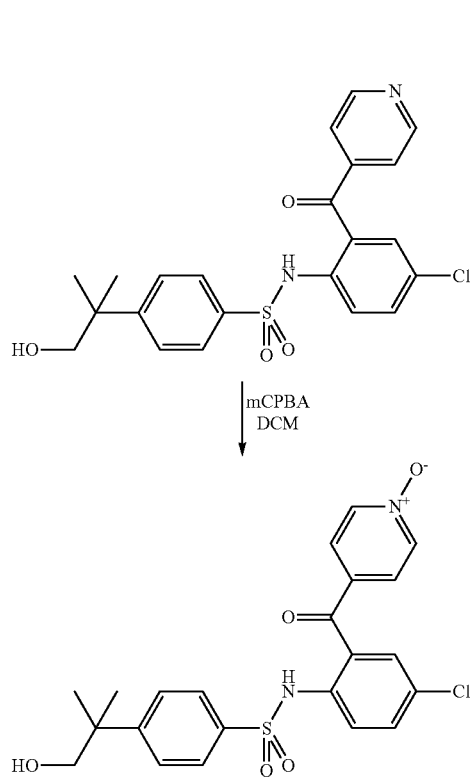

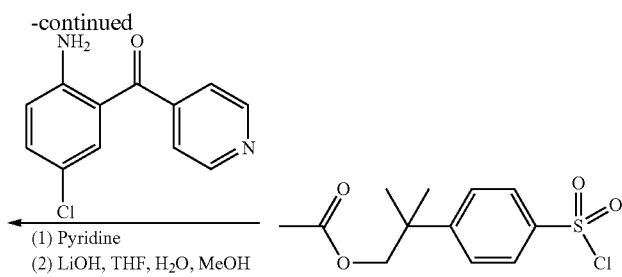

To a suspension of NaBH$_4$ (0.70 g, 18.3 mmol) in dry THF (20 mL) was added BF$_3$.Et$_2$O (0.25 mL, 20.1 mmol) drop wise at 0° C. over 5 min and the mixture was stirred for 30 min. A solution of 2-methyl-2-phenyl-propionic acid (1.0 g, 6.1 mmol) in dry THF (10 mL) was added drop wise at 0° C. over 30 min, and the mixture was stirred at room temperature for 4 h. Methanol was slowly added to the reaction mixture until hydrogen evolution stopped. The mixture was diluted with 10% HCl and extracted twice with EtOAc. The organic layer was dried over Na$_2$SO$_4$ and then under vacuum to yield colorless oil.

This material was dissolved in DCM (25 mL), pyridine (1.2 mL, 15.3 mmol) and acetyl chloride (2.2 mL, 30.5 mmol) added, and the reaction mixture left to stir at room temperature overnight. The reaction mixture was washed with 10% HCl and the organic layer was dried over MgSO$_4$.

The material was then dissolved in DCM (25 mL) and cooled to 0° C. Chlorosulfonic acid (1.2 mL, 18 mmol) was added drop wise over 15 minutes and the mixture was stirred at the same temperature for 3H. The volatiles were evaporated and SOCl$_2$ (10 mL) was added and the mixture stirred at room temperature for 3 h. The excess SOCl$_2$ was evaporated and the residue was treated with ice-water and extracted with ether. The organic layer was washed with water and brine, dried over MgSO$_4$ and concentrated in vacuo to afford the aryl sulfonyl chloride as a yellowish oil.

This oil was treated with a solution of (2-amino-5-chloro-phenyl)-pyridin-4-yl-methanone (1.2 g, 5 mmol) in 10 mL pyridine and heated at 60 C for 4 h. The solvent was evaporated and the residue suspended in 3M HCl (10 mL) and stirred at room temperature for 16 h. The reaction mixture was put in an ice bath and neutralized with concentrated NaOH solution. The white precipitate formed was collected by filtration, washed with water and dried in vacuo and purified by flash chromatography to yield 320 mg of N-[4-Chloro-2-(pyridine-4-carbonyl)-phenyl]-4-(2-hydroxy-1,1-dimethyl-ethyl)-benzenesulfonamide.

Oxidation of this intermediate with mCPBA according to the general procedure gave N-[4-chloro-2-(1-oxy-pyridine-4-carbonyl)-phenyl]-4-(2-hydroxy-1,1-dimethyl-ethyl)-benzenesulfonamide. $^1$H-NMR (400 MHz, CDCl$_3$): δ 1.24 (s, 6H), 3.58 (s, 2H), 7.29 (d, 1H, J=2.4 Hz), 7.37 (m, 4H), 7.53 (m, 2H), 7.62 (m, 2H), 7.78 (d, 1H, J=8.8 Hz), 8.23 (d, 2H, J=6.8 Hz), 9.51 (s, 1H). MS: m/z 461.1 (M$^+$+1).

Example 53

Synthesis of N-[4-chloro-2-(pyridine-4-carbonyl)-phenyl]-4-ethyl-benzenesulfonamide

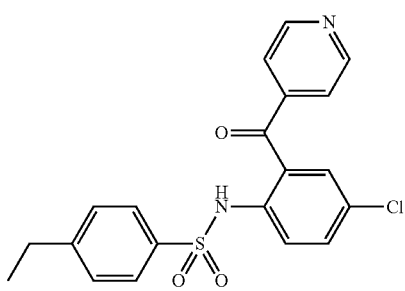

The title compound was prepared according to the general procedure for the synthesis of N-Aryl-benzenesulfonamides previously described using 116 mg of (2-amino-5-chloro-phenyl)-pyridin-4-yl-methanone and 102 mg of 4-ethyl-benzenesulfonyl chloride. $^1$H-NMR (400 MHz, CDCl$_3$): δ 0.94

(t, 3H, J=7.6 Hz), 2.38 (q, 2H, J=15.2 Hz, 7.6 Hz), 6.94 (d, 2H, J=6.8 Hz), 7.16 (m, 2H), 7.23 (m, 1H), 7.30 (m, 4H), 8.60 (b, 2H), 9.73 (b, 1H). MS: m/z 401.1 (M$^+$+1).

7.75 (m, 2H), 7.80 (m, 3H), 7.98 (s, 1H), 8.99 (d, 1H, J=5.2 Hz), 9.25 (b, 1H), 10.29 (b, 1H). MS: m/z 441.9 (M$^+$+1).

Example 54

Synthesis of N-[4-Chloro-2-(pyrimidine-2-carbonyl)-phenyl]-4-oxazol-5-yl-benzenesulfonamide

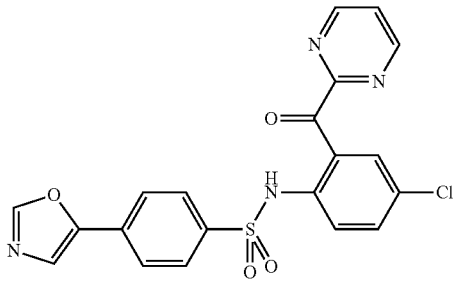

The title compound was prepared according to the general procedure for the synthesis of N-Aryl-benzenesulfonamides previously described using 116 mg of (2-Amino-5-chlorophenyl)-pyrimidin-2-yl-methanone and 122 mg of 4-oxazol-5-yl-benzenesulfonyl chloride. $^1$H-NMR (400 MHz, CDCl$_3$): δ 7.43 (s, 1H), 7.45 (m, 1H), 7.50 (m, 1H), 7.55 (m, 1H), 7.64 (m, 2H), 7.66 (d, 1H, J=8.8 Hz), 7.86 (m, 2H), 7.97 (s, 1H), 8.86 (d, 2H), 10.63 (s, 1H). MS: m/z 441.9 (M$^+$+1).

Example 55

Synthesis of N-[4-chloro-2-(pyrimidine-4-carbonyl)-phenyl]-4-oxazol-5-yl-benzenesulfonamide

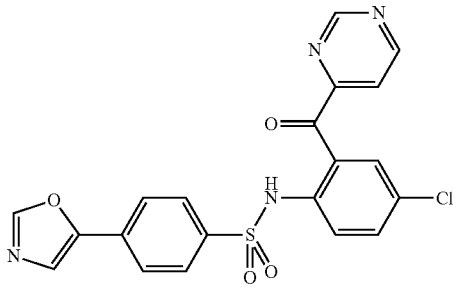

The title compound was prepared according to the general procedure for the synthesis of N-Aryl-benzenesulfonamides previously described using 116 mg of (2-Amino-5-chlorophenyl)-pyrimidin-4-yl-methanone and 122 mg of 4-oxazol-5-yl-benzenesulfonyl chloride. $^1$H-NMR (400 MHz, CDCl$_3$): δ 7.43 (s, 1H), 7.53 (dd, 1H, J=8.8 Hz, 2.4 Hz), 7.62 (m, 2H),

Example 56

Synthesis of N-[4-Chloro-2-(pyridine-3-carbonyl)-phenyl]-4-oxazol-5-yl-benzenesulfonamide

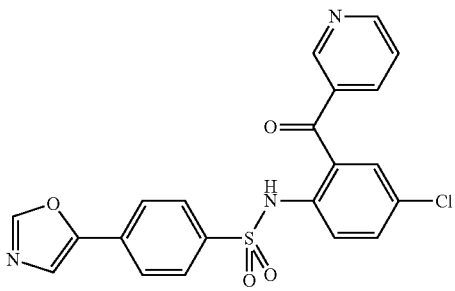

The title compound was prepared according to the general procedure for the synthesis of N-Aryl-benzenesulfonamides previously described using 116 mg of (2-Amino-5-chlorophenyl)-pyridin-3-yl-methanone and 122 mg of 4-oxazol-5-yl-benzenesulfonyl chloride. $^1$H-NMR (400 MHz, CDCl$_3$): δ 7.23 (m, 2H), 7.42-7.47 (m, 3H), 7.58-7.62 (m, 3H), 7.71 (dt, 1H, J=7.6 Hz, 2.0 Hz), 7.88 (s, 1H), 8.45 (b, 1H), 8.58 (bd, 1H, J=3.6 Hz), 9.67 (s, 1H). MS: m/z 458.1 (M$^+$+1)

Example 57

Synthesis of 4-tert-Butyl-N-[4-chloro-2-(pyridine-2-carbonyl)-phenyl]-benzenesulfonamide

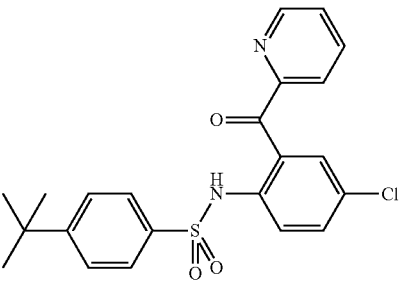

The title compound was prepared according to the general procedure for the synthesis of N-Aryl-benzenesulfonamides previously described using 116 mg of (2-Amino-5-chlorophenyl)-pyridin-2-yl-methanone and 116 mg of 4-tert-Butyl-benzenesulfonyl chloride. $^1$H-NMR (400 MHz, CDCl$_3$): δ 1.24 (s, 9H), 7.34-7.38 (m, 2H), 7.47 (dd, 1H, J=8.8 Hz, 2.4

Hz), 7.60 (m, 1H), 7.65-7.68 (m, 4H), 7.85 (d, 1H, J=8 Hz), 8.00 (td, 1H, J=7.6 Hz, 2 Hz), 8.71 (bd, 1H, J=4.8 Hz). MS: m/z 429.9 (M$^+$+1).

Example 58

Synthesis of N-[4-Chloro-2-(pyridine-4-carbonyl)-phenyl]-4-(1,1-dimethyl-propyl)-benzenesulfonamide

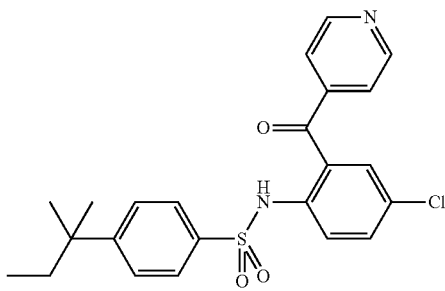

The title compound was prepared according to the general procedure for the synthesis of N-Aryl-benzenesulfonamides previously described using 116 mg of (2-amino-5-chloro-phenyl)-pyridin-4-yl-methanone and 123 mg of 4-(1,1-dimethyl-propyl)-benzenesulfonylchloride. $^1$H-NMR (400 MHz, CDCl$_3$): δ 0.59 (t, 3H, J=7.2 Hz), 1.23 (s, 6H), 1.61 (q, 2H, J=7.2 Hz), 7.28 (d, 1H, J=2.8 Hz), 7.36 (m, 2H), 7.53 (m, 3H), 7.67-7.74 (m, 3H), 8.84 (m, 2H), 10.14 (s, 1H). MS: m/z 443.9 (M$^+$+1).

Example 59

Synthesis of 4-tert-butyl-N-[4-chloro-2-(2-chloro-pyridine-4-carbonyl)-phenyl]-benzenesulfonamide

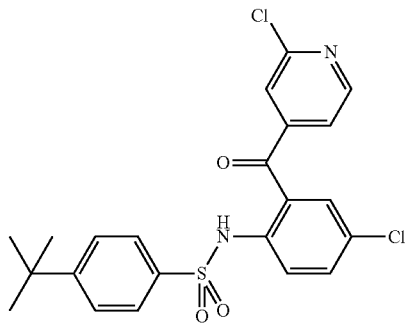

The title compound was prepared according to the general procedure for the synthesis of N-Aryl-benzenesulfonamides previously described using 133 mg of (2-Amino-5-chloro-phenyl)-(2-chloro-pyridin-4-yl)-methanone and 116 mg of 4-tert-Butyl-benzenesulfonyl chloride. $^1$H-NMR (400 MHz, CDCl$_3$): δ 1.26 (s, 9H), 7.18 (dd, 5.2 Hz, 1.6 Hz), 7.25 (m, 1H), 7.32 (m, 1H), 7.41 (d, 2H, J=6.4 Hz), 7.54 (dd, 1H, J=9.2

Hz, 2.4 Hz), 7.67 (m, 2H), 7.77 (d, 1H, J-8.8 Hz), 8.55 (d, 1H, J=5.2 Hz), 10.09 (s, 1H). MS: m/z 463.0 (M$^+$+1).

Example 60

Synthesis of N-[4-Chloro-2-(6-methyl-pyridine-2-carbonyl)-phenyl]-4-oxazol-5-yl-benzenesulfonamide

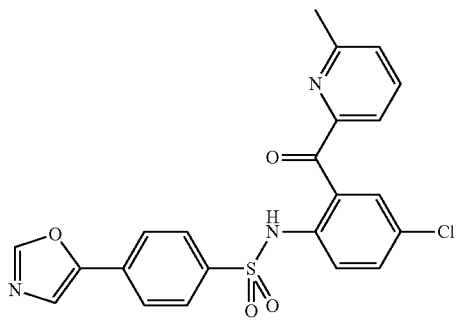

The title compound was prepared according to the general procedure for the synthesis of N-Aryl-benzenesulfonamides previously described using 123 mg of (2-Amino-5-chloro-phenyl)-(6-methyl-pyridin-2-yl)-methanone and 122 mg of 4-oxazol-5-yl-benzenesulfonyl chloride. $^1$H-NMR (400 MHz, CDCl$_3$): δ 2.67 (s, 3H), 7.46-7.50 (m, 4H), 7.61-7.70 (m, 4H), 7.65 (m, 2H), 7.94-8.00 (m, 1H), 8.15 (s, 1H). MS: m/z 454.0 (M$^+$+1).

Example 61

Synthesis of 4-tert-Butyl-N-[4-chloro-2-(2-methyl-pyridine-4-carbonyl)-phenyl]benzenesulfonamide

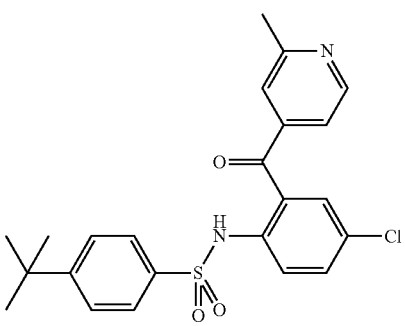

The title compound was prepared according to the general procedure for the synthesis of N-Aryl-benzenesulfonamides previously described using 123 mg of (2-Amino-5-chloro-phenyl)-(2-methyl-pyridin-4-yl)-methanone and 116 mg of 4-tert-Butyl-benzenesulfonyl chloride. $^1$H-NMR (400 MHz, CDCl$_3$): δ 1.26 (s, 9H), 2.63 (s, 3H) 7.29 (d, 1H, J=2.8 Hz), 7.45-7.55 (m, 3H), 7.67 (m, 2H), 7.83 (m, 2H), 8.03 (s, 1H), 8.81 (d, 1H, J=5.6 Hz), 10.10 (s, 1H). MS: m/z 443.9 (M⁺+1).

Example 62

Synthesis 4-tert-Butyl-N-[4-chloro-2-(2-methyl-1-oxy-pyridine-4-carbonyl)-phenyl]-benzenesulfonamide

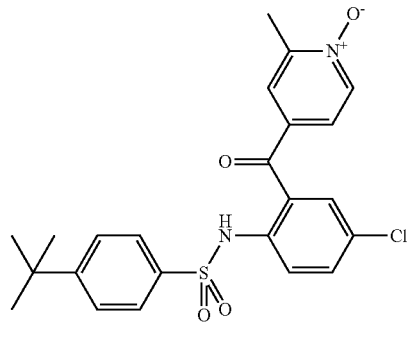

The title compound was prepared according to the general procedure by mCPBA oxidation of 4-tert-butyl-N-[4-chloro-2-(2-methyl-pyridine-4-carbonyl)-phenyl]-benzenesulfonamide. ¹H-NMR (400 MHz, CDCl₃): δ 1.26 (s, 9H), 2.63 (s, 3H) 7.29 (d, 1H, J=2.8 Hz), 7.50-7.57 (m, 3H), 7.67 (m, 2H), 7.87 (m, 2H), 8.24 (s, 1H), 8.89 (d, 1H, J=5.6 Hz), 10.31 (s, 1H). MS: m/z 459.0 (M⁺+1)

Example 63

Synthesis of 4-tert-Butyl-N-[4-chloro-2-(6-methylsulfanyl-pyridine-3-carbonyl)-phenyl]-benzenesulfonamide

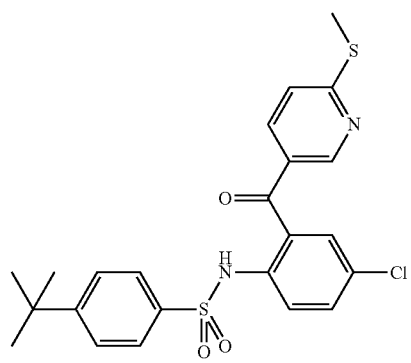

4-tert-Butyl-N-[4-chloro-2-(6-chloro-pyridine-3-carbonyl)-phenyl]-benzenesulfonamide (231 mg, 0.5 mmol) was dissolved in dry THF (5 mL) and treated with sodium thiomethoxide (175 mg, 2.5 mmol) and the mixture was heated at 70° C. for 4 h. The solvent was evaporated and the residue suspended in water (5 mL) and the product was precipitated by the drop wise addition of 3M HCl and purified by HPLC. ¹H-NMR (400 MHz, CDCl₃): δ 1.19 (s, 9H), 2.60 (s, 3H), 7.21-7.28 (m, 3H), 7.31 (m, 1H), 7.50-7.54 (m, 3H), 7.65 (dd, 1H, J=8.4 Hz, 2.4 Hz), 7.78 (d, 1H, J=8.8 Hz), 8.19 (m, 1H), 9.62 (s, 1H). MS: m/z 476.0 (M⁺+1).

Example 64

Synthesis of 4-tert-Butyl-N-[4-chloro-2-(6-methanesulfonyl-pyridine-3-carbonyl)-phenyl]-benzenesulfonamide

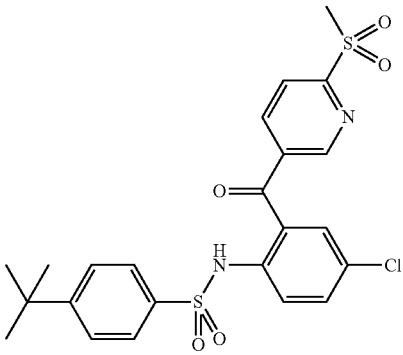

4-tert-Butyl-N-[4-chloro-2-(6-methylsulfanyl-pyridine-3-carbonyl)-phenyl]-benzenesulfonamide (48 mg, 0.1 mmol) and mCPBA (35 mg, 0.2 mmol) were dissolved in DCM (4 mL) and the mixture stirred at room temperature overnight. The solvent was evaporated and product was purified by HPLC. ¹H-NMR (400 MHz, CDCl₃): δ 1.25 (s, 9H), 3.30 (s, 3H), 7.27 (m, 1H), 7.38 (m, 2H), 7.56 (dd, 1H, J=8.8 Hz, 2.8 Hz), 7.66 (m, 2H), 7.80 (d, 1H, J=8.8 Hz), 8.04 (dd, 1H, J=8 Hz, 2 Hz), 8.18 (d, 1H, J=8.0 Hz), 8.61 (m, 1H), 10.00 (s, 1H). MS: m/z 508.0 (M⁺+1).

Example 65

Synthesis of 4-tert-Butyl-N-[3,4-difluoro-2-(pyridine-4-carbonyl)-phenyl]-benzenesulfonamide

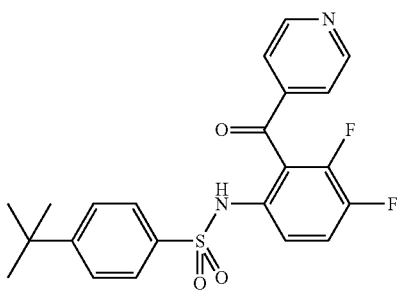

The title compound was prepared according to the general procedure for the synthesis of N-Aryl-benzenesulfonamides previously described using 117 mg of (6-Amino-2,3-difluoro-phenyl)-pyridin-4-yl-methanone and 116 mg of 4-tert-Butyl-benzenesulfonyl chloride. ¹H-NMR (400 MHz, CDCl₃): δ 1.22 (s, 9H), 7.31 (d, 2H, J=8.4 Hz), 7.40-7.47 (m, 3H), 7.55 (d, 2H, J=8.4 Hz), 7.59 (m, 1H), 8.69 (b, 1H), 8.82 (d, 2H, J=6.0 Hz). MS: m/z 431.0 (M⁺+1).

Example 66

Synthesis of 4-tert-Butyl-N-[4-chloro-2-(pyrazine-2-carbonyl)-phenyl]-benzenesulfonamide

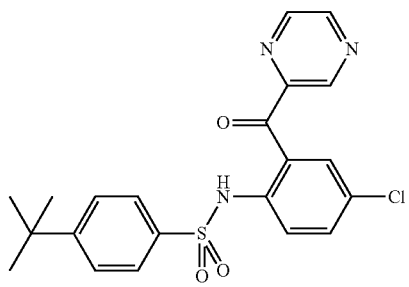

The title compound was prepared according to the general procedure for the synthesis of N-Aryl-benzenesulfonamides previously described using 117 mg of (2-Amino-5-chloro-phenyl)-pyrazin-2-yl-methanone and 116 mg of 4-tert-butyl-benzenesulfonyl chloride. ¹H-NMR (400 MHz, CDCl₃): δ 1.24 (s, 9H), 7.38 (dm, 2H, J=6.8 Hz), 7.50 (dd, 1H, J=9.2 Hz, 1.6 Hz), 7.70 (m, 2H), 7.76 (m, 1H), 7.80 (m, 1H), 8.62 (m, 1H), 8.77 (m, 1H), 9.06 (m, 1H), 10.37 (s, 1H). MS: m/z 430.0 (M⁺+1).

Example 67

Synthesis of N-[4-Chloro-2-(pyridine-4-carbonyl)-phenyl]-4-isopropoxy-benzenesulfonamide

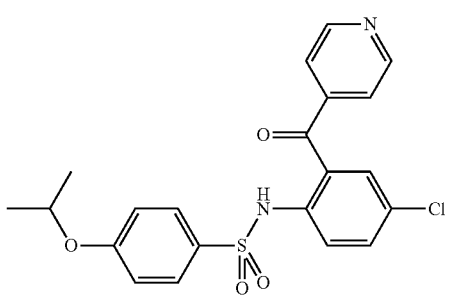

The title compound was prepared according to the general procedure for the synthesis of N-Aryl-benzenesulfonamides previously described using 116 mg of (2-Amino-5-chloro-phenyl)-pyridin-4-yl-methanone and 117 mg of 4-Isopropoxy-benzenesulfonyl chloride. ¹H-NMR (400 MHz, CDCl₃): δ 1.01 (d, 6H, J=5.6 Hz), 4.27 (m, 1H), 6.51 (d, 2H, J=8.8 Hz), 6.87 (d, 1H, J=8.8 Hz), 7.15-7.25 (m, 4H), 7.60 (d, 2H, J=6.0 Hz), 8.64 (d, 2H, J=6 Hz), 9.60 (s, 1H). MS: m/z 431.9 (M⁺+1).

Example 68

Synthesis of N-[4-Bromo-2-(pyridine-4-carbonyl)-phenyl]-4-isopropoxy-benzenesulfonamide

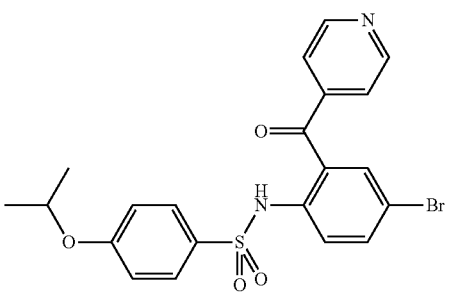

The title compound was prepared according to the general procedure for the synthesis of N-Aryl-benzenesulfonamides previously described using 138 mg of (2-Amino-5-bromo-phenyl)-pyridin-4-yl-methanone and 117 mg of 4-Isopropoxy-benzenesulfonyl chloride. ¹H-NMR (400 MHz, CDCl₃): δ 1.31 (d, 6H, J=6 Hz), 4.49 (q, 1H, J=6.0 Hz), 6.73 (d, 2H, J=6.8 Hz), 7.39 (m, 3H), 7.63-7.70 (m, 4H), 8.82 (d, 2H, J=6.0 Hz), 9.99 (s, 1H). MS: m/z 476.0 (M⁺+1)

Example 69

Synthesis of N-[4-Bromo-2-(pyridine-4-carbonyl)-phenyl]-4-ethyl-benzenesulfonamide

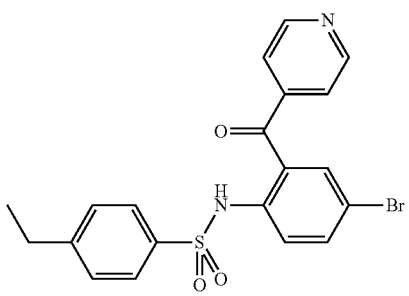

The title compound was prepared according to the general procedure for the synthesis of N-Aryl-benzenesulfonamides previously described using 138 mg of (2-Amino-5-bromo-phenyl)-pyridin-4-yl-methanone and 102 mg of 4-ethyl-benzenesulfonyl chloride. ¹H-NMR (400 MHz, CDCl₃): δ 1.19 (t, 3H, J=7.6 Hz), 2.62 (q, 2H, J=7.6 Hz), 7.20 (d, 2H, J=8.8

Hz, 7.38 (m, 3H), 7.65-7.72 (m, 4H), 8.81 (d, 2H, 6.4 Hz), 10.06 (s, 1H). MS: m/z 446.0 (M⁺+1).

Example 70

Synthesis of N-[4-Bromo-2-(pyridine-4-carbonyl)-phenyl]-4-trifluoromethoxy-benzenesulfonamide

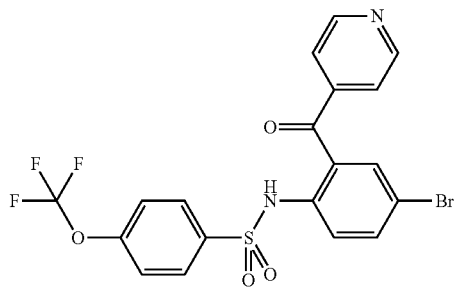

The title compound was prepared according to the general procedure for the synthesis of N-Aryl-benzenesulfonamides previously described using 138 mg of (2-Amino-5-bromo-phenyl)-pyridin-4-yl-methanone and 130 mg of 4-Trifluoromethoxy-benzenesulfonyl chloride. ¹H-NMR (400 MHz, CDCl₃): δ 7.23 (d, 2H, J=8.0 Hz), 7.45 (m, 3H), 7.71 (m, 2H), 7.85 (d, 2H, J=8.8 Hz), 8.85 (d, 2H, J=6.4 Hz), 10.23 (s, 1H). MS: m/z 502.9 (M⁺+1).

Example 71

Synthesis of 4-tert-Butyl-N-[4-chloro-2-(2-cyano-pyridine-4-carbonyl)-phenyl]-benzenesulfonamide

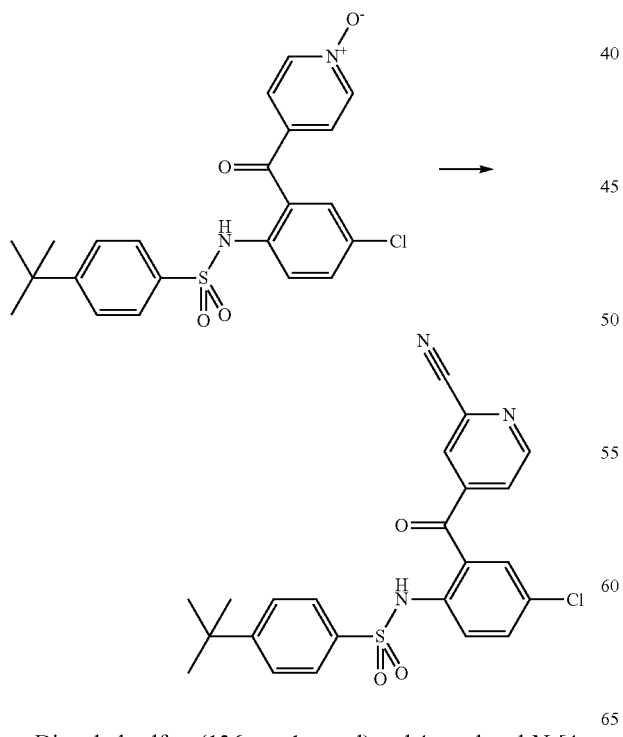

Dimethyl sulfate (126 mg, 1 mmol) and 4-tert-butyl-N-[4-chloro-2-(1-oxy-pyridine-4-carbonyl)-phenyl]-benzenesulfonamide (445 mg, 1 mmol) were dissolved in dry THF (5 mL). The reaction mixture was stirred at room temperature for 1 hour and at 60° C. for two hours. After cooling to room temperature, to the solution was added 25% (w/v) aqueous KCN solution (5 mL) and the mixture stirred for 16 h. The solvent was evaporated in vacuo and the product was purified by HPLC. ¹H-NMR (400 MHz, CDCl₃): δ 1.27 (s, 9H), 7.22 (d, 1H, J=2.0 Hz), 7.41-7.47 (m, 3H), 7.56 (dd, 1H, J=2.4 Hz), 7.69 (m, 3H), 7.79 (d, 1H, J=9.2 Hz), 8.87 (d, 1H, J=5.2 Hz), 10.06 (s, 1H). MS: m/z 454.0 (M⁺+1).

Example 72

Synthesis of 4-tert-Butyl-N-[4-chloro-2-(2-methanesulfonyl-pyridine-4-carbonyl)-phenyl]-benzenesulfonamide

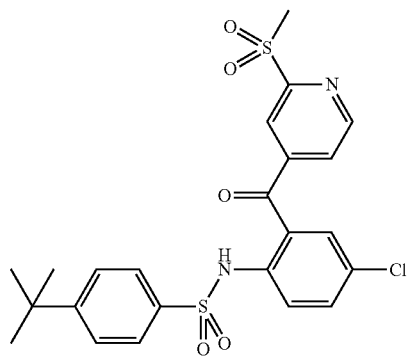

4-tert-Butyl-N-[4-chloro-2-(2-chloro-pyridine-4-carbonyl)-phenyl]-benzenesulfonamide (232 mg, 0.5 mmol) was dissolved in dry THF (5 mL) and treated with sodium thiomethoxide (175 mg, 2.5 mmol) and the mixture was heated at 70° C. for 16 h. The solvent was evaporated and the residue suspended in water (5 mL) and the product was precipitated by the drop wise addition of 3M HCl. The precipitate was collected by filtration, dissolved in DCM (10 mL) and treated with mCPBA (172 mg, 1 mmol). After stirring at room temperature for 16 h, the DCM solution was washed with saturated NaHCO₃ solution (10 mL). The organic layer was washed with water, dried and the solvent was evaporated. The product was purified by HPLC to give white powder after lyophilization. ¹H-NMR (400 MHz, CDCl₃): δ 1.28 (s, 9H), 3.30 (s, 3H), 7.24 (d, 1H, J=2.4 Hz), 7.45 (d, 2H, J=8.0 Hz), 7.48 (m, 1H), 7.54 (dd, 1H, J=8.8 Hz, 2.4 Hz), 7.74 (d, 2H, J=8.0 Hz), 7.78 (d, 1H, J=8.8 Hz), 8.87 (d, 1H, J=5.2 Hz), 10.23 (s, 1H). MS: m/z 507.0 (M⁺+1).

Example 73

Synthesis of N-[4-Bromo-2-(pyridine-4-carbonyl)-phenyl]-4-methanesulfonyl-benzenesulfonamide

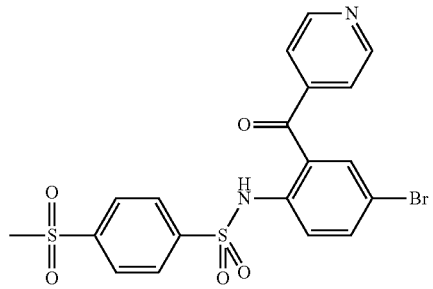

The title compound was prepared according to the general procedure for the synthesis of N-Aryl-benzenesulfonamides previously described using 138 mg of (2-Amino-5-bromo-phenyl)-phenyl-methanone and 127 mg of 4-Methanesulfonyl-benzenesulfonyl chloride. $^1$H-NMR (400 MHz, CDCl$_3$): δ 3.07 (s, 3H), 7.45 (d, 1H, J=2.0 Hz), 7.49 (d, 2H, J=6.0 Hz), 7.15 (m, 3H), 8.00 (s, 4H), 8.89 (d, 2H, J=6.0 Hz), 10.32 (b, 1H). MS: m/z 496.9.0 (M$^+$+1).

Example 74

Synthesis of 4-Acetyl-N-[4-bromo-2-(pyridine-4-carbonyl)-phenyl]-benzenesulfonamide

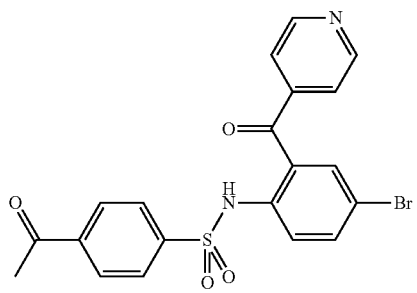

The title compound was prepared according to the general procedure for the synthesis of N-Aryl-benzenesulfonamides previously described using 138 mg of (2-Amino-5-bromo-phenyl)-phenyl-methanone and 109 mg of 4-acetyl-benzenesulfonyl chloride. $^1$H-NMR (400 MHz, CDCl$_3$): δ 2.59 (s, 3H), 7.44 (d, 1H, J=2.0 Hz), 7.56 (d, 2H, J=6.4 Hz, 7.64-7.71 (m, 2H), 7.90 (d, 2H, J=8.8 Hz), 7.97 (d, 2H, J=8.8 Hz), 8.88 (d, 2H, J=6.4 Hz), 10.24 (b, 1H). MS: m/z 459.8 (M$^+$+1).

Example 75

Synthesis of 4-tert-Butyl-N-[4-chloro-2-(6-methyl-pyridine-2-carbonyl)-phenyl]-benzenesulfonamide

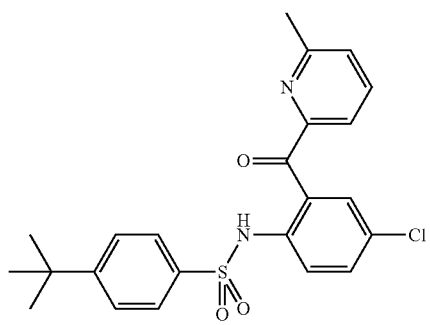

The title compound was prepared according to the general procedure for the synthesis of N-Aryl-benzenesulfonamides previously described using (2-Amino-5-chloro-phenyl)-(6-methyl-pyridin-2-yl)-methanone and 4-tert-Butyl-benzenesulfonyl chloride and purified by HPLC. $^1$H NMR: δ 1.29 (s, 9H), 2.94 (s, 3H), 7.42-7.46 (m, 3H), 7.51 (d, J=8.8 Hz, 1H), 7.58 (d, J=2.0 Hz, 1H), 7.62 (d, J=7.2 Hz, 1 H), 7.66 (d, J=6.8 Hz, 1H), 7.74 (d, J=8.0 Hz, 1 H), 8.1 (bs, 1H). MS: M/z 443.1 (M$^+$+1).

Example 76

Synthesis of 4-tert-Butyl-N-[4-chloro-2-(6-chloro-pyridine-3-carbonyl)-phenyl]-benzenesulfonamide

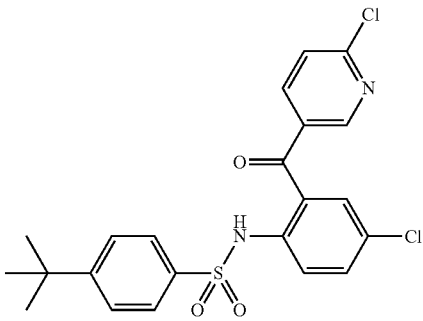

The title compound was prepared according to the general procedure for the synthesis of N-Aryl-benzenesulfonamides previously described using (2-Amino-5-chloro-phenyl)-(6-chloro-pyridin-3-yl)-methanone and 4-tert-butyl-benzenesulfonyl chloride and purified by HPLC. $^1$H NMR: δ 1.21 (s, 9H), 7.30 (d, J=2.4 Hz, 1H), 7.33 (d, J=6.6 Hz, 2H), 7.43 (d, J=8.0 Hz, 1 H), 7.52 & 7.55 (dd, J=8.8 Hz, 2.8 Hz, 1H), 7.60 (d, J=7.0 Hz, 1 H), 7.79 (m, 3 H), 8.27 (d, J=2.0 Hz, 1H), 9.73 (s, 1H). MS: M/z 463.0 (M$^+$+1).

Example 77

Synthesis of N-[4-Chloro-2-(pyridine-3-carbonyl)-phenyl]-4-trifluoromethoxy-benzenesulfonamide

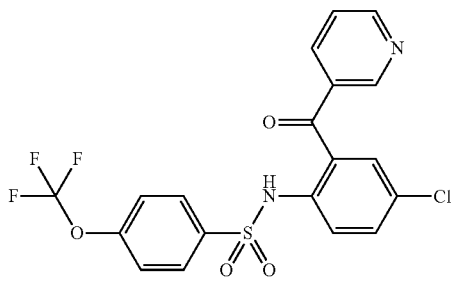

The title compound was prepared according to the general procedure for the synthesis of N-Aryl-benzenesulfonamides previously described using (2-amino-5-chloro-phenyl)-pyridin-3-yl-methanone and 4-Trifluoromethoxy-benzenesulfonyl chloride and purified by HPLC. $^1$H NMR: δ 6.93 (d, J=8.0 Hz, 1H), 7.51 (d, J=8.8 Hz, 2H), 7.58-7.61 (m, 3 H), 7.67 (d, J=8.8 Hz, 2H), 8.03-8.05 (m, 1H), 8.74 (d, J=1.6 Hz, 1H), 8.79 & 8.80 (dd, J=6.0 Hz, 1.6 Hz, 1H), 9.73 (s, 1H). MS: M/z 456.9 (M⁺+1).

Example 78

Synthesis of N-[4-Chloro-2-(pyridine-3-carbonyl)-phenyl]-4-methanesulfonyl-benzenesulfonamide

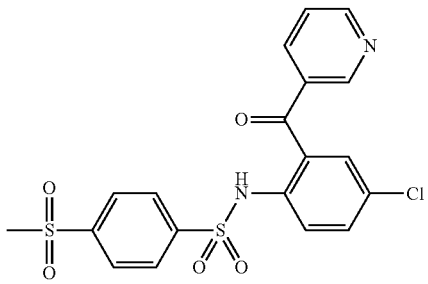

The title compound was prepared according to the general procedure for the synthesis of N-Aryl-benzenesulfonamides previously described using (2-amino-5-chloro-phenyl)-pyridin-3-yl-methanone and 4-Methanesulfonyl-benzenesulfonyl chloride and purified by HPLC. ¹H NMR (CDCl₃): δ 3.01 (s, 3 H), 7.36-7.37 (d, J=2.4 Hz, 1H), 7.43 (m, 1H), 7.54 & 7.57 (dd, J=8.8 Hz, 2.4 Hz, 1H), 7.70-7.73 (m, 1H), 7.77 (d, J=8.8 Hz, 1H), 7.90 (m, 4H), 8.59 (d, J=2.0 Hz, 1H), 8.80 & 8.82 (dd, J=4.8 Hz, 1.6 Hz, 1H), 9.98 (s, 1H). MS: M/z 450.9 (M⁺+1).

Example 79

Synthesis of N-[4-Chloro-2-(pyridine-4-carbonyl)-phenyl]-4-trifluoromethoxy-benzenesulfonamide

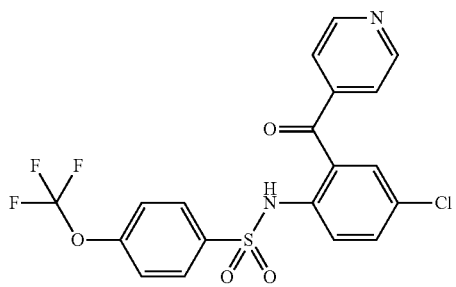

The title compound was prepared according to the general procedure for the synthesis of N-Aryl-benzenesulfonamides previously described using (2-amino-5-chloro-phenyl)-pyridin-4-yl-methanone and 4-Trifluoromethoxy-benzenesulfonyl chloride and purified by HPLC. ¹H NMR (DMSO-d6): δ 6.90 (d, J=8.4 Hz, 1H), 7.50 (d, J=8.8 Hz, 2H), 7.49-7.61 (m, 4H), 7.66 (d, J=8.8 Hz, 2H), 8.81 (d, J=4.8 Hz, 2H), 10.26 (s, 1H). MS: M/z 456.9 (M⁺+1).

Example 80

Synthesis of N-[4-Chloro-2-(pyridine-3-carbonyl)-phenyl]-4-isopropoxy-benzenesulfonamide

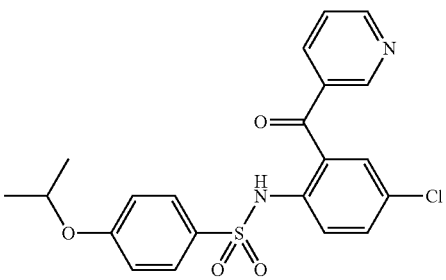

The title compound was prepared according to the general procedure for the synthesis of N-Aryl-benzenesulfonamides previously described using (2-amino-5-chloro-phenyl)-pyridin-3-yl-methanone and 4-isopropoxy-benzenesulfonyl chloride and purified by HPLC. ¹H NMR (CDCl₃): δ 1.19 (s, 3H), 1.20 (s, 3H), 4.35-4.38 (m, 1H), 6.63 (d, J=9.2 Hz, 2H), 7.24 (m, 2H), 7.35-7.38 (m, 1H), 7.43 (d, J=2.4 Hz, 1H), 7.45-7.49 (m, 2H), 7.62 (d, J=8.8 Hz, 1H), 7.70-7.73 (m, 1H), 8.51 (bs, 1H), 8.68 (bs, 1H), MS: M/z=431.0 (M⁺+1).

Example 81

Synthesis of 4-Acetyl-N-[4-chloro-2-(1-oxy-pyridine-3-carbonyl)-phenyl]-benzenesulfonamide

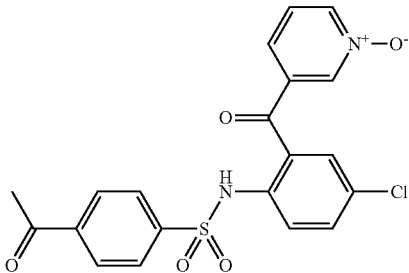

The title compound was prepared by the mCPBA oxidation of 4-Acetyl-N-[4-chloro-2-(pyridine-3-carbonyl)-phenyl]-benzenesulfonamide according to the general procedure.

Example 82

Synthesis of N-[4-Chloro-2-(1-oxy-pyridine-3-carbonyl)-phenyl]-4-methanesulfonyl-benzenesulfonamide

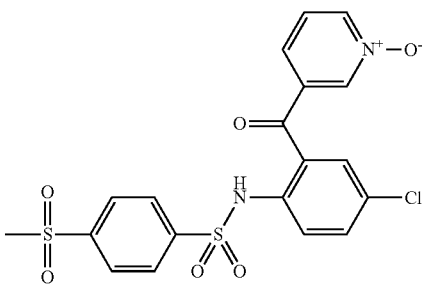

The title compound was prepared by the mCPBA oxidation of 4-methanesulfonyl-N-[4-chloro-2-(pyridine-3-carbonyl)-phenyl]-benzenesulfonamide according to the general procedure. ¹H NMR (DMSO-d6): δ 3.27 (s, 3H), 6.90 (d, J=8.8 Hz, 1H), 7.47 & 7.49 (dd, J=8.0 Hz, 1.2 Hz, 1H), 7.51-7.55 (m, 1 H), 7.56 & 7.58 (dd, J=8.0 Hz, 2.4 Hz, 1H), 7.62 (d, J=2.0 Hz, 1H), 7.79 (d, J=7.6 Hz, 2H), 8.05 (d, J=8.8 Hz, 2H), 8.19 (d, J=2.0 Hz, 1H), 8.41 & 8.42 (dd, J=6.8 Hz, 1.2 Hz, 1H), 10.46 (s, 1H). MS: M/z 467.0 (M⁺+1).

Example 83

Synthesis of 4-Chloro-N-[4-chloro-2-(pyridine-4-carbonyl)-phenyl]-benzenesulfonamide

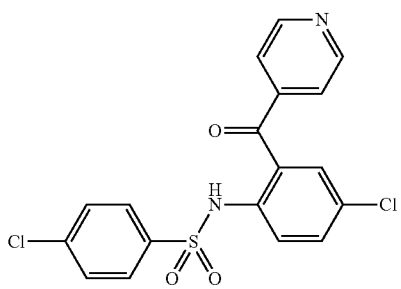

The title compound was prepared according to the general procedure for the synthesis of N-Aryl-benzenesulfonamides previously described using (2-amino-5-chloro-phenyl)-pyridin-4-yl-methasone and 4-chloro-benzenesulfonyl chloride and purified by HPLC. ¹H NMR (CDCl₃): δ 7.20 (dd, 2H, J=4.4 Hz, 2.0), 7.31 (m, 2H), 7.53 (dd, 1H, J=8.8 Hz, 2.8 Hz), 7.65 (m, 2H), 7.76 (d, 1H, J=8.8 Hz), 8.79 (dd, 2H, J=4.4 Hz, 1.6 Hz), 10.00 (s, 1H). MS: m/z 407.1 (M⁺+1).

Example 84

Synthesis of 4-tert-Butyl-N-[4-chloro-2-(pyridine-3-carbonyl)-phenyl]-benzenesulfonamide

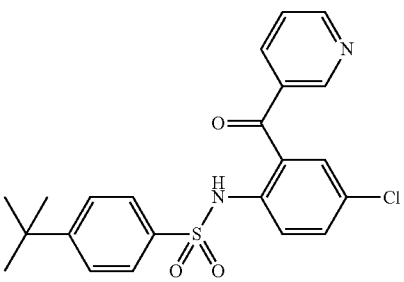

To (2-amino-5-chloro-phenyl)-pyridin-3-yl-methanone (150 mg, 0.64 mmol) dissolved in 750 uL pyridine was added 4-tert-butylbenzenesulfonyl chloride (225 mg, 0.97 mmol) and the mixture stirred at 60° C. overnight. The reaction mixture was diluted with 1.0 mL H₂O and the precipitate formed was collected by vacuum filtration. The crude product was recrystallized from EtOAc/hexane yielding 190 mg of pure title compound. 1H NMR (CDCl3) δ 9.87 (s, 1H), 8.79 (d, J=4.8 Hz, 1H), 8.52 (s, 1H), 7.79 (d, J=8.8 Hz, 2H), 7.61 (d, J=8.8 Hz, 2H), 7.52 (dd, J=8.8 Hz, 2.4 Hz, 1H), 7.40 (dd, J=7.6 Hz, 4.8 Hz, 1H), 7.33-7.31 (m, 3H), 1.22 (s, 9H). MS: m/z=429.0 (M⁺+1).

Example 85

Synthesis of 4-tert-Butyl-N-[4-chloro-2-(1-oxy-pyridine-3-carbonyl)-phenyl]-benzenesulfonamide

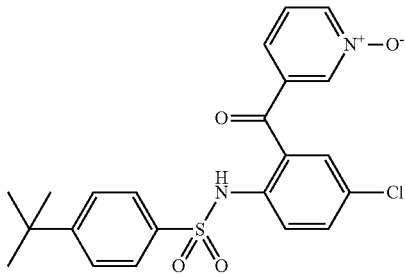

The title compound was prepared by the mCPBA oxidation of 4-tert-Butyl-N-[4-chloro-2-(pyridine-3-carbonyl)-phenyl]-benzenesulfonamide according to the general procedure and purified by HPLC. 1H NMR (CDCl3) δ 9.71 (s, 1H) 8.56 (d, J=7.6 Hz, 1H) 8.43 (s, 1H) 7.71-7.66 (m, 4H) 7.61-7.53 (m, 2H) 7.44-7.38 (m, 3H) 1.28 (s, 9H). MS (ES) m/z=445.0 (M⁺+1).

Example 86

Synthesis of N-[4-Chloro-2-(2-methyl-pyridine-4-carbonyl)-phenyl]-4-trifluoromethoxy-benzenesulfonamide

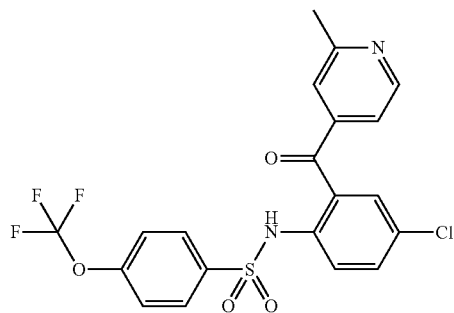

The title compound was prepared according to the general procedure for the synthesis of N-Aryl-benzenesulfonamides previously described using (2-Amino-5-chloro-phenyl)-(2-methyl-pyridin-4-yl)-methanone and 4-trifluoromethoxybenzenesulfonyl chloride and purified by HPLC. 1H NMR (CDCl3) δ 10.17 (s, 1H) 8.63 (d, J=4 Hz, 1H) 7.78 (m, 3H)

7.51 (s, 1H) 7.30 (s, 1H) 7.17 (s, 1H) 7.09 (s, 1H) 6.97 (d, J=4 Hz, 2H) 2.64 (s, 3H). MS (ES) m/z=471.0 (M⁺+1).

Example 87

Synthesis of N-[4-Chloro-2-(2-methyl-pyridine-4-carbonyl)-phenyl]-4-isopropoxy-benzenesulfonamide

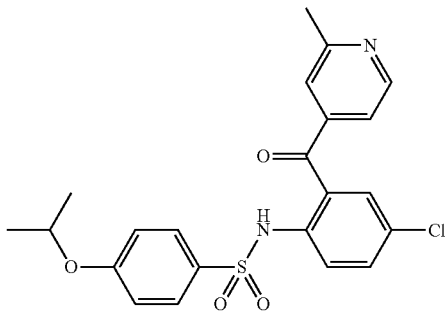

The title compound was prepared according to the general procedure for the synthesis of N-Aryl-benzenesulfonamides previously described using (2-Amino-5-chloro-phenyl)-(2-methyl-pyridin-4-yl)-methanone and 4-isopropoxy-benzenesulfonyl chloride and purified by HPLC. 1H NMR (CDCl3) δ 9.94 (s, 1H) 8.61 (d, J=5 Hz, 1H) 7.78 (d, J=8.8, 1H) 7.61 (d, J=8 Hz, 1H) 7.50 (dd, J=11 Hz, 2 Hz, 2H) 7.27 (d, J=2.4 Hz, 1H) 7.07 (s, 1H) 6.96 (d, J=4 Hz, 1H) 6.75 (d, J=8.8 Hz, 2H) 4.47 (m, 1H) 2.63 (s, 3H) 1.27 (s, 6H). MS (ES) m/z=445.0 (M⁺+1).

Example 88

Synthesis of 4-Acetyl-N-[4-chloro-2-(2-methyl-pyridine-4-carbonyl)-phenyl]-benzenesulfonamide

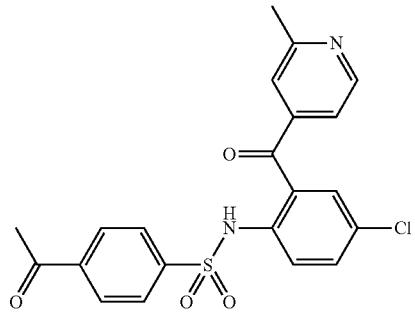

The title compound was prepared according to the general procedure for the synthesis of N-Aryl-benzenesulfonamides previously described using (2-Amino-5-chloro-phenyl)-(2-methyl-pyridin-4-yl)-methanone and 4-acetyl-benzenesulfonyl chloride and purified by HPLC. 1H NMR (CDCl3) δ 8.50

(d, J=4.8 Hz, 1H) 7.67-7.25 (m, 5H) 7.20-6.85 (m, 4H) 2.52 (s, 3H) 2.45 (s, 3H). MS: (ES) m/z=429.0 (M⁺+1).

Example 89

Synthesis of N-[4-Chloro-2-(2-methyl-pyridine-4-carbonyl)-phenyl]-4-methanesulfonyl-benzenesulfonamide

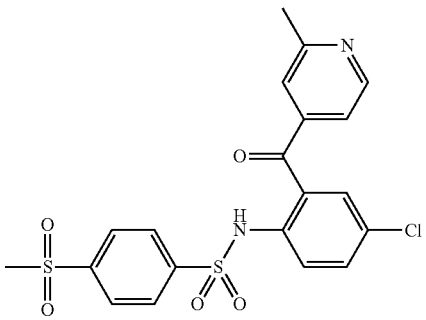

The title compound was prepared according to the general procedure for the synthesis of N-Aryl-benzenesulfonamides previously described using (2-Amino-5-chloro-phenyl)-(2-methyl-pyridin-4-yl)-methanone and 4-methanesulfonyl-benzenesulfonyl chloride and purified by HPLC. 1H NMR (CDCl3) δ 10.38 (s, 1H) 8.64 (s 1H) 7.95 (s, 4H) 7.72 (s, 1H) 7.51 (s, 1H) 7.31 (s, 1H) 7.11 (s, 1H) 6.99 (s, 1H) 3.04 (s, 3H) 2.64 (s, 3H). MS: (ES) m/z=464.9 (M⁺+1).

Example 90

Synthesis of 3-{4-[4-Chloro-2-(2-methyl-pyridine-4-carbonyl)-phenylsulfamoyl]-phenyl}-propionic acid methyl ester

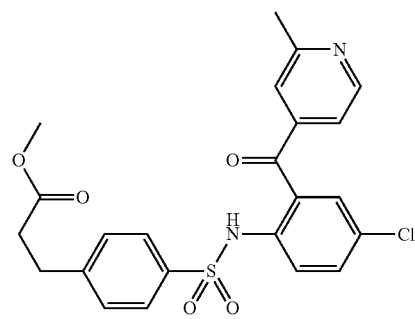

The title compound was prepared according to the general procedure for the synthesis of N-Aryl-benzenesulfonamides previously described using (2-Amino-5-chloro-phenyl)-(2-methyl-pyridin-4-yl)-methanone and 3-(4-chlorosulfonyl-phenyl)-propionic acid methyl ester and purified by HPLC. 1H NMR (CDCl3) δ 10.13 (s, 1H) 8.62 (d, J=4.8 Hz, 1H) 7.73 (d, J=8.8 Hz, 1H) 7.65 (d, J=8.8 Hz, 2H) 7.49 (dd, J=8.8 Hz, 2.4 Hz, 1H) 7.28 (d, J=2.4 Hz, 1H) 7.19 (d, J=12 Hz, 2H) 7.13

(s, 1H) 6.95 (d, J=4.8 Hz, 1H) 3.62 (s, 3H) 2.90 (t, J=8 Hz, 2H) 2.63 (s, 3H) 2.56 (t, J=8 Hz, 2H). MS: m/z=473.0 (M⁺+1).

Example 91

Synthesis of N-[4-Chloro-2-(2-methyl-1-oxy-pyridine-4-carbonyl)-phenyl]-4-trifluoromethoxy-benzenesulfonamide

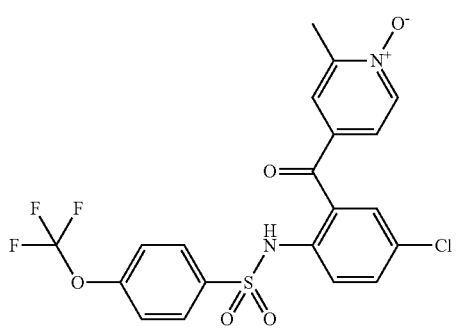

The title compound was prepared by the mCPBA oxidation of N-[4-Chloro-2-(2-methyl-pyridine-4-carbonyl)-phenyl]-4-trifluoromethoxy-benzenesulfonamide according to the general procedure and purified by HPLC. 1H NMR (CDCl3) δ 9.66 (s, 1H) 8.26 (d, J=6.8 Hz, 1H) 7.89 (d, 2H, J=8.4 Hz) 7.85 (s, 1H) 7.81 (d, 2H, J=8.4 Hz) 7.73 (d, 1H, J=8.8 Hz) 7.54 (dd, 1H, J=12 Hz, 2 Hz) 7.36 (t, 1H, J=5.6 Hz, 3.2 Hz) 7.24-7.19 (m, 1H) 2.55 (s, 3H). MS (ES) m/z=486.9 (M⁺+1).

Example 92

Synthesis of N-[4-Chloro-2-(2-methyl-1-oxy-pyridine-4-carbonyl)-phenyl]-4-isopropoxy-benzenesulfonamide

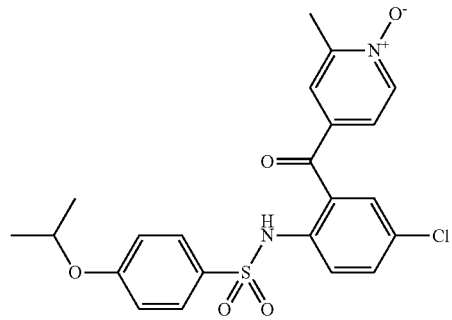

The title compound was prepared by the mCPBA oxidation of N-[4-Chloro-2-(2-methyl-pyridine-4-carbonyl)-phenyl]-4-isopropoxy-benzenesulfonamide according to the general procedure and purified by HPLC. 1H NMR (CDCl3) δ 9.39 (s, 1H) 8.32 (d, J=6.8 Hz, 1H) 7.75 (d, J=11.2, 1H) 7.57-7.52 (m, 3H) 7.36 (d, J=2.4 Hz, 1H) 7.30 (d, J=2.4 Hz, 1H) 7.21 (dd, J=7.2 Hz, 2.8 Hz, 1H) 6.71 (d, J=7.2 Hz, 2H) 4.46 (p, J=6.0 Hz, 1H) 2.57 (s, 3H) 1.29 (d, J=5.6 Hz, 6H). MS (ES) m/z=461.0 (M++1).

Example 93

Synthesis of N-[4-Chloro-2-(pyridine-4-carbonyl)-phenyl]-4-iodo-benzenesulfonamide

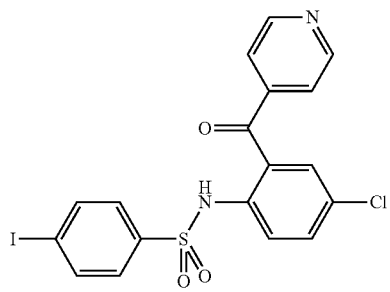

To a magnetically stirred mixture of precursor amino-ketone (2.32 g, 10.0 mmol) in dry pyridine (20 mL) was added a solution of pipsyl chloride (4.78 g, 15.8 mmol) in toluene (20 mL) under dry nitrogen. The addition was performed over a 2 h period. The reaction was stirred overnight at 50° C., then additional pipsyl chloride (850 mg), as a solution in toluene, was added. After 6 h, the reaction was concentrated and the residue was taken up in ethyl acetate. The organic layer was washed with water, then the mixture was filtered. The layers were separated and the organic layer was dried (MgSO₄), filtered and concentrated to provide crystalline material. ¹H-NMR (CDCl3) δ 9.95 (br s, 1H, NH), 8.82 (dm, 2H, J=5.2 Hz), 7.76 (d, 1H, J=8.8 Hz), 7.54 (dm, 1H, J=8.8 Hz, J=2.6 Hz), 7.41 (dm, 2H, J=8.8 Hz), 7.30 (d, 1H, J=2.6 Hz), 7.30 (d, 1H, J=2.6 Hz), 7.19 (dm, 2H, J=5.2 Hz). MS: m/z 499 (M+1).

Example 94

Synthesis of N-[4-Chloro-2-(pyridine-4-carbonyl)-phenyl]-4-(2,4-dimethyl-oxazol-5-yl)-benzenesulfonamide

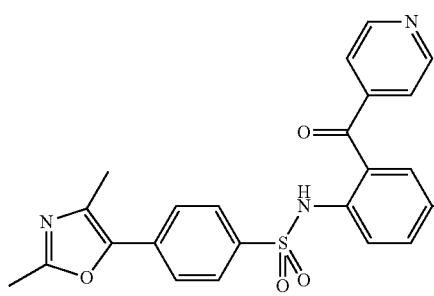

Trifluoromethanesulfonic acid (4.5 mmol) was added to a stirred solution of iodobenzene diacetate (0.39 g, 1.2 mmol) in acetonitrile (10 mL) and stirred at ambient temperature for 20 minutes. To this reaction propiophenone (1.0 mmol) was added and the reaction was refluxed for 2.5 h. After completion of the reaction, as judged by TLC, excess acetonitrile was evaporated and the crude product was extracted into dichloromethane (3×40 mL). The combined organic extracts were then washed with saturated aqueous sodium bicarbonate (2×50 mL), dried (MgSO4), filtered and concentrated to give a dark amber waxy solid. The product was purified by column chromatography on silica gel using ethyl acetate-hexane (5:95, 10:90) to furnish a crystalline solid.

2,4-dimethyl-5-phenyloxazole (53 mg, 0.31 mmol) was treated with chlorosulfonic acid (3.0 equivalents) in dry dichloromethane (8 mL) at 0° C. The solution was allowed to slowly warm to room temperature and monitored by LC/MS for complete reaction, then the reaction was washed with cold water. The organic layer was dried over magnesium sulfate, filtered and concentrated.

The residue was treated with thionyl chloride (2 equivalents) in dry dichloromethane (5 mL). The desired product was isolated by concentration of the reaction mixture to give 4-(2,4-dimethyl-oxazol-5-yl)benzenesulfonyl chloride, which was used immediately in the next step: mass spectrum m/z 272 (M+1);

To a magnetically stirred solution of the aminoketone (1.62 g, 7.0 mmol) in dry pyridine (30 mL) was added drop wise a solution of the sulfonyl chloride in 1.0 mL of dichloromethane and the slightly turbid reaction was stirred at ambient temperature. After 5 h, the reaction was diluted with ethyl acetate (25 mL) and washed with cold 3M HCl, followed by washing with aqueous NaHCO$_3$, then washed with water. The organic layer was dried (MgSO4), filtered and concentrated to give a pale yellow waxy solid. The product was purified by preparative hplc and pure material lyophilized to give the desired product. $^1$H NMR (CDCl3) δ 8.84 (br s, 2H), 7.69 (dm, 2H, J=8.4 Hz), 7.65 (d, 1H, J=8.8 Hz), 7.46 (dm, 1H, J=2.2 Hz), 7.43 (dm, 2H, J=8.4 Hz), 7.36 (ddd, 1H, J=8.8 Hz, J=2.6 Hz, J=0.7 Hz), 7.24 (2H, obscured), 7.15 (br s, 1H), 3.19 (s, 3H), 3.13 (s, 3H). MS: m/z 468 (M+1).

Example 95

Synthesis of 4-tert-Butyl-N-[4-chloro-2-(2-methyl-pyridine-3-carbonyl)-phenyl]-benzenesulfonamide

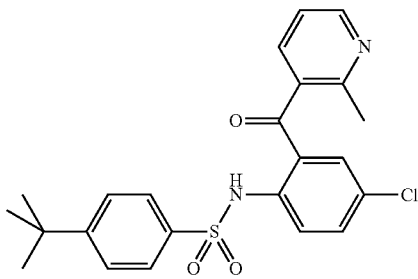

The title compound was prepared according to the general procedure for the synthesis of N-Aryl-benzenesulfonamides previously described using (2-Amino-5-chloro-phenyl)-(2-methyl-pyridin-3-yl)-methanone (243 mg, 1.0 mmol) and 4-tert-Butyl-benzenesulfonyl chloride (232 mg, 1.0 mmol) and purified by HPLC. $^1$H NMR (CDCl3) δ 10.71 (br s, 1H, NH), 8.63 (dd, 1H, J=5.1 Hz, J=1.6 Hz), 7.83 (d, 1H, J=8.8 Hz), 7.73 (dm, 2H, J=8.4 Hz), 7.49 (dd, 1H, J=8.8 Hz, J=2.6 Hz), 7.43 (dm, 2H, J=8.5 Hz), 7.27 (dd, 1H, J=9.5 Hz, J=1.8 Hz), 7.18 (dd, 1H, J=7.7 Hz, J=4.8 Hz), 7.13 (d, 1H, J=2.6 Hz), 2.29 (s, 3H), 1.29 (s, 9H). MS: m/z 443 (M+1).

Example 96

Synthesis of 4-tert-Butyl-N-[4-chloro-2-(2-methyl-1-oxy-pyridine-3-carbonyl)-phenyl]-benzenesulfonamide

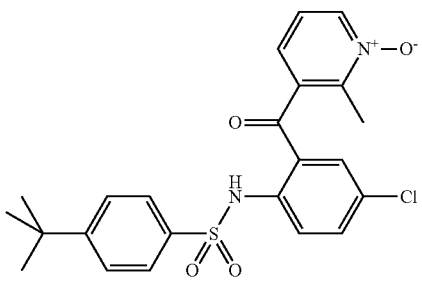

The title compound was prepared by the mCPBA oxidation of 4-tert-Butyl-N-[4-chloro-2-(2-methyl-pyridine-3-carbonyl)-phenyl]-benzenesulfonamide according to the general procedure. $^1$H NMR (CDCl$_3$) δ 10.71 (br s, 1H, NH), 8.62 (dm, 1H, J=5.9 Hz), 7.81 (d, 1H, J=9.1 Hz), 7.78 (dm, 2H, J=8.4 Hz), 7.54 (dd, 1H, J=8.8 Hz, J=2.6 Hz), 7.48 (dm, 2H, J=8.4 Hz), 7.44 (m, 2H), 7.18 (d, 1H, J=2.6 Hz), 2.32 (s, 3H), 1.32 (s, 9H). MS: m/z 459 (M+1).

Example 97

Synthesis of N-[4-Chloro-2-(2-methyl-pyridine-3-carbonyl)-phenyl]-4-isopropoxy-benzenesulfonamide

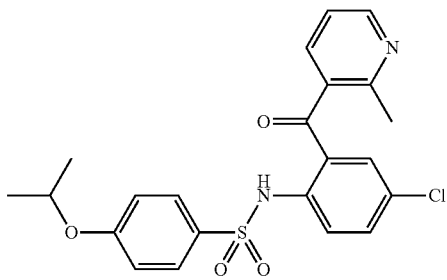

The title compound was prepared according to the general procedure for the synthesis of N-Aryl-benzenesulfonamides previously described using (2-amino-5-chloro-phenyl)-(2-methyl-pyridin-3-yl)-methanone and 4-isopropoxy-benzenesulfonyl chloride and purified by HPLC. $^1$H NMR (CDCl3) δ 10.63 (br s, 1H, NH), 8.63 (dd, 1H, J=4.8 Hz, J=1.8 Hz), 7.79 (d, 1H, J=8.8 Hz), 7.71 (d, 1H, J=8.8 Hz), 7.48 (dd, 1H, J=9.0 Hz, J=2.2 Hz), 7.27 (dd, 1H, J=7.7 Hz, J=1.8 Hz), 7.19 (dd, 1H, J=7.7 Hz, J=4.8 Hz), 7.14 (d, 1H, J=2.2 Hz), 4.55 (septet, 1H, J=6 Hz), 2.35 (s, 3H), 1.35 (d, 3H, J=6 Hz). MS: m/z 445 (M+1).

Example 98

Synthesis of N-[4-Chloro-2-(2-methyl-pyridine-3-carbonyl)-phenyl]-4-trifluoromethoxy-benzenesulfonamide

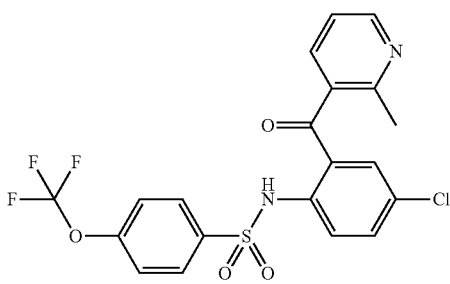

The title compound was prepared according to the general procedure for the synthesis of N-Aryl-benzenesulfonamides previously described using (2 amino-5-chloro-phenyl)-(2-methyl-pyridin-3-yl)-methanone and 4-trifluoromethoxy-benzenesulfonyl chloride and purified by HPLC.

$^1$H NMR (CDCl3) δ 10.76 (br s, 1H, NH), 8.65 (dd, 1H, J=4.8 Hz, J=2.0 Hz), 7.88 (dm, 2H, J=8.8 Hz), 7.80 (d, H1, J=9.2 Hz), 7.52 (dd, 1H, J=9.0 Hz, J=2.2 Hz), 7.1-7.3 (m, 4H), 7.18 (d, 1H, J=2.6 Hz), 2.35 (s, 3H). MS: m/z 471 (M+1).

Example 99

Synthesis of 4-Acetyl-N-[4-chloro-2-(2-methyl-pyridine-3-carbonyl)-phenyl]-benzenesulfonamide

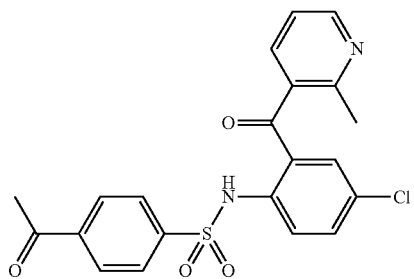

The title compound was prepared according to the general procedure for the synthesis of N-Aryl-benzenesulfonamides previously described using (2 amino-5-chloro-phenyl)-(2-methyl-pyridin-3-yl)-methanone and 4-acetyl-benzenesulfonyl chloride and purified by HPLC. $^1$H NMR (CDCl3) δ 10.79 (br s, 1H, NH), 8.65 (dd, 1H, J=4.8 Hz, J=1.8 Hz), 7.98 (d, 2H, J=8.8 Hz), 7.92 (d, 2H, J=8.8 Hz), 7.79 (d, 1H, J=9.2 Hz), 7.50 (dd, 1H, J=9.0 Hz, J=2.2 Hz), 7.22 (dd, 1H, J=7.7 Hz, J=1.5 Hz), 7.16 (m, 2H), 2.60 (s, 3H), 2.36 (s, 3H). MS: m/z 429 (M+1).

Example 100

Synthesis of N-[4-Chloro-2-(2-methyl-pyridine-3-carbonyl)-phenyl]-4-methanesulfonyl-benzenesulfonamide

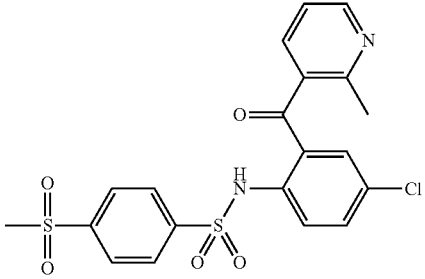

The title compound was prepared according to the general procedure for the synthesis of N-Aryl-benzenesulfonamides previously described using (2 amino-5-chloro-phenyl)-(2-methyl-pyridin-3-yl)-methanone and 4-methanesulfonyl-benzenesulfonyl chloride and purified by HPLC. $^1$H NMR (CDCl3) δ 10.86 (br s, 1, NH), 8.65 (dd, 1H, J=4.8 Hz, J=1.8 Hz), 8.02 (m, 4H), 7.78 (d, 1H, J=8.8 Hz), 7.53 (dd, 1H, J=8.8 Hz, J=2.6 Hz), 7.1-7.3 (m, 3H), 3.07 (s, 3H), 2.41 (s, 3H). MS: m/z 465 (M+1).

Example 101

Synthesis of 3-{4-[4-Chloro-2-(2-methyl-pyridine-3-carbonyl)-phenylsulfamoyl]-phenyl}-propionic acid methyl ester

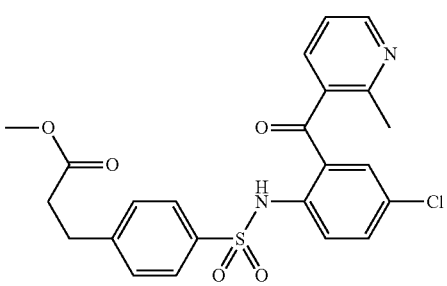

The title compound was prepared according to the general procedure for the synthesis of N-Aryl-benzenesulfonamides previously described using (2 amino-5-chloro-phenyl)-(2-methyl-pyridin-3-yl)-methanone and 3-(4-Chlorosulfonyl-phenyl)-propionic acid methyl ester and purified by HPLC. $^1$H-NMR (CDCl3) δ 10.75 (br s, 1H, NH), 8.64 (dm, 1H, J=4.8 Hz), 7.79 (dd, 1H, J=9.2 Hz, J=1.1 Hz), 7.75 (d, 2H, J=7.3 Hz), 7.49 (dm, 1H, J=9.2 Hz), 7.1-7.3 (m, 5H), 3.65 (s, 3H), 2.97 (t, 2H, J=7.6 Hz), 2.61 (t, 2H, J=7.6 Hz), 2.35 (s, 3H). MS: m/z 473 (M+1).

Example 102

Synthesis of N-[4-Chloro-2-(2-methyl-1-oxy-pyridine-3-carbonyl)-phenyl]-4-trifluoromethoxy-benzenesulfonamide

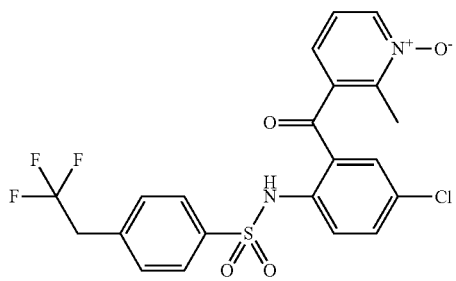

The title compound was prepared by the mCPBA oxidation of N-[4-Chloro-2-(2-methyl-pyridine-3-carbonyl)-phenyl]-4-trifluoromethoxy-benzenesulfonamide according to the general procedure. $^1$H NMR (CDCl3) δ 10.68 (br s, 1H, NH), 8.54 (dm, 1H, J=6.6 Hz), 7.92 (dm, 2H, J=8.8 Hz), 7.78 (d, 1, J=8.8 Hz), 7.56 (dd, 1, J=8.8 Hz, J=2.2 Hz), 7.45-7.15 (m, 4), 7.18 (d, 1, J=2.6 Hz), 2.33 (s, 3H). MS: m/z 487 (M+1).

Example 103

Synthesis of N-[4-Chloro-2-(2-methyl-1-oxy-pyridine-3-carbonyl)-phenyl]-4-isopropoxy-benzenesulfonamide

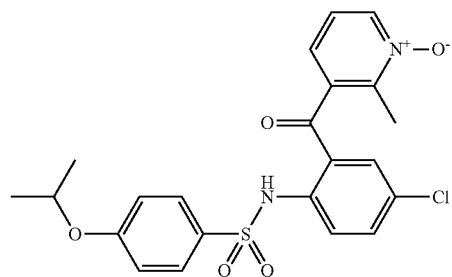

The title compound was prepared by the mCPBA oxidation of N-[4-chloro-2-(2-methyl-pyridine-3-carbonyl)-phenyl]-4-isopropoxy-benzenesulfonamide according to the general procedure. $^1$H NMR (CDCl3) δ 10.56 (br s, 1H, NH), 8.56 (dm, 1H, J=6.6 Hz), 7.79 (d, 1H, J=8.8 Hz), 7.75 (d, 2H, J=8.8 Hz), 7.53 (dd, 1H, J=8.8 Hz, J=2.6 Hz), 7.39 (t, 1H, J=7.2 Hz), 7.21 (d, 1H, J=8.0 Hz), 7.17 (d, 1H, J=2.6 Hz), 6.87 (d, 2H, J=8.8 Hz), 4.58 (septet, 1H, J=6 Hz), 2.32 (s, 3H), 1.35 (d, 3H, J=6 Hz). MS: m/z 461 (M+1).

Example 104

Synthesis of 4-Acetyl-N-[4-chloro-2-(2-methyl-1-oxy-pyridine-3-carbonyl)-phenyl]-benzenesulfonamide

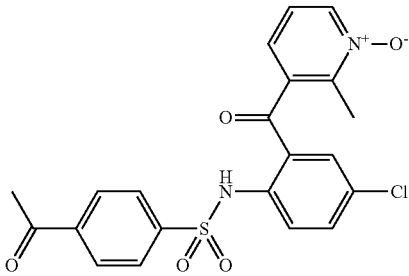

The title compound was prepared by the mCPBA oxidation of 4-Acetyl-N-[4-chloro-2-(2-methyl-pyridine-3-carbonyl)-phenyl]-benzenesulfonamide according to the general procedure. $^1$H NMR (CDCl3) δ 10.7 (br s, 1H, NH), 8.54 (d, 1H, J=6.6 Hz), 8.02 (d, 2H, J=8.4 Hz), 7.95 (d, 2H, J=8.4 Hz), 7.76 (d, 1H, J=8.8 Hz), 7.54 (dd, 1H, J=8.8 Hz, J=2.2 Hz), 7.38 (m, 1H), 7.22 (d, 1H, J=2.6 Hz), 7.16 (dm, 1H, J=7.7 Hz), 2.62 (s, 3H), 2.33 (s, 3H). MS: m/z 445 (M+1).

Example 105

Synthesis of N-[4-Chloro-2-(2-methyl-1-oxy-pyridine-3-carbonyl)-phenyl]-4-methanesulfonyl-benzenesulfonamide

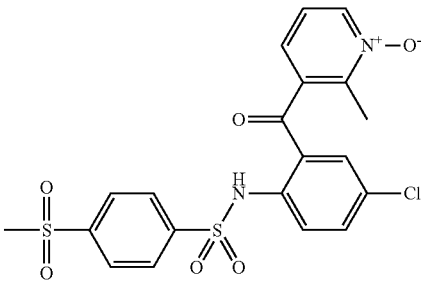

The title compound was prepared by the mCPBA oxidation of N-[4-Chloro-2-(2-methyl-pyridine-3-carbonyl)-phenyl]-4-methanesulfonyl-benzenesulfonamide according to the general procedure. $^1$H NMR (CDCl3) δ 10.78 (br s, 1H, NH), 8.38 (dm, 1H, J=6.6 Hz), 8.05 (s, 4H), 7.76 (d, 1H, J=8.8 Hz), 7.55 (dd, 1H, J=8.8 Hz, J=2.2 Hz), 7.25 (m, 1H), 7.22 (d, 1H, J=2.2 Hz), 6.76 (dm, 1H, J=7.7 Hz), 3.09 (s, 3H), 2.32 (s, 3H). MS: m/z 481 (M+1).

Example 106

Synthesis of 3-{4-[4-Chloro-2-(2-methyl-1-oxy-pyridine-3-carbonyl)-phenylsulfamoyl]-phenyl}-propionic acid methyl ester

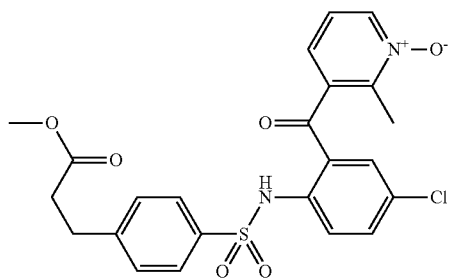

The title compound was prepared by the mCPBA oxidation of 3-{4-[4-Chloro-2-(2-methyl-pyridine-3-carbonyl)-phenylsulfamoyl]-phenyl}-propionic acid methyl ester according to the general procedure. $^1$H NMR (CDCl3) δ 10.66 (br s, 1H, NH), 8.54 (dm, 1H, J=6.2 Hz), 7.78 (m, 3H), 7.52 (dd, 1H, J=8.8 Hz, J=2.2 Hz), 7.39 (t, 1H, J=7.2 Hz), 7.31 (d, 2H, J=8.0 Hz), 7.18 (m, 2H), 3.65 (s, 3H), 2.99 (t, 2H, J=7.6 Hz), 2.64 (t, 2H, J=7.6 Hz), 2.31 (s, 3H). MS: m/z 489 (M+1).

Example 107

Synthesis of 4-tert-Butyl-N-[4-chloro-2-(6-methyl-pyridine-3-carbonyl)-phenyl]-benzenesulfonamide

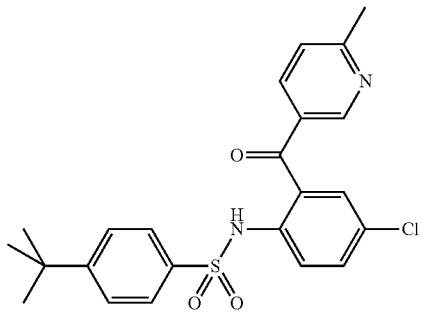

The title compound was prepared according to the general procedure for the synthesis of N-Aryl-benzenesulfonamides previously described using (2-Amino-5-chloro-phenyl)-(6-methyl-pyridin-3-yl)-methanone and 4-tert-butyl-benzenesulfonyl chloride and purified by HPLC. $^1$H NMR (CDCl$_3$) δ 9.77 (br s, 1H, NH), 8.40 (dm, 1H, J=1.8 Hz), 7.77 (dm, 1H, J=8.6 Hz), 7.71 (dd, 1H, J=8.1 Hz, J=2.2 Hz), 7.58 (dm, 2H, J=8.6 Hz), 7.50 (dd, 1H, J=9.0 Hz, J=2.4 Hz), 7.32 (d, 1H, J=2.2 Hz), 7.29 (dm, 2H, J=8.6 Hz), 7.23 (d, 1H, J=8.1 Hz), 2.63 (s, 3H), 1.20 (s, 9H). MS: m/z 443 (M+1).

Example 108

Synthesis of 4-tert-Butyl-N-[4-chloro-2-(6-methyl-1-oxy-pyridine-3-carbonyl)-phenyl]-benzenesulfonamide

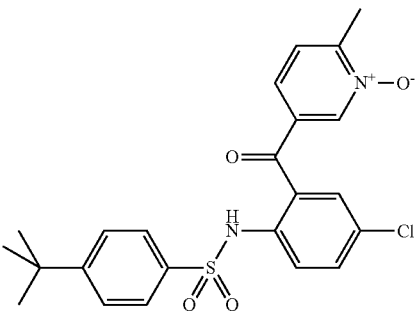

The title compound was prepared by the mCPBA oxidation of 4-tert-butyl-N-[4-chloro-2-(6-methyl-pyridine-3-carbonyl)-phenyl]-benzenesulfonamide according to the general procedure. $^1$H NMR (CDCl$_3$) δ 9.64 (br s, 1H, NH), 8.47 (m, 1H), 7.68 (d, 1H, J=8.8 Hz), 7.66 (d, 2H, J=8.8 Hz), 7.64 (m, 1H), 7.53 (m, 2H), 7.41 (d, 1H, J=2.2 Hz), 7.40 (d, 2H, J=8.8 Hz), 2.69 (s, 3H), 1.26 (s, 9H). MS: m/z 459 (M+1).

Example 109

Synthesis of N-[4-Chloro-2-(6-methyl-pyridine-3-carbonyl)-phenyl]-4-trifluoromethoxy-benzenesulfonamide

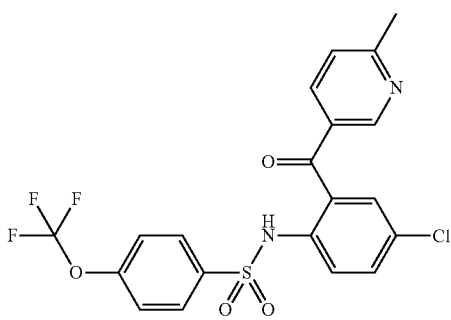

The title compound was prepared according to the general procedure for the synthesis of N-Aryl-benzenesulfonamides previously described using (2-Amino-5-chloro-phenyl)-(6-methyl-pyridin-3-yl)-methanone and 4-trifluoromethyl-benzenesulfonyl chloride and purified by HPLC. $^1$H-NMR (CDCl3) δ 9.76 (br s, 1, NH), 8.50 (d, 1H, J=2.2 Hz), 7.76 (d, 1H, J=8.8), 7.73 (d, 2H, J=9.2), 7.66 (dd, 1H, J=8.0, J=2.2), 7.54 (ddm, 1H, J=8.8 Hz, J=2.6 Hz), 7.37 (d, 1H, J=2.6), 7.24 (d, 1H, J=6 Hz), 7.10 (d, 2H, J=8.8 Hz), 2.35 (s, 3). MS: m/z 471 (M+1).

Example 110

Synthesis of N-[4-Chloro-2-(6-methyl-pyridine-3-carbonyl)-phenyl]-4-isopropoxy-benzenesulfonamide

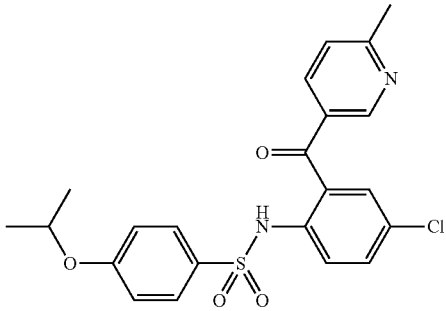

The title compound was prepared according to the general procedure for the synthesis of N-Aryl-benzenesulfonamides previously described using (2-Amino-5-chloro-phenyl)-(6-methyl-pyridin-3-yl)-methanone and 4-isopropoxy-benzenesulfonyl chloride and purified by HPLC. $^1$H NMR (CDCl$_3$) δ 9.67 (br s, 1H, NH), 8.45 (d, 1H, J=1.8 Hz), 7.75 (d, 1H, J=8.8 Hz), 7.68 (dd, 1H, J=8.0 Hz, J=2.2 Hz), 7.55 (d, 2H, J=9.0 Hz), 7.50 (dd, 1H, J=8.8 Hz, J=2.6 Hz), 7.32 (d, 1H, J=2.6 Hz), 7.24 (d, 1H, J=8.0 Hz), 6.68 (d, 2H, J=9.0 Hz), 4.43 (septet, 1H, J=6 Hz), 2.65 (s, 3H), 1.28 (d, 3H, J=6 Hz). MS: m/z 445 (M+1).

Example 111

Synthesis of 4-Acetyl-N-[4-chloro-2-(6-methyl-pyridine-3-carbonyl)-phenyl]-benzenesulfonamide

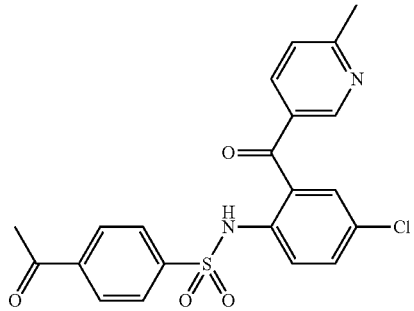

The title compound was prepared according to the general procedure for the synthesis of N-Aryl-benzenesulfonamides previously described using (2-Amino-5-chloro-phenyl)-(6-methyl-pyridin-3-yl)-methanone and 4-acetyl-benzenesulfonyl chloride and purified by HPLC. $^1$H NMR (CDCl$_3$) δ 9.54 (br s, 1, NH), 8.30 (m, 1), 7.77 (d, 2, J=8.8 Hz), 7.71 (d, 2, J=8.8 Hz), 7.69 (m, 1), 7.54 (dd, 1, J=8.8 Hz, J=2.2 Hz), 7.33 (d, 1, J=2.2 Hz); 7.26 (m, 1), 721 (d, 1, J=8.0 Hz), 2.63 (s, 3), 2.52 (s, 3). MS: m/z 429 (M+1).

Example 112

Synthesis of N-[4-Chloro-2-(6-methyl-pyridine-3-carbonyl)-phenyl]-4-methanesulfonyl-benzenesulfonamide

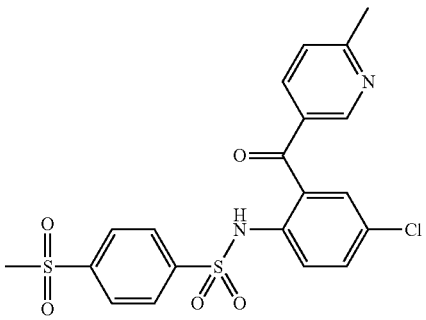

The title compound was prepared according to the general procedure for the synthesis of N-Aryl-benzenesulfonamides previously described using (2-Amino-5-chloro-phenyl)-(6-methyl-pyridin-3-yl)-methanone and 4-Methanesulfonyl-benzenesulfonyl chloride and purified by HPLC. $^1$H NMR (CDCl$_3$) δ 9.77 (br s, 1H, NH), 8.44 (dm, 1H, J=2.2 Hz), 7.87 (d, 2H, J=8.8 Hz), 7.83 (d, 2H, J=8.8 Hz), 7.76 (d, 1H, J=8.8 Hz), 7.60 (dd, 1H, J=8.0 Hz, J=2.2 Hz), 7.55 (dd, 1H, J=8.8 Hz, J=2.2 Hz), 7.36 (d, 1H, J=2.2), 7.26 (d, 1H, J=8.0 Hz), 3.00 (s, 3H), 2.66 (s, 3H). MS: m/z 465 (M+1).

Example 113

Synthesis of 3-{4-[4-Chloro-2-(6-methyl-pyridine-3-carbonyl)-phenylsulfamoyl]-phenyl}-propionic acid methyl ester

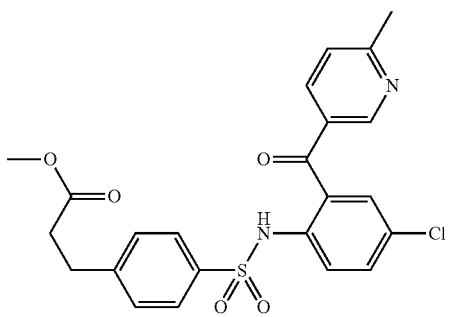

The title compound was prepared according to the general procedure for the synthesis of N-Aryl-benzenesulfonamides previously described using (2-Amino-5-chloro-phenyl)-(6-methyl-pyridin-3-yl)-methanone and 3-(4-Chlorosulfonyl-phenyl)-propionic acid methyl ester and purified by HPLC. $^1$H NMR (CDCl3) δ 9.66 (br s, 1H, NH), 8.34 (d, 1H, J=2.2 Hz), 7.75 (d, 1H, J=8.8 Hz), 7.72 (d, 1H, J=8.0 Hz, J=2.2 Hz), 7.56 (d, 2H, J=8.4 Hz), 7.51 (dd, 1H, J=8.8 Hz, J=2.2 Hz), 7.32 (d 1H, J=2.2 Hz), 7.26 (d, 1H, J=7 Hz), 7.09 (d, 2H, J=8.4

Hz), 3.65 (s, 3H), 2.97 (t, 2H, J=7.6 Hz), 2.66 (s, 3H), 2.51 (t, 2H, J=7.6 Hz). MS: m/z 473 (M+1).

Example 114

Synthesis of N-[4-Chloro-2-(6-methyl-1-oxy-pyridine-3-carbonyl)-phenyl]-4-trifluoromethoxy-benzenesulfonamide

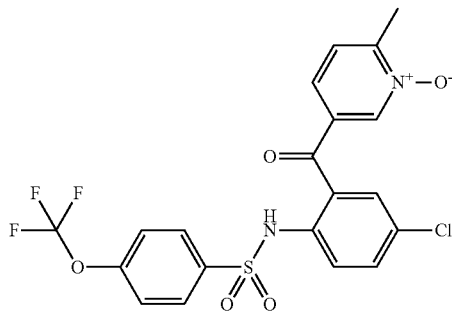

The title compound was prepared by the mCPBA oxidation of N-[4-Chloro-2-(6-methyl-pyridine-3-carbonyl)-phenyl]-4-trifluoromethoxy-benzenesulfonamide according to the general procedure. $^1$H NMR (CDCl3) δ 9.60 (br s, 1, NH), 8.42 (m, 1H), 7.78 (dm, 2H, J=8.4 Hz), 7.70 (dm, J=8.8 Hz), 7.56 (dd, 1H, J=8.0 Hz, J=2.2 Hz), 7.44 (d, 1H, J=8.0 Hz), 7.41 (d, 1H, J=2.2 Hz), 7.38 (dm, 1H, J=8.0 Hz), 7.20 (dm, 2H, J=8.4 Hz), 2.65 (s, 3H). MS: m/z 487 (M+1).

Example 115

Synthesis of N-[4-Chloro-2-(6-methyl-1-oxy-pyridine-3-carbonyl)-phenyl]-4-isopropoxy-benzenesulfonamide

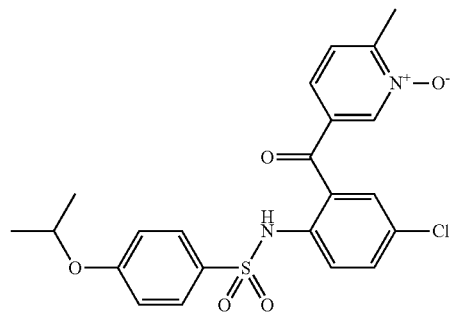

The title compound was prepared by the mCPBA oxidation of N-[4-Chloro-2-(6-methyl-pyridine-3-carbonyl)-phenyl]-4-isopropoxy-benzenesulfonamide according to the general procedure. $^1$H-NMR (CDCl$_3$) δ 9.53 (br s, 1H, NH), 8.25 (dm, 1H, J=1.5 Hz), 7.74 (d, 1H, J=8.8 Hz), 7.59 (dm, 2H, J=8.8 Hz), 7.52 (dd, 1H, J=8.8 Hz, J=2.6 Hz), 7.24 (d, 1H, J=8.0 Hz), 7.33 (d, 1H, J=2.6 Hz), 7.20 (dd, 1H, J=8.0 Hz, J=1.6 Hz), 6.75 (dm, 2H, J=8.8 Hz), 4.51 (septet, 1H, J=6 Hz), 2.59 (s, 3H), 1.30 (d, 3H, J=6 Hz). MS: m/z 461 (M+1).

Example 116

Synthesis of 4-Acetyl-N-[4-chloro-2-(6-methyl-1-oxy-pyridine-3-carbonyl)-phenyl]-benzenesulfonamide

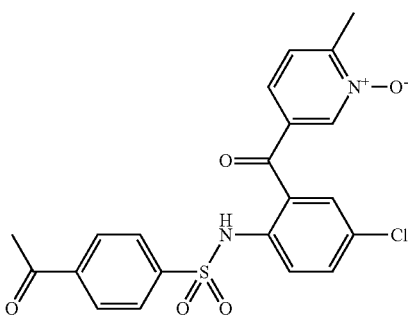

The title compound was prepared by the mCPBA oxidation of 4-Acetyl-N-[4-chloro-2-(6-methyl-pyridine-3-carbonyl)-phenyl]-benzenesulfonamide according to the general procedure. $^1$H-NMR (CDCl3) δ 9.16 (br s, 1H, NH), 8.15 (dm, 1H, J=2.0 Hz), 7.83 (d, 2H, J=8.1 Hz), 7.71 (d, 2H, J=8.1 Hz), 7.71-7.67 (m, 2H), 7.58 (dd, 1H, J=8.8 Hz, J=2.2 Hz), 7.52 (d, 1H, J=8.4 Hz), 7.37 (d, 1H, J=2.2 Hz), 2.66 (s, 3H), 2.60 (s, 3H). MS: m/z 445 (M+1).

Example 117

Synthesis of N-[4-Chloro-2-(6-methyl-1-oxy-pyridine-3-carbonyl)-phenyl]-4-methanesulfonyl-benzenesulfonamide

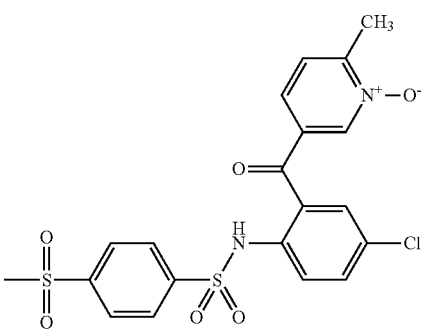

The title compound was prepared by the mCPBA oxidation of N-[4-Chloro-2-(6-methyl-pyridine-3-carbonyl)-phenyl]-4-methanesulfonyl-benzenesulfonamide according to the general procedure. $^1$H-NMR (CDCl3) δ 9.39 (br s, 1H, NH), 8.61 (m, 1H), 7.88 (m, 4H), 7.68 (d, 1H, J=8.8 Hz), 7.60 (m, 2H), 7.40 (m, 2H), 3.03 (s, 3H), 2.69 (s, 3H). m/z 481 (M+1)

Example 118

Synthesis of 3-{4-[4-Chloro-2-(6-methyl-1-oxy-pyridine-3-carbonyl)-phenylsulfamoyl]-phenyl}-propionic acid methyl ester

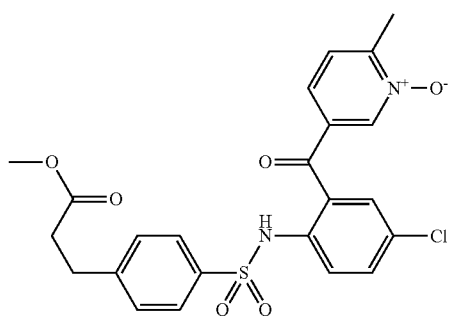

The title compound was prepared by the mCPBA oxidation of 3-{4-[4-Chloro-2-(6-methyl-pyridine-3-carbonyl)-phenylsulfamoyl]-phenyl}-propionic acid methyl ester according to the general procedure. $^1$H-NMR (CDCl3) δ 9.47 (br s, 1H, NH), 8.26 (m, 1H), 7.69 (d, 1H, J=8.8 Hz), 7.59 (dm, 2H, J=8.4 Hz), 7.53 (dd, 1H, J=8.8 Hz, J=2.6 Hz), 7.48 (m, 2H), 7.35 (d, 1H, J=2.6 Hz), 7.18 (dm, 2H, J=8.4 Hz), 3.64 (s, 3H), 2.88 (t, 2H, J=7.6 Hz), 2.67 (s, 3H), 2.51 (t, 2H, J=7.6 Hz). MS: m/z 489 (M+1).

Measuring Efficacy of CCR9 Modulators
In Vitro Assays

A variety of assays can be used to evaluate the compounds provided herein, including signaling assays, migration assays, and other assays of cellular response. CCR9 receptor signaling assays can be used to measure the ability of a compound, such as a potential CCR9 antagonist, to block CCR9 ligand- (e.g. TECK)-induced signaling. A migration assay can be used to measure the ability of a compound of interest, such as a possible CCR9 antagonist, to block CCR9-mediated cell migration in vitro. The latter is believed to resemble chemokine-induced cell migration in vivo.

In a suitable assay, a CCR9 protein (whether isolated or recombinant) is used which has at least one property, activity, or functional characteristic of a mammalian CCR9 protein. The property can be a binding property (to, for example, a ligand or inhibitor), a signaling activity (e.g., activation of a mammalian G protein, induction of rapid and transient increase in the concentration of cytosolic free calcium [$Ca^{++}$]), cellular response function (e.g., stimulation of chemotaxis or inflammatory mediator release by leukocytes), and the like.

The assay can be a cell based assay that utilizes cells stably or transiently transfected with a vector or expression cassette having a nucleic acid sequence which encodes the CCR9 receptor. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., TECK) as a competitor.

Binding inhibition assays can be used to evaluate the present compounds. In these assays, the compounds are evaluated as inhibitors of ligand binding using, for example, TECK. In this embodiment, the CCR9 receptor is contacted with a ligand such as TECK and a measure of ligand binding is made. The receptor is then contacted with a test agent in the presence of a ligand (e.g., TECK) and a second measurement of binding is made. A reduction in the extent of ligand binding is indicative of inhibition of binding by the test agent. The binding inhibition assays can be carried out using whole cells which express CCR9, or a membrane fraction from cells which express CCR9.

The binding of a G protein coupled receptor by, for example, an agonist, can result in a signaling event by the receptor. Accordingly, signaling assays can also be used to evaluate the compounds of the present invention and induction of signaling function by an agent can be monitored using any suitable method. For example, G protein activity, such as hydrolysis of GTP to GDP, or later signaling events triggered by receptor binding can be assayed by known methods (see, for example, PCT/US97/15915; Neote, et al., *Cell*, 72:415425 (1993); Van Riper, et al., *J. Exp. Med.*, 177:851-856 (1993) and Dahinden, et al., *J. Exp. Med.*, 179:751-756 (1994)).

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. A variety of chemotaxis assays are known in the art, and any suitable assay can be used to evaluate the compounds of the present invention. Examples of suitable assays include those described in PCT/US97/15915; Springer, et al., WO 94/20142; Berman et al., *Immunol. Invest.*, 17:625-677 (1988); and Kavanaugh at al., *J. Immunol.*, 146:4149-4156 (1991)).

Calcium signaling assays measure calcium concentration over time, preferably before and after receptor binding. These assays can be used to quantify the generation of a receptor signaling mediator, $Ca^{++}$, following receptor binding (or absence thereof). These assays are useful in determining the ability of a compound, such as those of the present invention, to generate the receptor signaling mediator by binding to a receptor of interest. Also, these assays are useful in determining the ability of a compound, such as those of the present invention, to inhibit generation of the receptor signaling mediator by interfering with binding between a receptor of interest and a ligand.

In calcium signaling assays used to determine the ability of a compound to interfere with binding between CCR9 and a known CCR9 ligand, CCR9-expressing cells (such as a T cell line MOLT-4 cells) are first incubated with a compound of interest, such as a potential CCR9 antagonist, at increasing concentrations. The cell number can be from $10^5$ to $5 \times 10^5$ cells per well in a 96-well microtiter plate. The concentration of the compound being tested may range from 0 to 100 uM. After a period of incubation (which can range from 5 to 60 minutes), the treated cells are placed in a Fluorometric Imaging Plate Reader (FLIPR®) (available from Molecular Devices Corp., Sunnyvale, Calif.) according to the manufacturer's instruction. The FLIPR system is well known to those skilled in the art as a standard method of performing assays. The cells are then stimulated with an appropriate amount of the CCR9 ligand TECK (e.g. 5-100 nM final concentration) and the signal of intracellular calcium increase (also called calcium flux) is recorded. The efficacy of a compound as an inhibitor of binding between CCR9 and the ligand can be calculated as an IC50 (the concentration needed to cause 50% inhibition in signaling) or IC90 (at 90% inhibition).

In vitro cell migration assays can be performed (but are not limited to this format) using the 96-well microchamber (called ChemoTX™). The ChemoTX system is well known to those skilled in the art as a type of chemotactic/cell migration instrument. In this assay, CCR9-expressing cells (such as MOLT-4) are first incubated with a compound of interest, such as a possible CCR9 antagonist, at increasing concentrations. Typically, fifty thousand cells per well are used, but the amount can range from $10^3$-$10^6$ cells per well. CCR9 ligand TECK, typically at 50 nM (but can range from 5-100 nM), is placed at the lower chamber and the migration apparatus is assembled. Twenty microliters of test compound-treated cells are then placed onto the membrane. Migration is allowed to take place at 37 C for a period of time, typically 2.5 hours. At the end of the incubation, the number of cells that migrated across the membrane into the lower chamber is then quantified. The efficacy of a compound as an inhibitor of CCR9-mediated cell migration is calculated as an IC50 (the concentration needed to reduce cell migration by 50%) or IC90 (for 90% inhibition).

In Vivo Efficacy Models for Human IBD

T cell infiltration into the small intestine and colon have been linked to the pathogenesis of human inflammatory bowel diseases which include Coeliac disease, Crohn's disease and ulcerative colitis. Blocking trafficking of relevant T cell populations to the intestine is believed to be an effective approach to treat human IBD. CCR9 is expressed on gut-homing T cells in peripheral blood, elevated in patients with small bowel inflammation such as Crohn's disease and Coeliac disease. CCR9 ligand TECK is expressed in the small intestine. It is thus believed that this ligand-receptor pair plays a role in IBD development by mediating migration of T cells to the intestine. Several animal models exist and can be used for evaluating compounds of interest, such as potential CCR9 antagonists, for an ability to affect such T cell migration and/or condition or disease, which might allow efficacy predictions of antagonists in humans.

Animal Models with Pathology Similar to Human Ulcerative Colitis

A murine model described by Panwala and coworkers (Panwala, et al., *J Immunol.*, 161(10):5733-44 (1998)) involves genetic deletion of the murine multi-drug resistant gene (MDR). MDR knockout mice (MDR−/−) are susceptible to developing a severe, spontaneous intestinal inflammation when maintained under specific pathogen-free facility conditions. The intestinal inflammation seen in MDR−/− mice has a pathology similar to that of human inflammatory bowel disease (IBD) and is defined by Th1 type T cells infiltration into the lamina propria of the large intestine.

Another murine model was described by Davidson et al., *J Exp Med.*, 184(1):241-51 (1986). In this model, the murine IL-10 gene was deleted and mice rendered deficient in the production of interleukin 10 (IL-10−/−). These mice develop a chronic inflammatory bowel disease (IBD) that predominates in the colon and shares histopathological features with human IBD.

Another murine model for IBD has been described by Powrie et al., *Int Immunol.*, 5(11):1461-71 (1993), in which a subset of CD4+ T cells (called CD45RB(high)) from immunocompetent mice are purified and adoptively transferred into immunodeficient mice (such as C.B-17 scid mice). The animal restored with the CD45RBhighCD4+ T cell population developed a lethal wasting disease with severe mononuclear cell infiltrates in the colon, pathologically similar with human IBD.

Murine Models with Pathology Similar to Human Crohn's Disease

The TNF ARE(−/−) model. The role of TNF in Crohn's disease in human has been demonstrated more recently by success of treatment using anti-TNF alpha antibody by Targan et al., *N Engl J Med.*, 337(15):1029-35 (1997). Mice with aberrant production of TNF-alpha due to genetic alteration in the TNF gene (ARE−/−) develop Crohn's-like inflammatory bowel diseases (see Kontoyiannis et al., *Immunity*, 10(3):387-98 (1999)).

The SAMP/yit model. This is model described by Kosiewicz et al., *J Clin Invest.*, 107(6):695-702 (2001). The mouse strain, SAMP/Yit, spontaneously develops a chronic inflammation localized to the terminal ileum. The resulting ileitis is characterized by massive infiltration of activated T lymphocytes into the lamina propria, and bears a remarkable resemblance to human Crohn's disease.

Example 119

This example illustrates the activity associated with representative compounds of the invention.
Materials and Methods (In Vitro Assays)
Reagents and Cells MOLT-4 cells were obtained from the American Type Culture Collection (Manassas, Va.) and cultured in RPMI tissue culture medium supplemented with 10% fetal calf serum (FCS) in a humidified 5% $CO_2$ incubator at 37° C. Recombinant human chemokine protein TECK was obtained from R&D Systems (Minneapolis, Minn.). ChemoTX® chemotaxis microchambers were purchased from Neuro Probe (Gaithersburg, Md.). CyQUANT® cell proliferation kits were purchased from Molecular Probes (Eugene, Oreg.). Calcium indicator dye Fluo-4 AM was purchased from Molecular Devices (Mountain View, Calif.).
Conventional Migration Assay Conventional migration assay was used to determine the efficacy of potential receptor antagonists in blocking migration mediated through CCR9. This assay was routinely performed using the ChemoTX® microchamber system with a 5-µm pore-sized polycarbonate membrane. To begin such an assay, MOLT-4 cells were harvested by centrifugation of cell suspension at 1000 PRM on a GS-6R Beckman centrifuge. The cell pellet was resuspended in chemotaxis buffer (HBSS with 0.1% BSA) at $5 \times 10^6$ cells/mL. Test compounds at desired concentrations were prepared from 10 mM stock solutions by serial dilutions in chemotaxis buffer. An equal volume of cells and compounds were mixed and incubated at room temperature for 15 minutes. Afterwards, 20 µl of the mixture was transferred onto the porous membrane of a migration microchamber, with 29 µL of 50 nM chemokine TECK protein placed at the lower chamber. Following a 150-minute incubation at 37° C., during which cells migrated against the chemokine gradient, the assay was terminated by removing the cell drops from atop the filter. To quantify cells migrated across the membrane, 5 µL of 7× CyQUANT® solution was added to each well in the lower chamber, and the fluorescence signal measured on a Spectrafluor Plus fluorescence plate reader (TECAN, Durham, N.C.). The degree of inhibition was determined by comparing migration signals between compound-treated and untreated cells. IC50 calculation was further performed by non-linear squares regression analysis using Graphpad Prism (Graphpad Software, San Diego, Calif.).
RAM Assay The primary screen to identify CCR9 antagonists was carried out using RAM assay (WO 02101350), which detects potential hits by their ability to activate cell migration under inhibitory TECK concentration. To begin such an assay, MOLT-4 cells were harvested by centrifugation of cell suspension at 1000 RPM on a GS-6R Beckman centrifuge. The cell pellet was resuspended in chemotaxis buffer (HBSS/ 0.1% BSA) at $5 \times 10^6$ cells/mL. Twenty-five microliters of cells was mixed with an equal volume of a test compound diluted to 20 µM in the same buffer. Twenty microliters of the mixture was transferred onto the filter in the upper chemotaxis chamber, with 29 µL of 500 nM chemokine protein TECK placed in the lower chamber. Following a 150-minute incubation at 37° C., the assay was terminated by removing the cell drops from atop the filter. To quantify cells migrated across the membrane, 5 µL of 7× CyQUANT® solution was added to each well in the lower chamber, and the fluorescence signal measured on a Spectrafluor Plus fluorescence plate reader (TECAN, Durham, N.C.).

For selection of potential hits, the level of migration activation was calculated as a RAM index—the ratio between the signal of a particular well and the median signal of the whole plate. Compounds with a RAM index of greater than 1.8 were regarded as RAM positive, and were selected for $IC_{50}$ determinations in conventional functional assays.

Calcium Flux Assay

Calcium flux assay measures an increase in intracellular calcium following ligand-induced receptor activation. In the screen of CCR9 antagonists, it was used as a secondary assay carried out on a FLIPR® machine (Molecular Devices, Mountain View, Calif.). To begin an assay, MOLT-4 cells were harvested by centrifugation of cell suspension, and resuspended to $1.5 \times 10^6$ cells/mL in HBSS (with 1% fetal calf serum). Cells were then labeled with a calcium indicator dye Fluo-4 AM for 45 minutes at 37° C. with gentle shaking. Following incubation, cells were pelletted, washed once with HBSS and resuspended in the same buffer at a density of $1.6 \times 10^6$ cells/mL. One hundred microliters of labeled cells were mixed with 10 µL of test compound at the appropriate concentrations on an assay plate. Chemokine protein TECK was added at a final concentration of 25 nM to activate the receptor. The degree of inhibition was determined by comparing calcium signals between compound-treated and untreated cells. IC50 calculations were further performed by non-linear squares regression analysis using Graphpad Prism (Graphpad Software, San Diego, Calif.).

Discovery of CCR9 Antagonists

The discovery of CCR9 antagonists was carried out in two steps: First, RAM assay was used to screen a compound library in a high-throughput manner. The assay detected compounds by their ability to cause a positive migration signal under RAM condition. Secondly, RAM positive compounds were tested to determine their $IC_{50}$s using the conventional migration and calcium flux assays.

For instance, in a screen of approximately 100,000 compounds, 2000 individual wells representing approximately 2% of total compounds showed a RAM index greater than 1.8. These compounds were cheery-picked and retested in duplicate wells by RAM assay. A total of 270 compounds, or 0.27% of the library, were confirmed RAM positives.

Since a RAM positive signal indicates only the presence of a receptor antagonist and not how strongly it blocks receptor functions, the RAM positive compounds were further tested for potency in calcium flux assay using MOLT-4 cells. $IC_{50}$ determinations on this subset discovered several compounds with $IC_{50}$'s less than 1 µM and that did not inhibit other chemokine receptors examined at significant levels.

In Vivo Efficacy Studies

The MDR1a-knockout mice, which lack the P-glycoprotein gene, spontaneously develop colitis under specific pathogen-free condition. The pathology in these animals has been characterized as Th1-type T cell-mediated inflammation similar to ulcerative colitis in humans. Disease normally begins to develop at around 8-10 weeks after birth. However the ages at which disease emerges and the ultimate penetrance level often vary considerably among different animal facilities.

In a study using the MDR1a-knockout mice, the CCR9 antagonist shown below

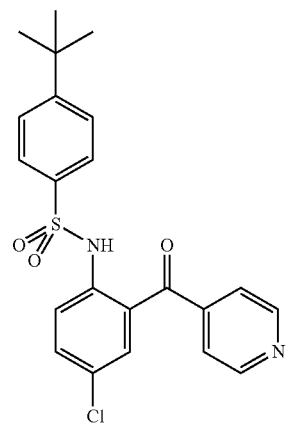

was evaluated by prophylactic administration for its ability to delay disease onset. Female mice (n=34) were dosed with 50 mg/kg twice a day by subcutaneous injections for 14 consecutive weeks starting at age 10 weeks. The study showed that the compound prevented IBD-associated growth retardation. Moreover, the number of mice developing diarrhea was also lower among compound-treated mice (17%), compared to mice receiving vehicle alone (24%) (FIG. 1).

In the table below, structures and activity are provided for representative compounds described herein. Activity is provided as follows for either or both of the chemotaxis assay and/or calcium mobilization assays, described above: + 1000 nM<$IC_{50}$<10000 nM; ++, 100 nM<$IC_{50}$<1000 nM; and +++, $IC_{50}$<100 nM.

TABLE 1

Compounds with activity in either or both of the chemotaxis assay and calcium mobilization assays, with $IC_{50}$ < 100 nM (+++)

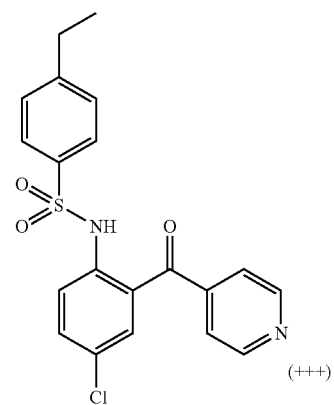

(+++)

TABLE 1-continued
Compounds with activity in either or both of the chemotaxis assay and calcium mobilization assays, with IC$_{50}$ < 100 nM (+++)
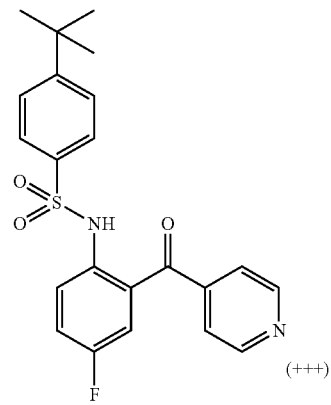
(+++)
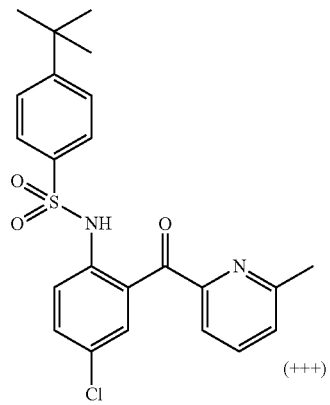
(+++)
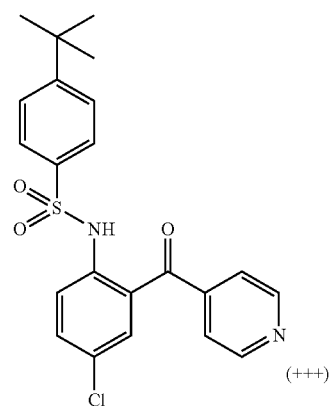
(+++)
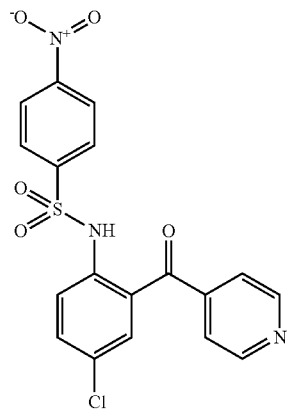
(+++)
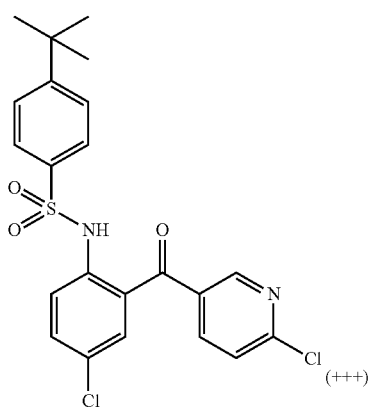
(+++)
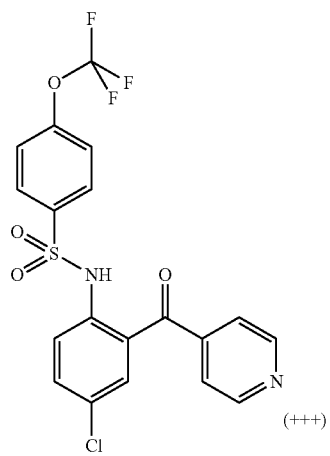
(+++)

TABLE 1-continued
Compounds with activity in either or both of the chemotaxis assay and calcium mobilization assays, with IC$_{50}$ < 100 nM (+++)
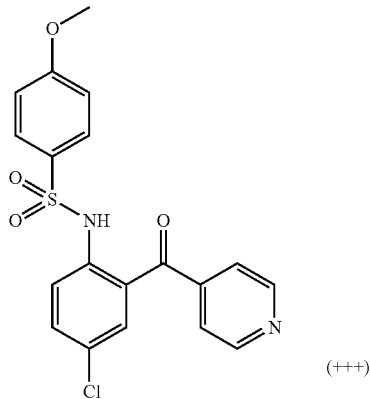
(+++)
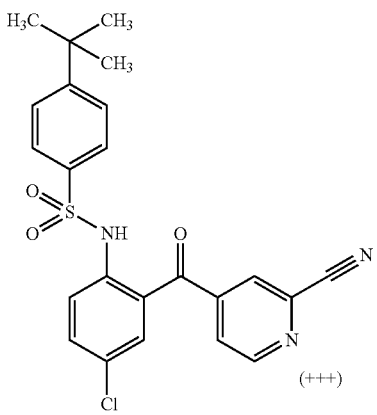
(+++)
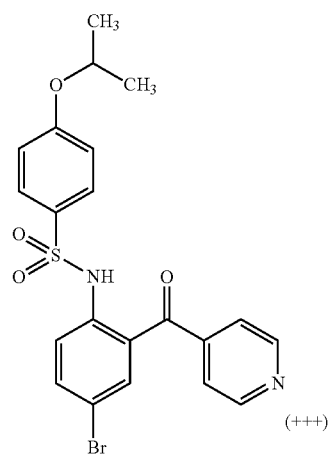
(+++)
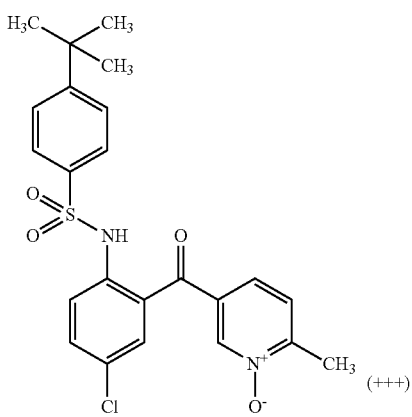
(+++)
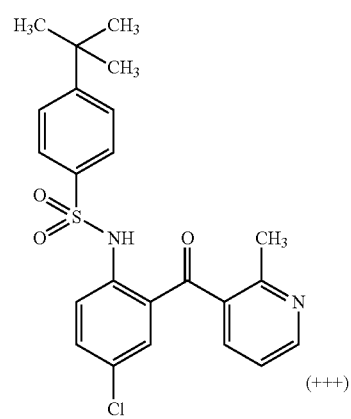
(+++)
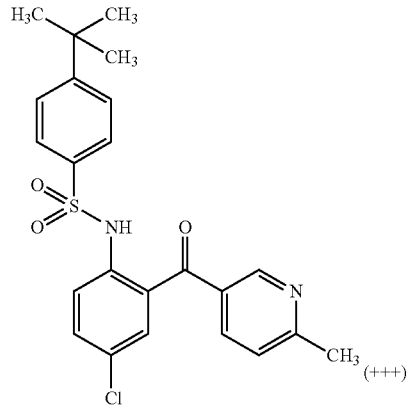
(+++)

TABLE 1-continued
Compounds with activity in either or both of the chemotaxis assay and calcium mobilization assays, with IC$_{50}$ < 100 nM (+++)
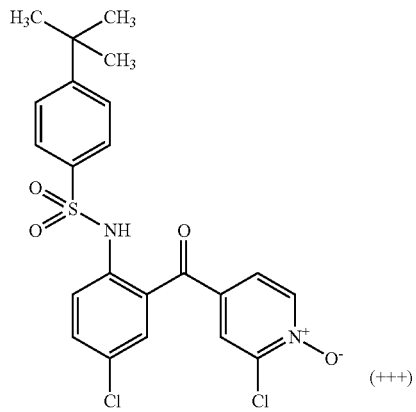
(+++)
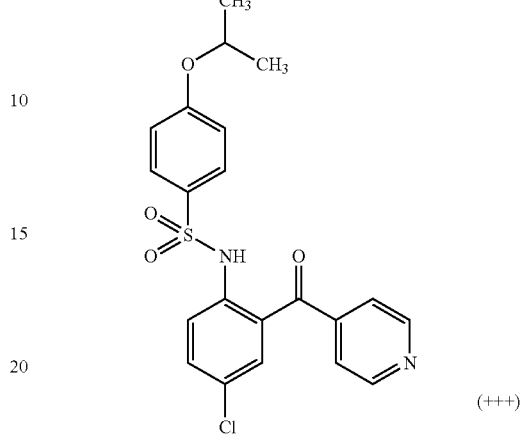
(+++)
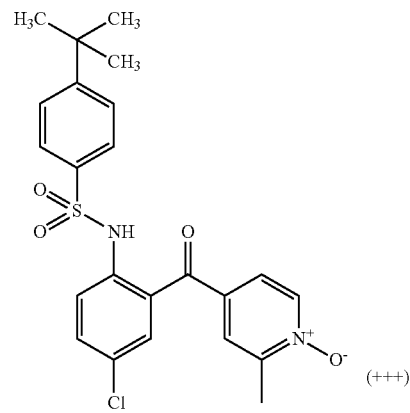
(+++)
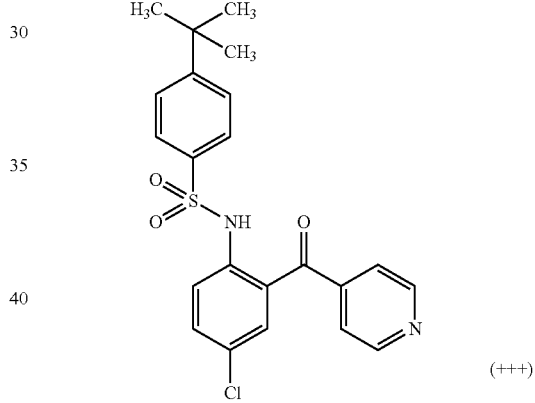
(+++)
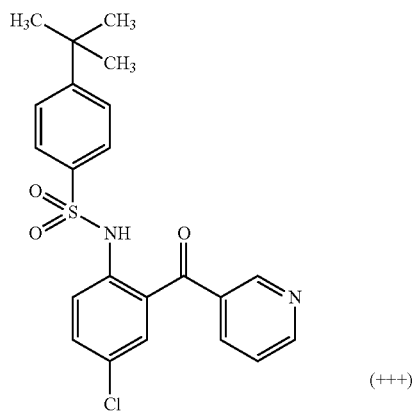
(+++)
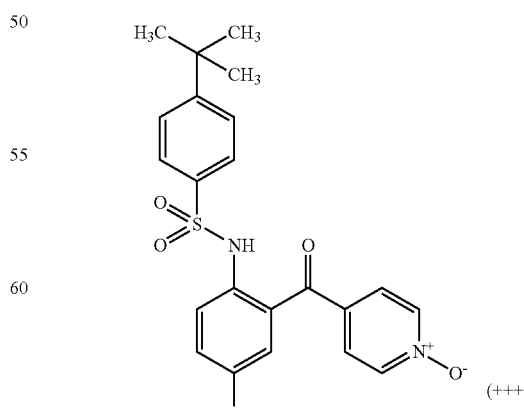
(+++)

TABLE 1-continued
Compounds with activity in either or both of the chemotaxis assay and calcium mobilization assays, with $IC_{50} < 100$ nM (+++)
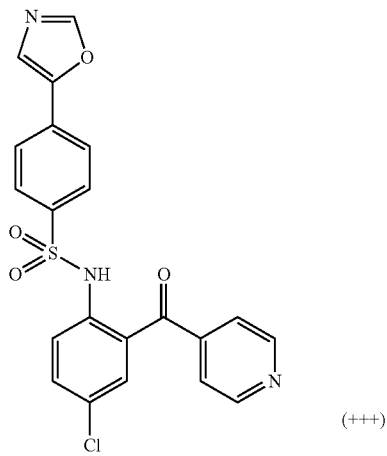
(+++)
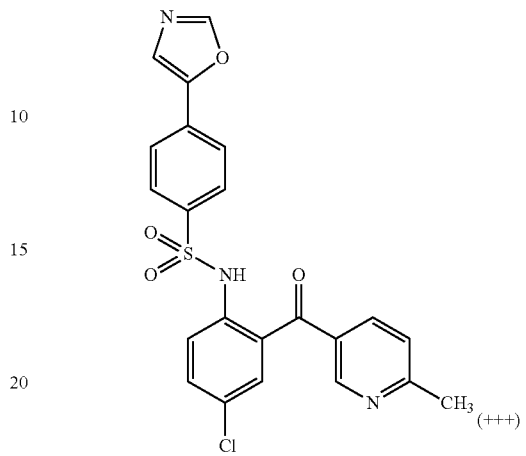
(+++)
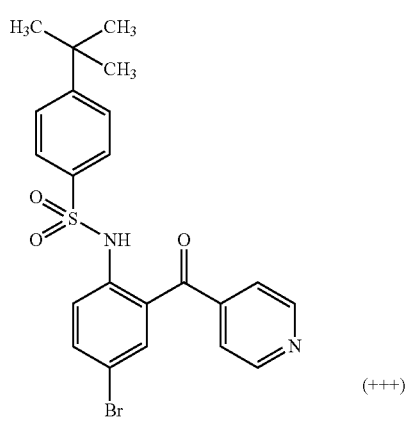
(+++)
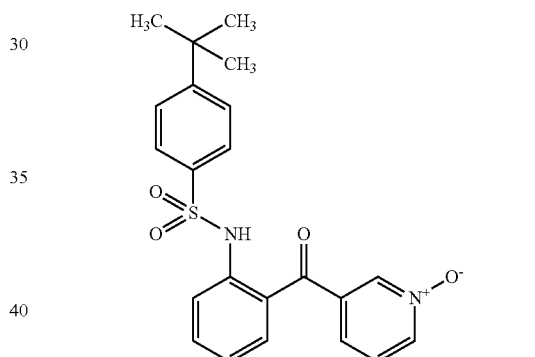
(+++)
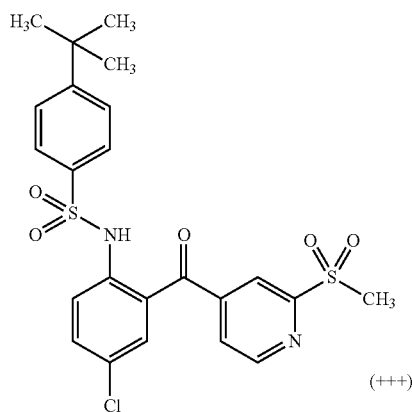
(+++)
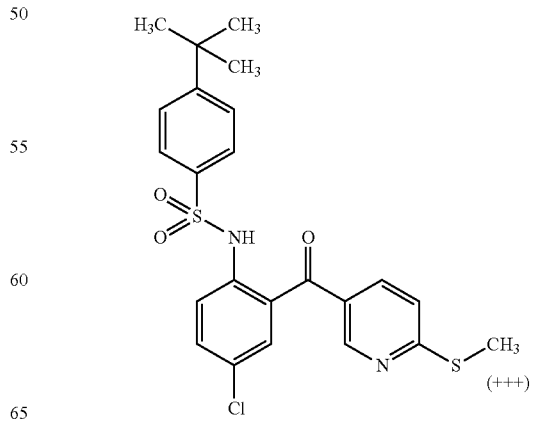
(+++)

TABLE 1-continued
Compounds with activity in either or both of the chemotaxis assay and calcium mobilization assays, with IC$_{50}$ < 100 nM (+++)
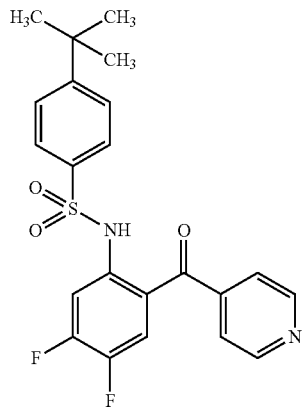
(+++)
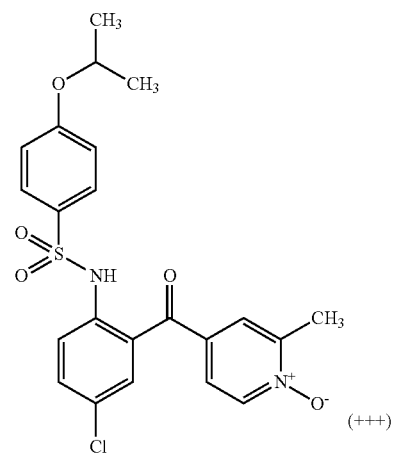
(+++)
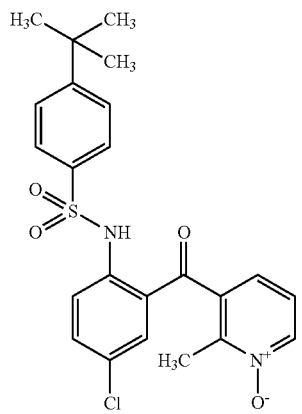
(+++)
TABLE 1-continued
Compounds with activity in either or both of the chemotaxis assay and calcium mobilization assays, with IC$_{50}$ < 100 nM (+++)
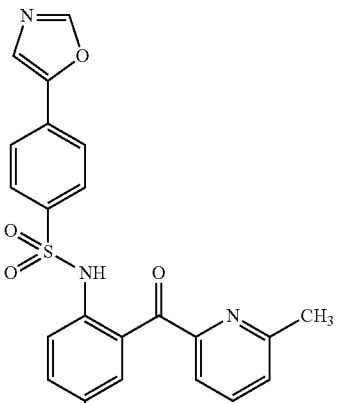
(+++)
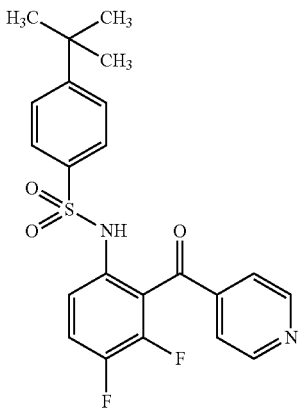
(+++)
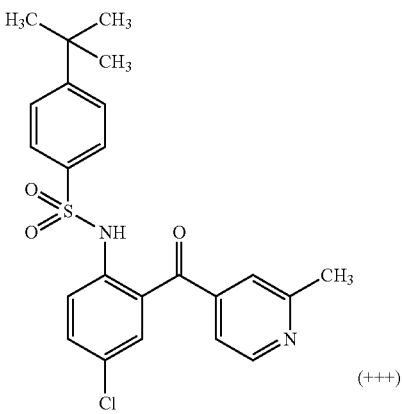
(+++)

TABLE 1-continued
Compounds with activity in either or both of the chemotaxis assay and calcium mobilization assays, with IC$_{50}$ < 100 nM (+++)
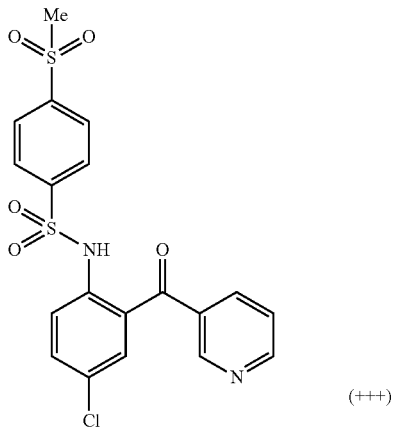
(+++)
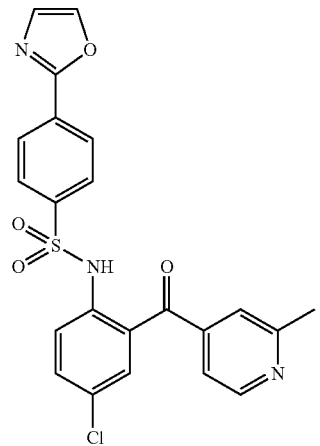
(+++)
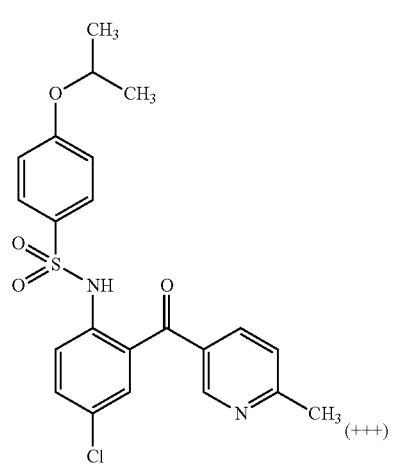
(+++)
TABLE 1-continued
Compounds with activity in either or both of the chemotaxis assay and calcium mobilization assays, with IC$_{50}$ < 100 nM (+++)
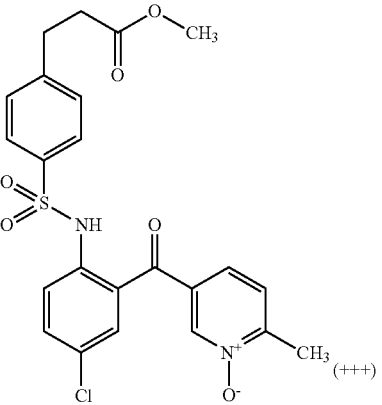
(+++)
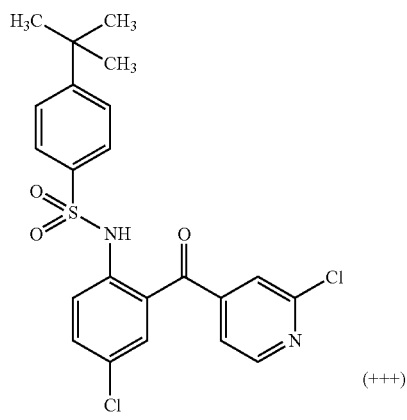
(+++)
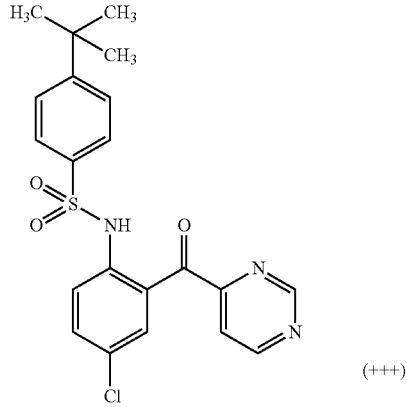
(+++)

TABLE 1-continued
Compounds with activity in either or both of the chemotaxis assay and calcium mobilization assays, with IC$_{50}$ < 100 nM (+++)
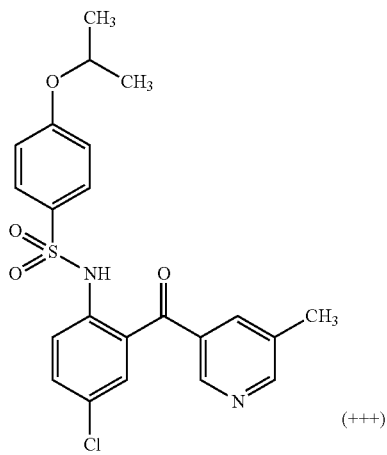
(+++)
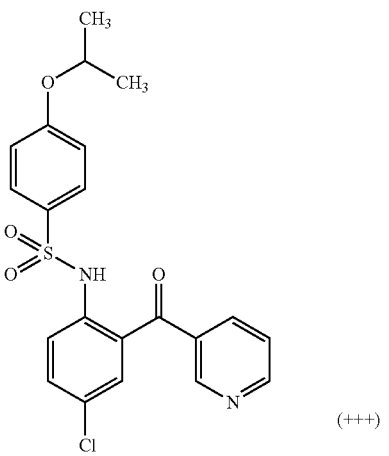
(+++)
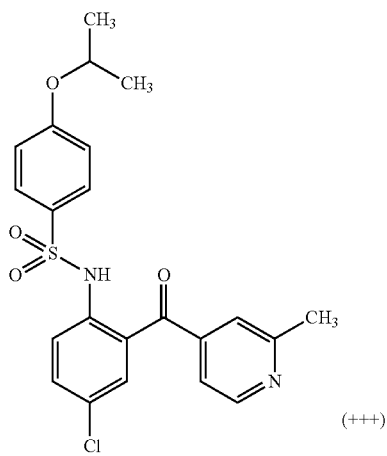
(+++)
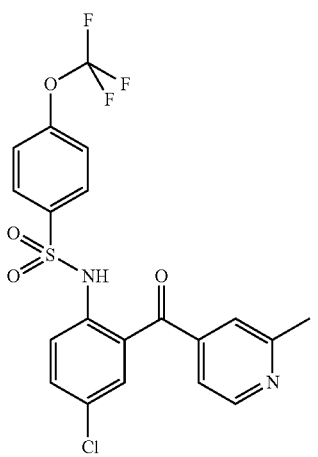
(+++)
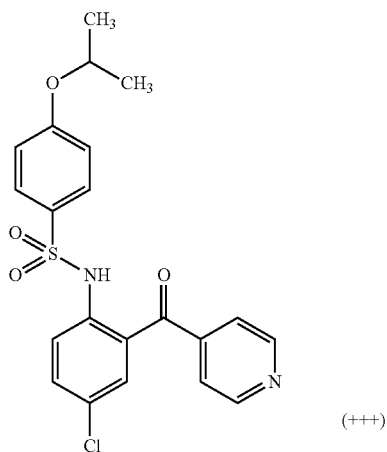
(+++)
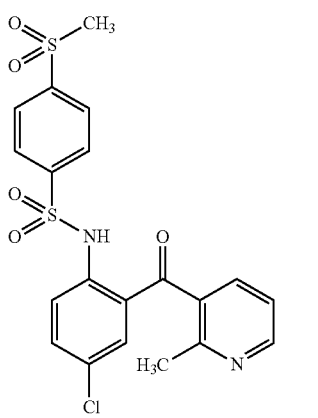
(+++)

TABLE 1-continued
Compounds with activity in either or both of the chemotaxis assay and calcium mobilization assays, with IC$_{50}$ < 100 nM (+++)
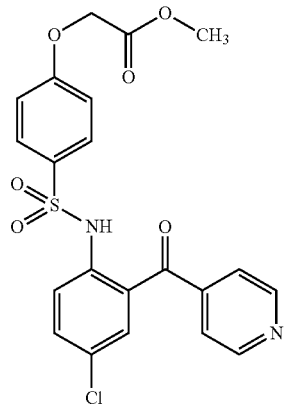
(+++)
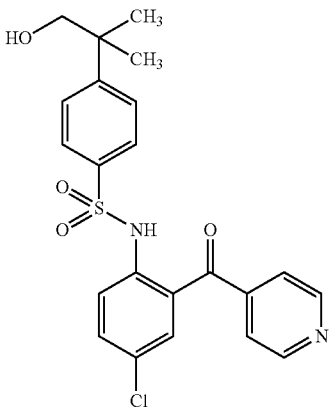
(+++)
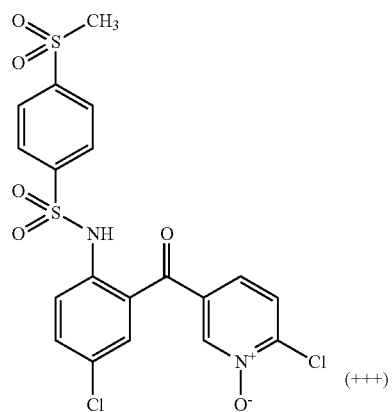
(+++)
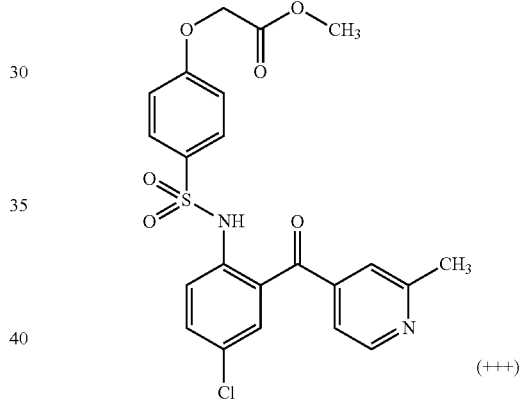
(+++)
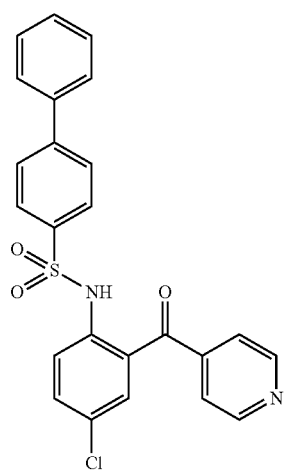
(+++)
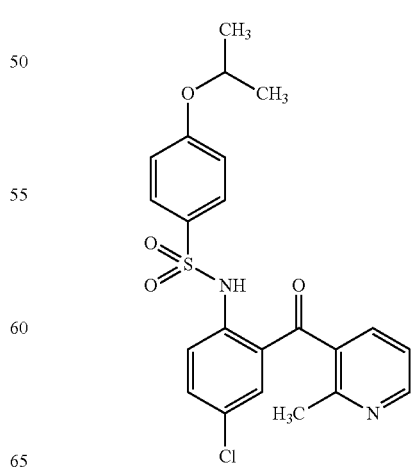
(+++)

TABLE 1-continued
Compounds with activity in either or both of the chemotaxis assay and calcium mobilization assays, with IC$_{50}$ < 100 nM (+++)
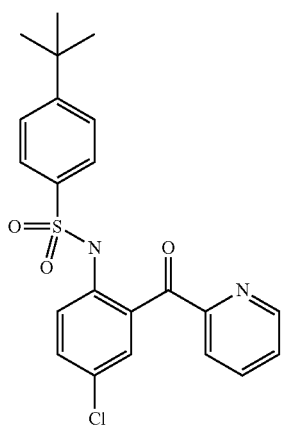
(+++)
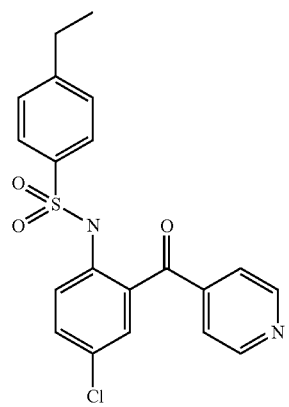
(+++)
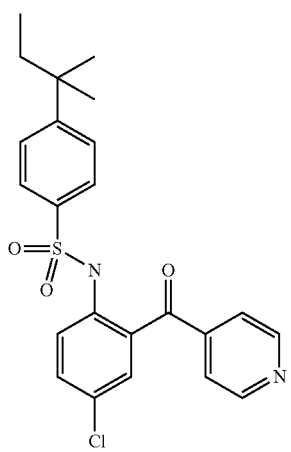
(+++)
TABLE 1-continued
Compounds with activity in either or both of the chemotaxis assay and calcium mobilization assays, with IC$_{50}$ < 100 nM (+++)
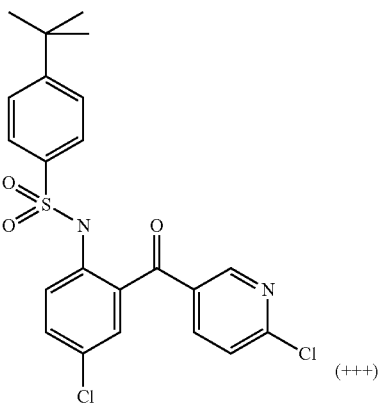
(+++)
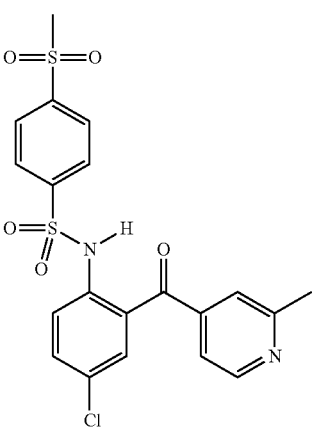
(+++)
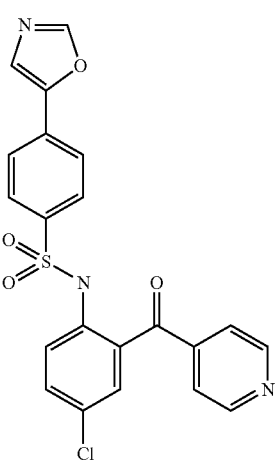
(+++)

TABLE 1-continued
Compounds with activity in either or both of the chemotaxis assay and calcium mobilization assays, with $IC_{50} < 100$ nM (+++)
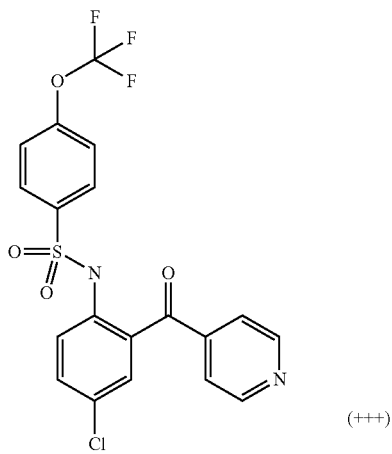
(+++)
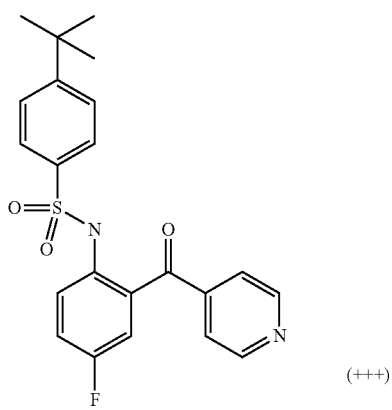
(+++)
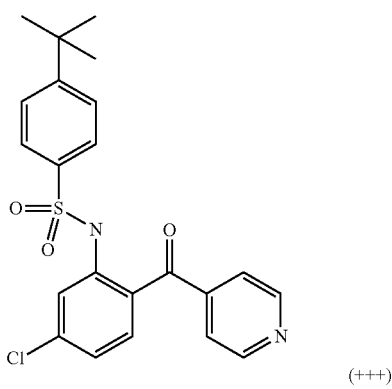
(+++)
TABLE 1-continued
Compounds with activity in either or both of the chemotaxis assay and calcium mobilization assays, with $IC_{50} < 100$ nM (+++)
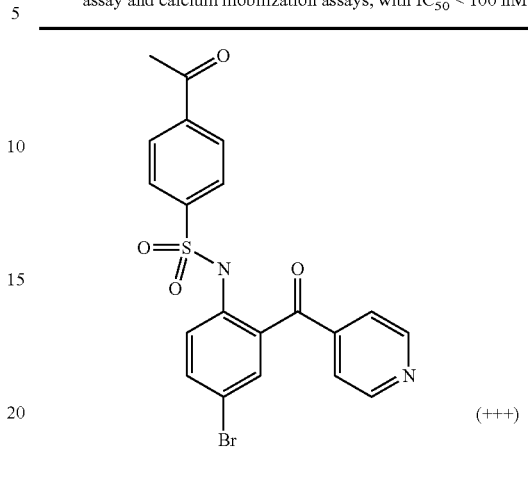
(+++)
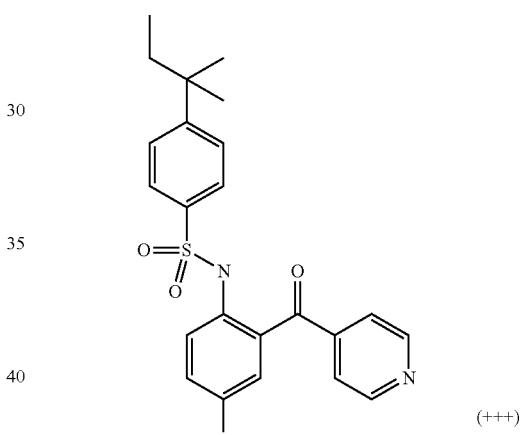
(+++)
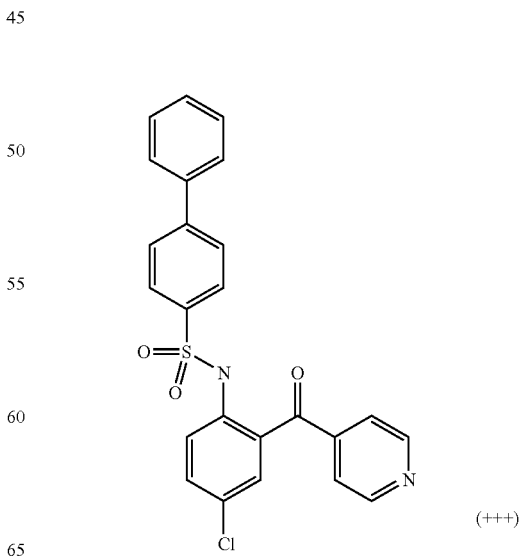
(+++)

TABLE 1-continued
Compounds with activity in either or both of the chemotaxis assay and calcium mobilization assays, with IC$_{50}$ < 100 nM (+++)
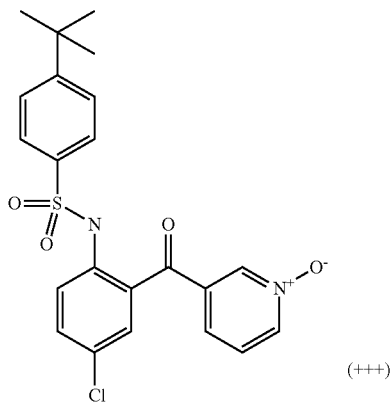
(+++)
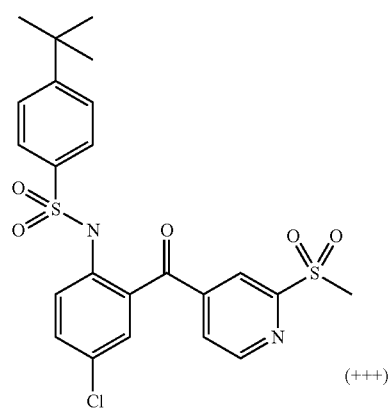
(+++)
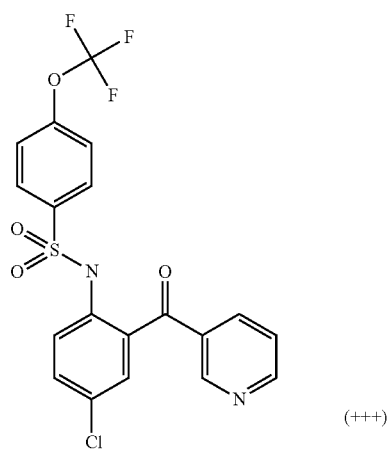
(+++)
TABLE 1-continued
Compounds with activity in either or both of the chemotaxis assay and calcium mobilization assays, with IC$_{50}$ < 100 nM (+++)
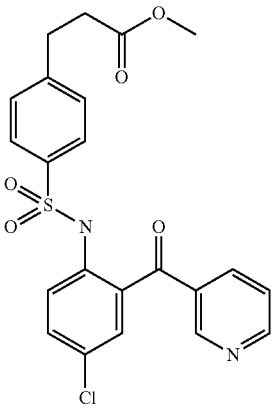
(+++)
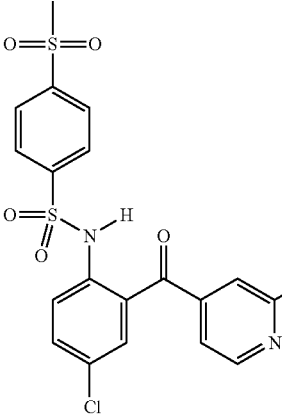
(+++)
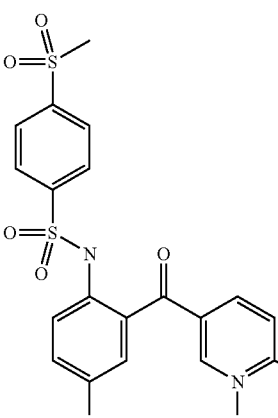
(+++)

TABLE 2
Compounds with activity in either or both of the chemotaxis assay and calcium mobilization assays, with 100 nM < IC$_{50}$ < 1000 nM (++)
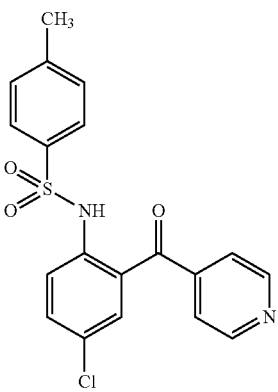
(++)
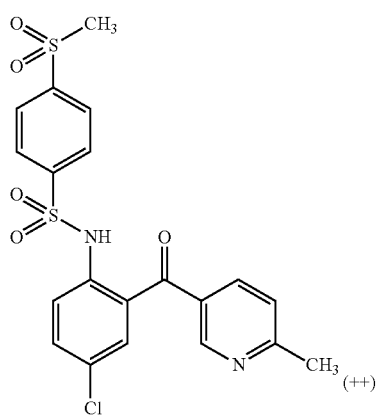
(++)
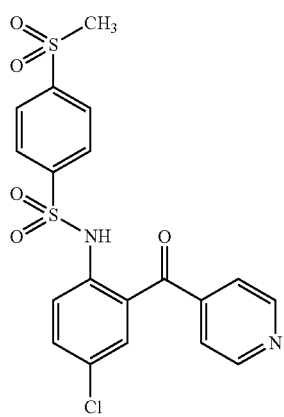
(++)
TABLE 2-continued
Compounds with activity in either or both of the chemotaxis assay and calcium mobilization assays, with 100 nM < IC$_{50}$ < 1000 nM (++)
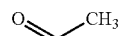
(++)
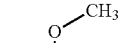
(++)
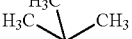
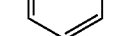
(++)

TABLE 2-continued
Compounds with activity in either or both of the chemotaxis assay and calcium mobilization assays, with 100 nM < $IC_{50}$ < 1000 nM (++)
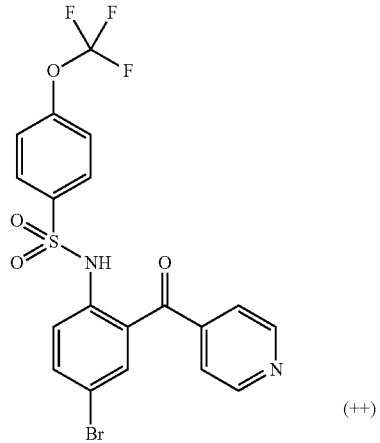
(++)
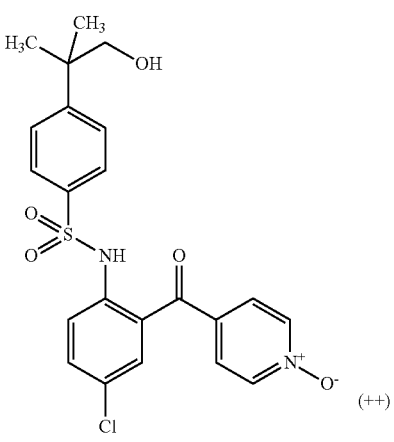
(++)
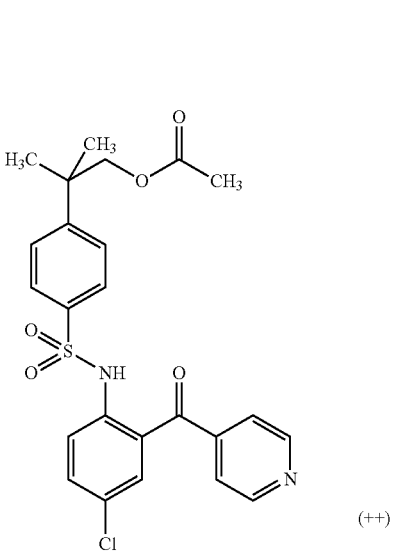
(++)
TABLE 2-continued
Compounds with activity in either or both of the chemotaxis assay and calcium mobilization assays, with 100 nM < $IC_{50}$ < 1000 nM (++)
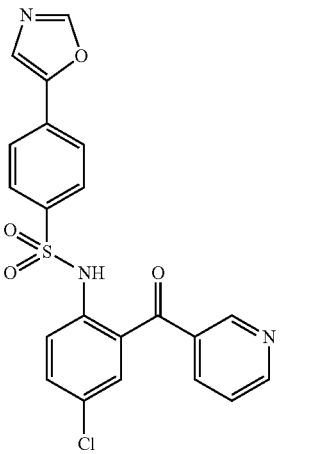
(++)
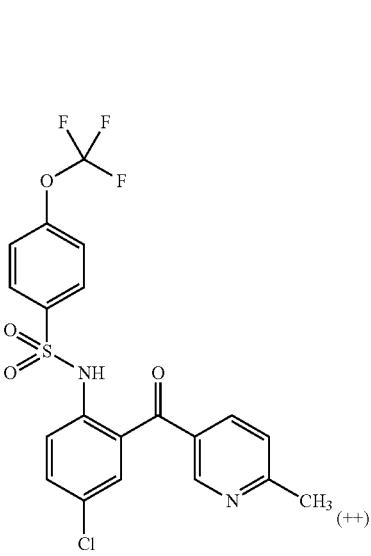
(++)
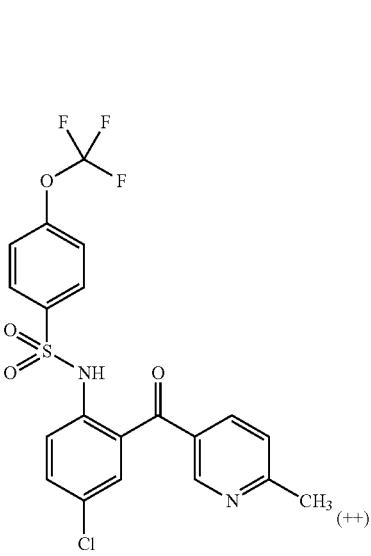
(++)

TABLE 2-continued
Compounds with activity in either or both of the chemotaxis assay and calcium mobilization assays, with 100 nM < IC$_{50}$ < 1000 nM
(++)
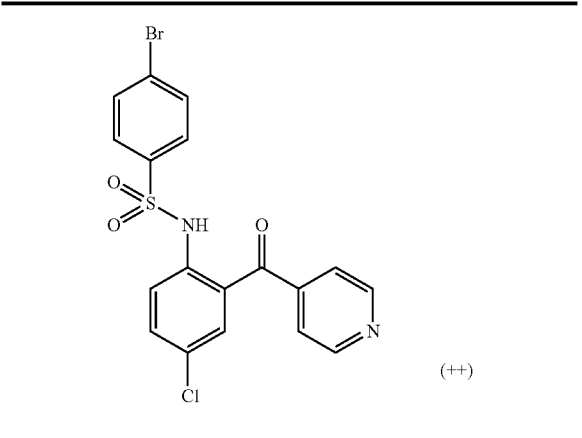
(++)
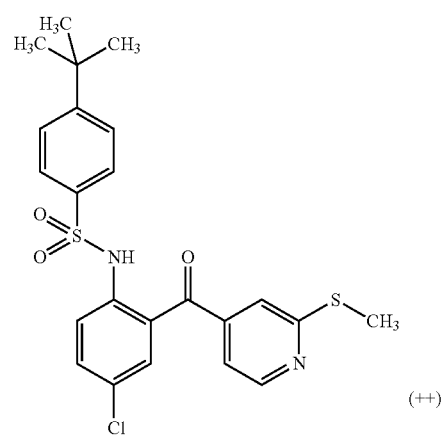
(++)
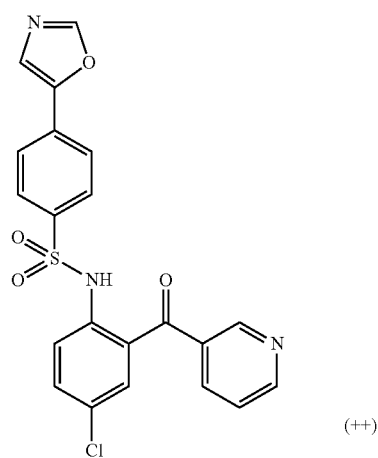
(++)
TABLE 2-continued
Compounds with activity in either or both of the chemotaxis assay and calcium mobilization assays, with 100 nM < IC$_{50}$ < 1000 nM
(++)
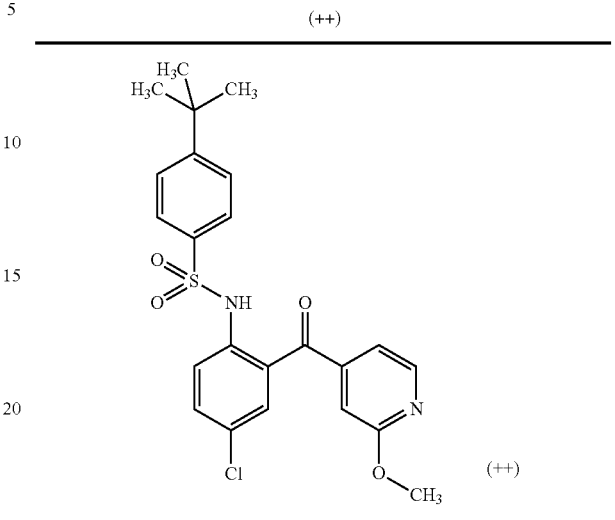
(++)
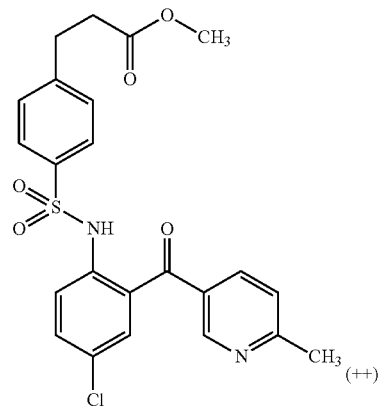
(++)
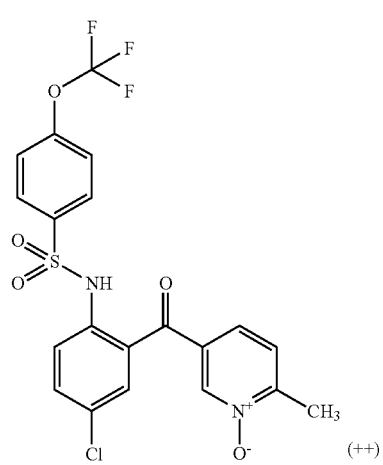
(++)

TABLE 2-continued
Compounds with activity in either or both of the chemotaxis assay and calcium mobilization assays, with 100 nM < IC$_{50}$ < 1000 nM (++)
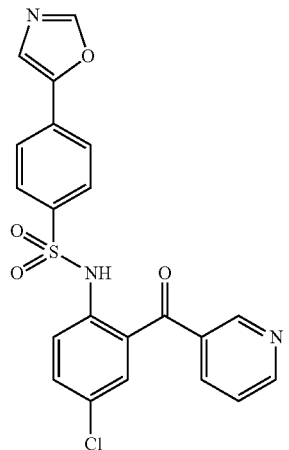
(++)
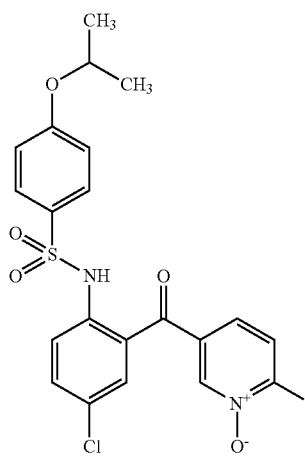
(++)
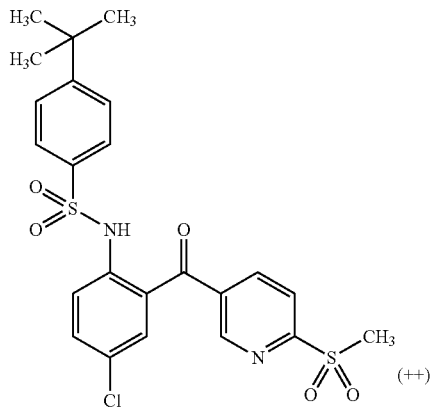
(++)
TABLE 2-continued
Compounds with activity in either or both of the chemotaxis assay and calcium mobilization assays, with 100 nM < IC$_{50}$ < 1000 nM (++)
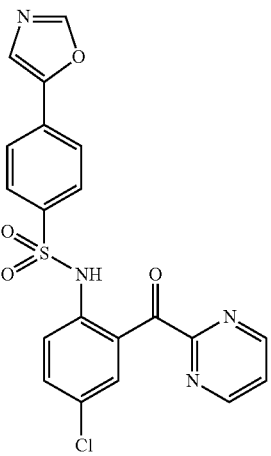
(++)
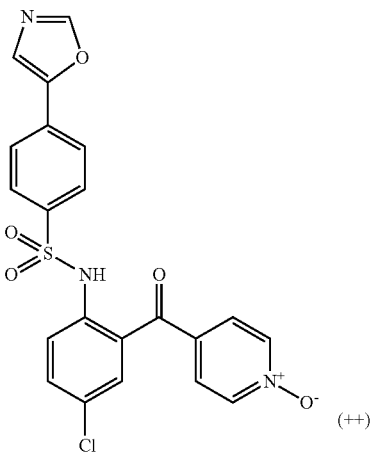
(++)
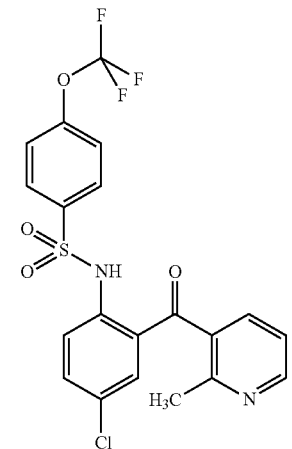
(++)

TABLE 2-continued
Compounds with activity in either or both of the chemotaxis assay and calcium mobilization assays, with 100 nM < $IC_{50}$ < 1000 nM
(++)
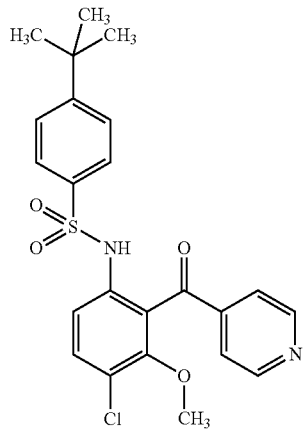
(++)
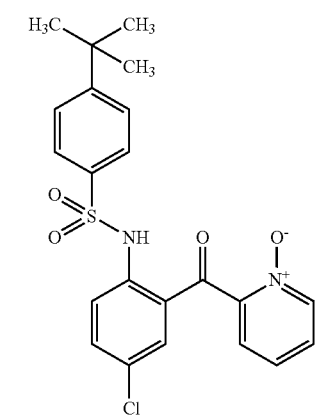
(++)
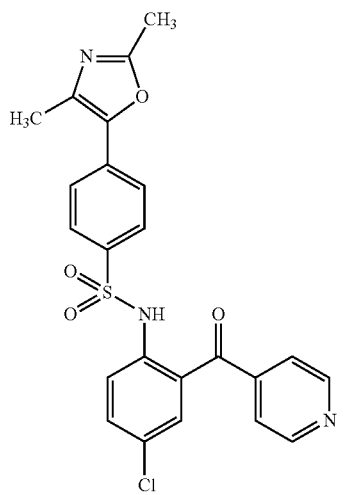
(++)
TABLE 2-continued
Compounds with activity in either or both of the chemotaxis assay and calcium mobilization assays, with 100 nM < $IC_{50}$ < 1000 nM
(++)
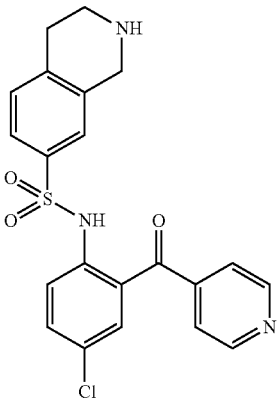
(++)
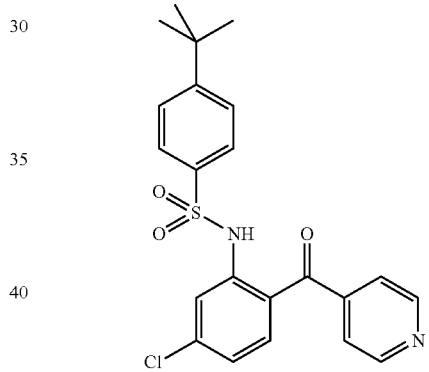
(++)
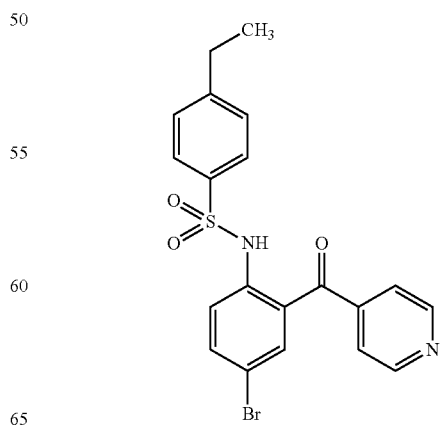
(++)

TABLE 2-continued
Compounds with activity in either or both of the chemotaxis assay and calcium mobilization assays, with 100 nM < IC$_{50}$ < 1000 nM (++)
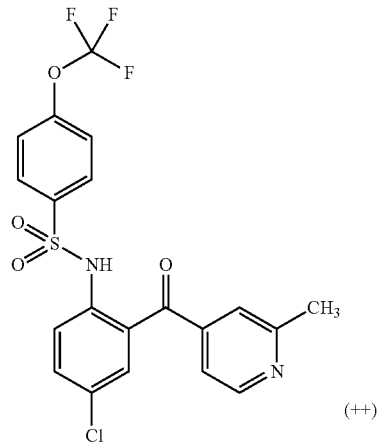
(++)
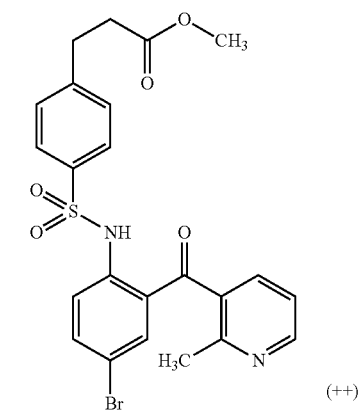
(++)
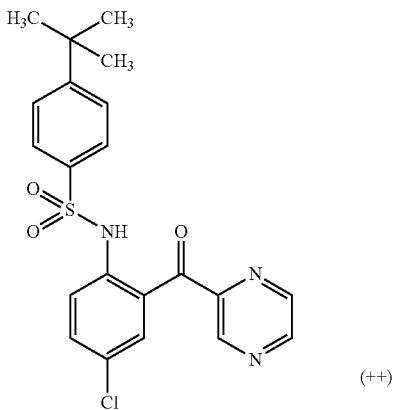
(++)
TABLE 2-continued
Compounds with activity in either or both of the chemotaxis assay and calcium mobilization assays, with 100 nM < IC$_{50}$ < 1000 nM (++)
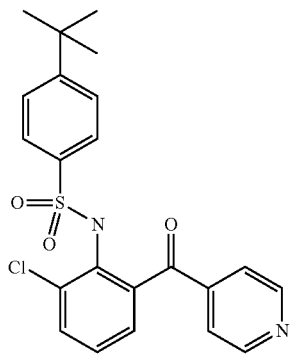
(++)
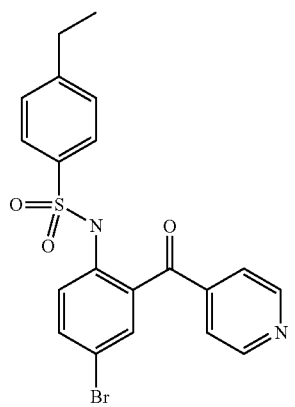
(++)
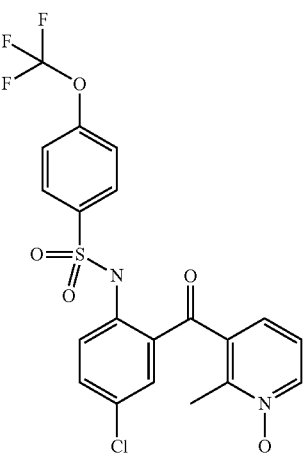
(++)

TABLE 2-continued

Compounds with activity in either or both of the chemotaxis assay and calcium mobilization assays, with 100 nM < IC$_{50}$ < 1000 nM (++)

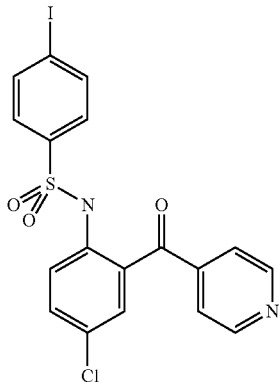

(++)

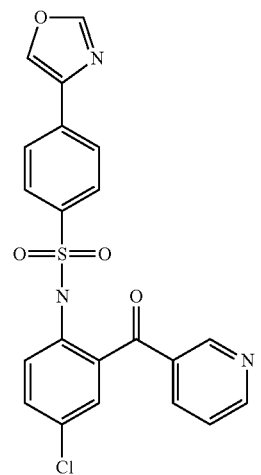

(++)

TABLE 3

Compounds with activity in either or both of the chemotaxis assay and calcium mobilization assays, with 1000 nM < IC$_{50}$ < 10000 nM (+):

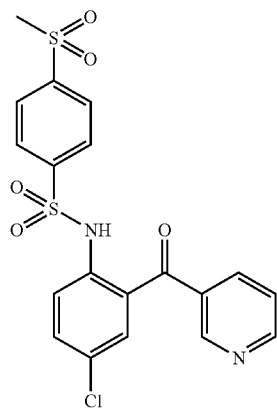

(+)

TABLE 3-continued

Compounds with activity in either or both of the chemotaxis assay and calcium mobilization assays, with 1000 nM < IC$_{50}$ < 10000 nM (+):

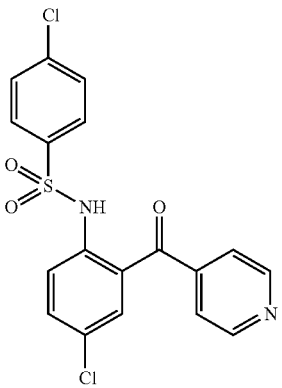

(+)

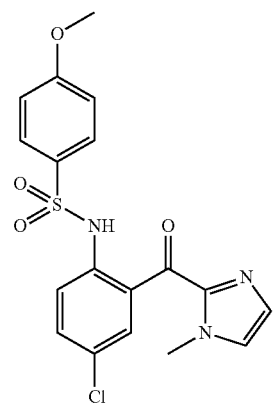

(+)

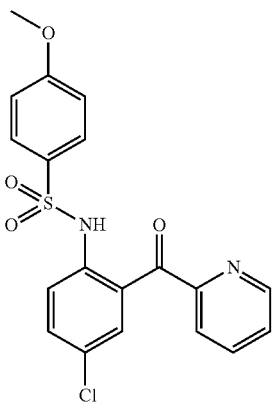

(+)

TABLE 3-continued
Compounds with activity in either or both of the chemotaxis assay and calcium mobilization assays, with 1000 nM < IC$_{50}$ < 10000 nM (+):
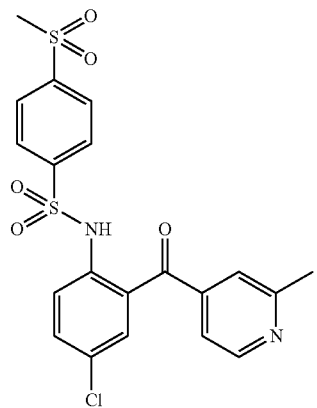
(+)
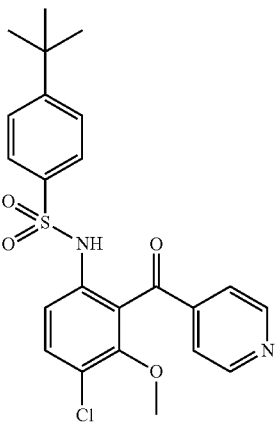
(+)
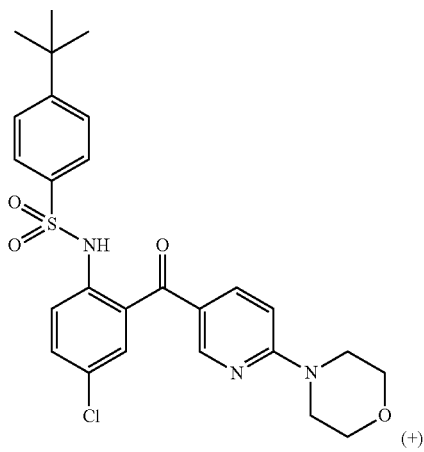
(+)
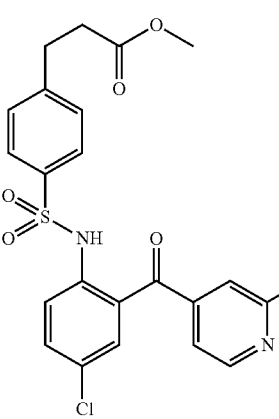
(+)
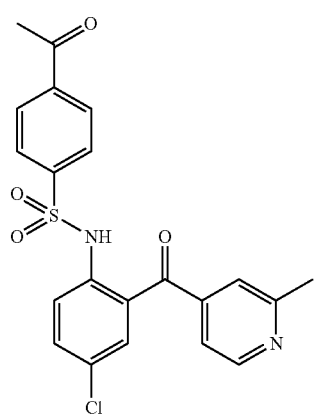
(+)
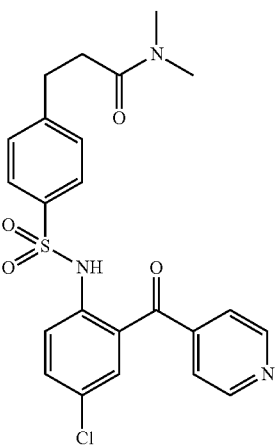
(+)

TABLE 3-continued
Compounds with activity in either or both of the chemotaxis assay and calcium mobilization assays, with 1000 nM < IC$_{50}$ < 10000 nM (+):
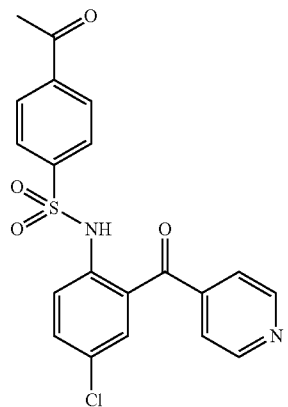
(+)
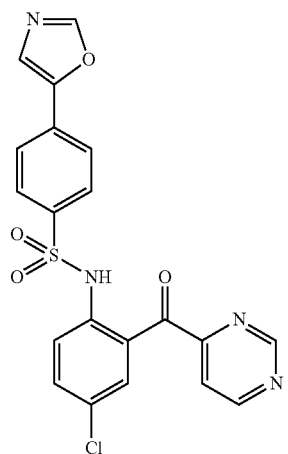
(+)
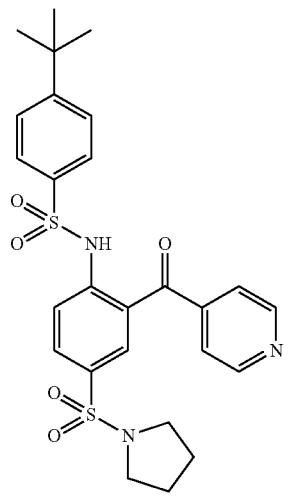
(+)
TABLE 3-continued
Compounds with activity in either or both of the chemotaxis assay and calcium mobilization assays, with 1000 nM < IC$_{50}$ < 10000 nM (+):
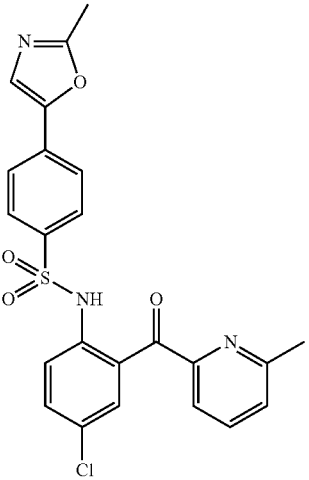
(+)
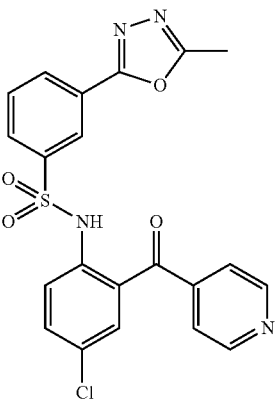
(+)
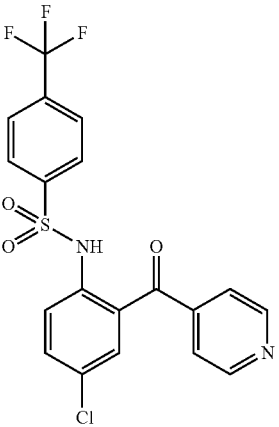
(+)

TABLE 3-continued
Compounds with activity in either or both of the chemotaxis assay and calcium mobilization assays, with 1000 nM < IC$_{50}$ < 10000 nM (+):
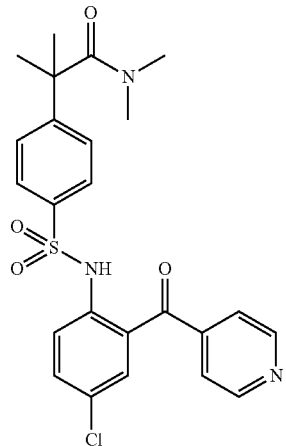
(+)
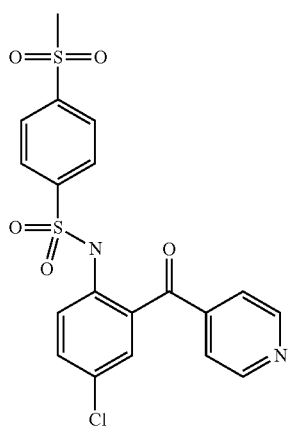
(+)
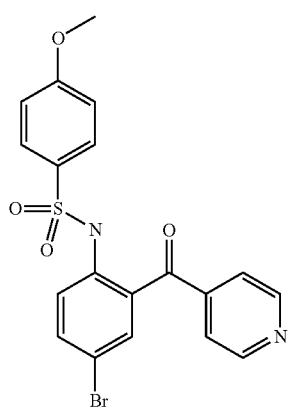
(+)
TABLE 3-continued
Compounds with activity in either or both of the chemotaxis assay and calcium mobilization assays, with 1000 nM < IC$_{50}$ < 10000 nM (+):
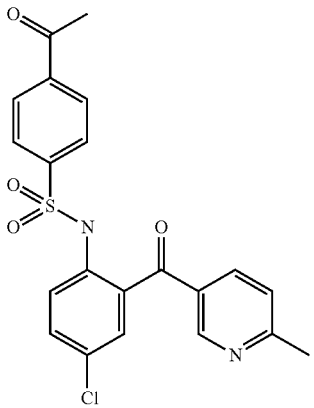
(+)
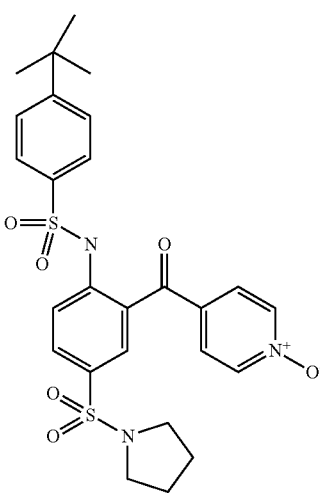
(+)
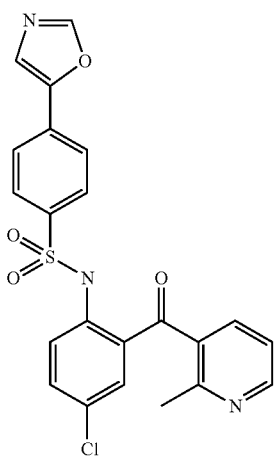
(+)

TABLE 3-continued

Compounds with activity in either or both of the chemotaxis assay and calcium mobilization assays, with 1000 nM < IC$_{50}$ < 10000 nM (+):

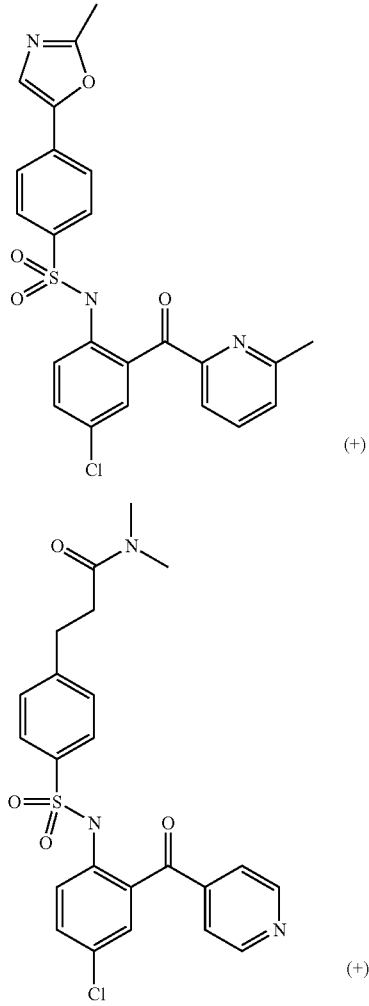

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of the formula (I), or a salt thereof:

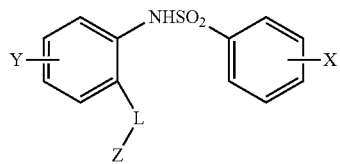

where

X represents from 1 to 4 substituents independently selected from the group consisting of halogen, —CN, —NO$_2$, —OH, —OR$^1$, —C(O)R$^1$, —CO$_2$R$^1$, —O(CO)R$^1$, —C(O)NR$^1$R$^2$, —OC(O)NR$^1$R$^2$, —SR$^1$, —SOR$^1$, —SO$_2$R$^1$, —SO$_2$NR$^1$R$^2$, —NR$^1$R$^2$, —NR$^1$C(O)R$^2$, —NR$^1$C(O)$_2$R$^2$, —NR$^1$SO$_2$R$^2$, —NR$^1$(CO)NR$^2$R$^3$, unsubstituted or substituted C$_{1-8}$ alkyl, unsubstituted or substituted C$_{2-8}$ alkenyl, unsubstituted or substituted C$_{2-8}$ alkynyl, unsubstituted or substituted C$_{3-8}$ cycloalkyl, unsubstituted or substituted C$_{6-10}$ aryl, unsubstituted or substituted 5- to 10-membered heteroaryl, and unsubstituted or substituted 3- to 10-membered heterocyclyl;

R$^1$, R$^2$ and R$^3$ are each independently selected from the group consisting of hydrogen, unsubstituted or substituted C$_{1-6}$ haloalkyl, unsubstituted or substituted C$_{1-6}$ alkyl, unsubstituted or substituted C$_{3-6}$ cycloalkyl, unsubstituted or substituted C$_{2-6}$ alkenyl, unsubstituted or substituted C$_{2-6}$ alkynyl, unsubstituted or substituted C$_{6-10}$ aryl, unsubstituted or substituted 5- to 10-membered heteroaryl, unsubstituted or substituted aryl-C$_{1-4}$ alkyl, unsubstituted or substituted aryl-C$_{1-4}$ alkyl, and unsubstituted or substituted aryloxy-C$_{1-4}$ alkyl; or two of R$^1$, R$^2$ and R$^3$ together with the atom(s) to which they are attached, may form an unsubstituted or substituted 5-, 6- or 7-membered ring;

Y represents from 1 to 3 substituents, each independently selected from the group consisting of halogen, —CN, —NO$_2$, —OH, —OR$^4$, —C(O)R$^4$, —CO$_2$R$^4$, —SR$^4$, —SOR$^4$, —SO$_2$R$^4$, and unsubstituted or substituted C$_{1-4}$ alkyl;

R$^4$ is selected from the group consisting of hydrogen, unsubstituted or substituted C$_{1-6}$haloalkyl, unsubstituted or substituted C$_{1-6}$ alkyl, unsubstituted or substituted C$_{3-6}$ cycloalkyl, unsubstituted or substituted C$_{2-6}$ alkenyl, and unsubstituted or substituted C$_{2-6}$ alkynyl;

L is —C(O)—, —S—, —SO— or —S(O)$_2$—; and

Z represents either unsubstituted or substituted monocyclic or bicyclic C$_{5-10}$ heteroaryl or unsubstituted or substituted monocyclic or bicyclic C$_{3-10}$ heterocyclyl, with the proviso that when X is methyl, then Z is not 2-thiophene, 2-(3-hydroxy-1H-indole) or 3-(1-methylpyridinium).

2. The compound of claim 1, where L is —CO—.

3. The compound of claim 2, where X represents from 1 to 3 substituents independently selected from the group consisting of halogen, —CN, —NO$_2$, —OH, —C(O)R$^1$, —CO$_2$R$^1$, —O(CO)R$^1$, —OC(O)NR$^1$R$^2$, —SR$^1$, —SOR$^1$, —SO$_2$R$^1$, —NR$^1$R$^2$, —NR$^1$C(O)R$^2$, —NR$^1$C(O)$_2$R$^2$, —NR$^1$(CO)NR$^1$R$^2$, unsubstituted or substituted C$_{1-8}$ alkyl, unsubstituted or substituted C$_{2-8}$ alkenyl, unsubstituted or substituted C$_{2-8}$ alkynyl, unsubstituted or substituted C$_{3-8}$ cycloalkyl, unsubstituted or substituted C$_{6-10}$ aryl, unsubstituted or substituted 5- or 6-membered heteroaryl, or unsubstituted or substituted 4- to 7-membered heterocyclyl.

4. The compound of claim 3, where X represents 1 to 3 substituents independently selected from the group consisting of —NO$_2$, —C(O)R$^1$, —SO$_2$R$^1$, —NR$^1$R$^2$, unsubstituted or substituted C$_{1-8}$ alkyl, unsubstituted or substituted phenyl, unsubstituted or substituted 5- or 6-membered heteroaryl, or unsubstituted or substituted 5- or 6-membered heterocyclyl.

5. The compound of claim 2, where at least one X substituent is situated para to the sulfonamido bond as defined in formula (I).

6. The compound of claim 2, where X is unsubstituted C$_{1-8}$ alkyl, unsubstituted C$_{3-8}$ cycloalkyl, unsubstituted C$_{2-8}$ alkenyl, or unsubstituted C$_{2-8}$ alkynyl.

7. The compound of claim 2, where X is substituted $C_{1-8}$ alkyl, substituted $C_{3-8}$ cycloalkyl, substituted $C_{2-8}$ alkenyl, or substituted $C_{2-8}$ alkynyl, each having from 1 to 5 substituents independently selected from the group consisting of halogen, —OH, —CN, —NO$_2$, =O, —OC(O)R$^1$, —OR$^1$, —C(O)R$^1$, —CONR$^1$R$^2$, —OC(O)NR$^1$R$^2$, —NR$^2$C(O)R$^1$, —NR$^1$C(O)NR$^2$R$^3$, —CO$_2$R$^1$, —NR$^1$R$^2$, —NR$^2$CO$_2$R$^1$, —SR$^1$, —SOR$^1$, —SO$_2$R$^1$, —SO$_2$NR$^1$R$^2$, —NR$^1$SO$_2$R$^2$, unsubstituted or substituted aryl, unsubstituted or substituted heteroaryl, and unsubstituted or substituted heterocyclyl.

8. The compound of claim 7, where X is substituted $C_{1-8}$ alkyl or substituted $C_{3-8}$ cycloalkyl, each having from 1 to 3 substituents independently selected from the group consisting of halogen, —OH, —CN, =O, —OC(O)R$^1$, —OR$^1$, —C(O)R$^1$, —CONR$^1$R$^2$, —NR$^2$C(O)R$^1$, —CO$_2$R$^1$, —NR$^1$R$^2$, —SR$^1$, —SOR$^1$, —SO$_2$R$^1$, —NR$^1$SO$_2$R$^2$, unsubstituted or substituted aryl, and unsubstituted or substituted heteroaryl.

9. The compound of claim 8, where X is substituted $C_{1-8}$ alkyl, having from 1 to 3 substituents independently selected from the group consisting of halogen, —OH, —CN, =O, —OC(O)R$^1$, —OR$^1$, —C(O)R$^1$, —CONR$^1$R$^2$, —NR$^2$C(O)R$^1$, —CO$_2$R$^1$, —NR$^1$R$^2$, —SO$_2$R$^1$, unsubstituted or substituted aryl, and unsubstituted or substituted heteroaryl.

10. The compound of claim 2, where X is unsubstituted or substituted $C_{6-10}$ aryl, unsubstituted or substituted 5- to 10-membered heteroaryl, or unsubstituted or substituted 3- to 10-membered heterocyclyl, where when X is substituted is has from 1 to 4 substituents independently selected from the group consisting of halogen, unsubstituted or substituted $C_{1-8}$ alkyl, unsubstituted or substituted $C_{1-8}$ haloalkyl, —CN, —NO$_2$, —OH, —OR$^1$, =O, —OC(O)R$^1$, —CO$_2$R$^1$, —C(O)R$^1$, —CONR$^1$R$^2$, —OC(O)NR$^1$R$^2$, —NR$^2$C(O)R$^1$, —NR$^1$C(O)NR$^2$R$^3$, —NR$^1$R$^2$, —NR$^2$CO$_2$R$^1$, —SR$^1$, —SOR$^1$, —SO$_2$R$^1$, —SO$_2$NR$^1$R$^2$, and —NR$^1$SO$_2$R$^2$.

11. The compound of claim 10, where X is substituted $C_{6-10}$aryl or unsubstituted or substituted 5- to 10-membered heteroaryl, where when X is substituted it has from 1 to 3 substituents independently selected from the group consisting of halogen, —CN, —OH, —OR$^1$, =O, —OC(O)R$^1$, —CO$_2$R$^1$, —C(O)R$^1$, —CONR$^1$R$^2$, —NR$^2$C(O)R$^1$, —NR$^1$R$^2$, —SR$^1$, —SOR$^1$, —SO$_2$R$^1$, —NR$^1$SO$_2$R$^2$, unsubstituted or substituted $C_{1-8}$ alkyl, and $C_{1-8}$ unsubstituted or substituted haloalkyl.

12. The compound of claim 11, where X is unsubstituted or substituted phenyl or unsubstituted or substituted 5- or 6-membered heteroaryl, where when X is substituted it has from 1 to 3 substituents independently selected from the group consisting of halogen, —OH, —OR$^1$, —C(O)R$^1$, —CONR$^1$R$^2$, —NR$^2$C(O)R$^1$, —NR$^1$R$^2$, —SO$_2$R$^1$, unsubstituted or substituted $C_{1-8}$ alkyl, and unsubstituted or substituted $C_{1-8}$ haloalkyl.

13. The compound of claim 10, where X is unsubstituted or substituted 4- to 7-membered heterocyclyl, where when X is substituted it has from 1 to 3 substituents independently selected from the group consisting of $C_{1-8}$ alkyl, $C_{1-8}$ haloalkyl, —OH, —OC(O)R$^1$, —CO$_2$R$^1$, —C(O)R$^1$, —CONR$^1$R$^2$, —NR$^1$R$^2$, —SO$_2$R$^1$, and —NR$^1$SO$_2$R$^2$.

14. The compound of claim 13, where X is a unsubstituted or substituted 5- or 6-membered heterocyclyl, where when X is substituted it has 1 to 2 substituents independently selected from the group of unsubstituted or substituted $C_{1-8}$ alkyl, unsubstituted or substituted $C_{1-8}$ haloalkyl, —OH, —C(O)R$^1$, —CONR$^1$R$^2$, —NR$^1$R$^2$, and —SO$_2$R$^1$.

15. The compound of claim 2, where R$^1$, R$^2$ and R$^3$ are unsubstituted.

16. The compound of claim 2, where R$^1$, R$^2$ and R$^3$, when substituted, can have from 1 to 3 substituents independently selected from the group consisting of halogen, —OH, —OR', —OCOHNR', —OCONR'$_2$, —SH, —SR', —SO$_2$NH$_2$, —CONH$_2$, —NHC(O)NH$_2$, NR'C(O)NH$_2$, —CO$_2$H, —CN, —NO$_2$, —NH$_2$, —NHR' and —NR'$_2$, —S(O)R', —S(O)$_2$R', —CO$_2$R', —CONR'$_2$, —CONHR', —C(O)R', —NR'COR', —NHCOR', —NR'CO$_2$R', —NHCO$_2$R', —CO$_2$R', —NR'C(O)NR'$_2$, —NHC(O)NR'$_2$, —NR'C(O)NHR', —NHC(O)NHR', —NR'SO$_2$R', —NHSO$_2$R', —SO$_2$NR'$_2$, and —SO$_2$NHR', where R' is $C_{1-6}$alkyl.

17. The compound of claim 2, where Y represents from 1 to 2 substituents, each independently selected from the group consisting of halogen, —CN, —NO$_2$, —OH, —OR$^4$, —C(O)R$^4$, —CO$_2$R$^4$, —SOR$^4$, —SO$_2$R$^4$, and unsubstituted or substituted $C_{1-4}$ alkyl.

18. The compound of claim 2, where Y represents from 1 to 3 substituents independently selected from the group consisting of halogen, —CN, —NO$_2$, —C(O)R$^4$, —SR$^4$, —CF$_3$, —SOR$^4$, and —SO$_2$R$^4$.

19. The compound of claim 18, where Y represents from 1 to 3 substituents independently selected from the group consisting of halogen, —CN, —NO$_2$, —CF$_3$, and —SO$_2$R$^4$.

20. The compound of claim 18, where Y represents 1 or 2 substituents where at least halogen is present and optionally another substituent selected from the group consisting of halogen, —CN, —NO$_2$, —OH, —OR$^4$, —C(O)R$^4$, —CO$_2$R$^4$, —SR$^4$, —SOR$^4$, —SO$_2$R$^4$ and unsubstituted or substituted $C_{1-4}$ alkyl.

21. The compound of claim 2, where at least one Y substituent is located para to the sulfonamide bond as defined in formula (I), and one Y substituent is halogen.

22. The compound of claim 18, where Y is unsubstituted $C_{1-4}$ alkyl.

23. The compound of claim 18, where Y is substituted $C_{1-4}$ alkyl, having from 1 to 3 substituents independently selected from the group consisting of halogen, —OH, —CN, —NO$_2$, =O, —OC(O)R$^4$, —CO$_2$R$^4$, —C(O)R$^4$, —CONR$^4$R$^5$, —OC(O)NR$^4$R$^5$, —NR$^4$C(O)R$^5$, —NR$^4$C(O)NR$^5$R$^6$, —NR$^4$R$^5$, —NR$^4$CO$_2$R$^5$, —SR$^4$, —SOR$^4$, —SO$_2$R$^4$, —SO$_2$NR$^4$R$^5$, and —NR$^4$SO$_2$R$^5$, where R$^4$, R$^5$ and R$^6$ are each independently selected from the group consisting of hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, and unsubstituted or substituted $C_{2-6}$ alkynyl; or where any two of R$^4$, R$^5$ and R$^6$ together with the atom(s) to which they are attached, may form a 5-, 6- or 7-membered ring.

24. The compound of claim 23, where Y is substituted $C_{1-4}$ alkyl, having from 1 to 3 substituents independently selected from the group consisting of halogen, —OH, —OR$^4$, —CN, —NO$_2$, =O, —OC(O)R$^4$, —CO$_2$R$^4$, —C(O)R$^4$, —CONR$^4$R$^5$, —NR$^4$C(O)R$^5$, —NR$^4$R$^5$, —NR$^4$, —SR$^4$, —SOR$^4$, —SO$_2$R$^4$, and —NR$^4$SO$_2$R$^5$.

25. The compound of claim 23, where R$^4$, R$^5$ and R$^6$ are unsubstituted.

26. The compound of claim 23, where R$^4$, R$^5$ and R$^6$, when substituted, can have from with from 1 to 3 substituents independently selected from the group consisting of —OH, —OR', —SH, —SR', —SO$_2$NH$_2$, —CONH$_2$, —NHC(O)NH$_2$, N($C_{1-6}$alkyl)C(O)NH$_2$, —CO$_2$H, —CN, —NO$_2$, —NH$_2$, —NHR', —NR'$_2$, —S(O)R', —S(O)$_2$R', —CO$_2$R', —CONHR', —CONR'$_2$, and —C(O)R', where R' is $C_{1-6}$alkyl.

27. The compound of claim 2, where Z represents unsubstituted, monocyclic or bicyclic $C_{5-10}$ heteroaryl or unsubstituted, monocyclic or bicyclic $C_{3-10}$ heterocyclyl.

28. The compound of claim 2, where Z is substituted, monocyclic or bicyclic $C_{5-10}$ heteroaryl or substituted, monocyclic or bicyclic $C_{3-10}$ heterocyclyl, having from 1 to 5 substituents independently selected from the group consisting of halogen, unsubstituted or substituted $C_{1-8}$ alkyl, unsubstituted or substituted $C_{1-8}$ cycloalkyl, unsubstituted or substituted $C_{2-8}$ alkenyl, unsubstituted or substituted $C_{2-8}$ alkynyl, unsubstituted or substituted $C_{1-8}$ alkoxy, =O, —CN, —NO$_2$, —OH, —OR$^7$, —OC(O)R$^7$, —CO$_2$R$^7$, —C(O)R$^7$, —CONR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —SOR$^7$, —SO$_2$R$^7$, —SO$_2$NR$^7$R$^8$, —NR$^7$SO$_2$R$^8$, unsubstituted or substituted $C_{6-10}$ aryl, unsubstituted or substituted heteroaryl and unsubstituted or substituted heterocyclyl;

where R$^7$, R$^8$ and R$^9$ are each independently hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted phenyl, unsubstituted or substituted heteroaryl, unsubstituted or substituted aryl-$C_{1-4}$ alkyl, and unsubstituted or substituted aryloxy-$C_{1-4}$ alkyl; or where any two of R$^7$, R$^8$ and R$^9$ together with the atom(s) to which they are attached, may form a 5-, 6- or 7-membered ring.

29. The compound of claim 2, where Z represents an unsubstituted 5- or 6-membered heteroaryl.

30. The compound of claim 2, where Z is substituted 5- or 6-membered heteroaryl, having from 1 to 3 substituents independently selected from the group consisting of halogen, unsubstituted or substituted $C_{1-8}$ alkyl, unsubstituted or substituted $C_{3-8}$ cycloalkyl, unsubstituted or substituted $C_{2-8}$ alkenyl, unsubstituted or substituted $C_{2-8}$ alkynyl, unsubstituted or substituted $C_{1-8}$ alkoxy, =O, —CN, —NO$_2$, —OH, —OR$^7$, —OC(O)R$^7$, —CO$_2$R$^7$, —C(O)R$^7$, —CONR$^7$R$^8$, —NR$^7$C(O)R$^8$, —NR$^7$R$^8$, —SR$^7$, —SOR$^7$, —SO$_2$R$^7$, —SO$_2$NR$^7$R$^8$, —NR$^7$SO$_2$R$^8$, unsubstituted or substituted phenyl, unsubstituted or substituted 5- or 6-membered heteroaryl, and unsubstituted or substituted 3- to 7-membered heterocyclyl.

31. The compound of claim 2, where Z represents unsubstituted or substituted 6-membered heteroaryl with carbon and up to 3 nitrogen atoms and with from 1 to 3 substituents independently selected from the group consisting of halogen, unsubstituted or substituted $C_{1-8}$ alkyl, unsubstituted or substituted $C_{3-8}$ cycloalkyl, unsubstituted or substituted $C_{2-8}$ alkenyl, unsubstituted or substituted $C_{2-8}$ alkynyl, unsubstituted or substituted $C_{1-8}$ alkoxy, =O, —CN, —NO$_2$, —OH, —OC(O)R$^7$, —CO$_2$R$^7$, —C(O)R$^7$, —CONR$^7$R$^8$, —NR$^7$C(O)R$^8$, —NR$^7$R$^8$, —SR', —SOR$^7$, —SO$_2$R$^7$, —SO$_2$NR$^7$R$^8$, —NR$^7$SO$_2$R$^8$, unsubstituted or substituted phenyl, and unsubstituted or substituted 5- and 6-membered heteroaryl.

32. The compound of claim 2, where Z is unsubstituted or substituted 6-membered heteroaryl with carbon and 1 to 2 nitrogen atoms and with 1 or 2 substituents independently selected from the group consisting of halogen, unsubstituted or substituted $C_{1-6}$ alkyl, unsubstituted or substituted $C_{1-6}$ alkoxy, =O, —CN, —NO$_2$, —OH, —C(O)R$^7$, —CONR$^7$R$^8$, —NR$^7$C(O)R$^8$, —NR$^7$R$^8$, —SR$^7$, —SOR$^7$, —SO$_2$R$^7$, —SO$_2$NR$^7$R$^8$, —NR$^7$SO$_2$R$^8$, unsubstituted or substituted 3 to 7-membered heterocycyl, and unsubstituted or substituted 5- or 6-membered heteroaryl.

33. The compound of claim 2, where Z is selected from the group consisting of unsubstituted or substituted pyridyl, unsubstituted or substituted pyrimidinyl, unsubstituted or substituted pyridazinyl, and unsubstituted or substituted pyrazinyl.

34. The compound of claim 33, where Z is selected from the group consisting of substituted pyridyl, substituted pyrimidinyl, substituted pyridazinyl, and substituted pyrazinyl, and where at least one ring nitrogen is substituted with =O.

35. The compound of claim 2, where Z is pyridinyl with from 0 to 3 substituents; pyrimidinyl with from 0 to 3 substituents; pyrazinyl with from 0 to 3 substituents; or pyridazinyl with from 0 to 3 substituents.

36. The compound of claim 2, where Z is substituted with at least one substituent located ortho to one of the heteroatoms in the ring or directly connected to a ring heteroatom.

37. The compound of claim 28, where the substituent on Z is unsubstituted $C_{1-8}$ alkyl, unsubstituted $C_{3-8}$ cycloalkyl, unsubstituted $C_{2-8}$ alkenyl, unsubstituted $C_{2-8}$ alkynyl or unsubstituted $C_{1-8}$ alkoxy, unsubstituted $C_{6-10}$ aryl, unsubstituted 3- to 7-membered heterocyclyl, and 3- to 7-membered heteroaryl.

38. The compound of claim 28, where the substituent on Z is substituted $C_{1-8}$alkyl, substituted $C_{3-8}$ cycloalkyl, substituted $C_{2-8}$ alkenyl, substituted $C_{2-8}$ alkynyl or substituted $C_{1-8}$ alkoxy, each having from 1 to 5 substituents independently selected from the group consisting of halogen, —OH, —OR$^7$, —CN, —NO$_2$, =O, —CN, —NO$_2$, —OC(O)R$^7$, —CO$_2$R$^7$, —C(O)R$^7$, —CONR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —SOR$^7$, —SO$_2$R$^7$, —SO$_2$NR$^7$R$^8$, —NR$^7$SO$_2$R$^8$, unsubstituted or substituted phenyl, unsubstituted or substituted 5- or 6-membered heteroaryl, or unsubstituted or substituted 3- to 6-membered heterocyclyl.

39. The compound of claim 28, where the substituent on Z is substituted $C_{1-8}$ alkyl, substituted $C_{3-8}$ cycloalkyl, substituted $C_{2-8}$ alkenyl, substituted $C_{2-8}$ alkynyl or substituted $C_{1-8}$ alkoxy groups, each having from 1 to 3 substituents independently selected from the group consisting of halogen, —OH, —OR$^7$, =O, —CO$_2$R$^7$, —C(O)R$^7$, —CONR$^7$R$^8$, —NR$^7$C(O)R$^8$, —NR$^7$R$^8$, —SR$^7$, —SOR$^7$, —SO$_2$R$^7$, —NR$^7$SO$_2$R$^8$, unsubstituted or substituted phenyl, unsubstituted or substituted 5- or 6-membered heteroaryl, and unsubstituted or substituted 3- to 6-membered heterocyclyl.

40. The compound of claim 28, where the substituent on Z is substituted $C_{1-8}$ alkyl, substituted $C_{3-8}$ cycloalkyl, substituted $C_{2-8}$ alkenyl, substituted $C_{2-8}$ alkynyl or substituted $C_{1-8}$ alkoxy groups, each having from 1 to 3 substituents independently selected from the group consisting of halogen, —OH, —OR$^7$, =O, —C(O)R$^7$, —CO$_2$R$^7$, —CONR$^7$R$^8$, —NR$^7$C(O)R$^8$, —NR$^7$R$^8$, —SR$^7$, —SOR$^7$, —SO$_2$R$^7$, —SO$_2$NR$^7$R$^8$, —NR$^7$SO$_2$R$^8$, unsubstituted or substituted 5- or 6-membered heteroaryl, and 3- to 6-membered heterocyclyl.

41. The compound of claim 28, where the substituent on Z is substituted aryl, substituted heteroaryl or substituted heterocyclyl, each having from 1 to 5 substituents independently selected from the group consisting of halogen, —OH, —OR$^7$, —CN, —NO$_2$, =O, —CN, —NO$_2$, —OC(O)R$^7$, —OC(O)R$^7$, —CO$_2$R$^7$, —C(O)R$^7$, —CONR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —SOR$^7$, —SO$_2$R$^7$, —SO$_2$NR$^7$R$^8$, —NR$^7$SO$_2$R$^8$ and unsubstituted or substituted 5- or 6-membered heteroaryl, and 3- to 6-membered heterocyclyl.

42. The compound of claim 28, where the substituent on Z is substituted phenyl or substituted heteroaryl, each having from 1 to 3 substituents independently selected from the group consisting of halogen, —OH, —OR$^7$, —CN, —NO$_2$, =O, —CN, —NO$_2$, —OC(O)R$^7$, —CO$_2$R$^7$, —C(O)R$^7$, —CONR$^7$R$^8$, —NR$^7$C(O)R$^8$, —NR$^7$R$^8$, —SR$^7$, —SOR$^7$, —SO$_2$R$^7$, —NR$^7$SO$_2$R$^8$, unsubstituted or substituted C$_{1-8}$ alkyl, unsubstituted or substituted C$_{1-8}$ haloalkyl, unsubstituted or substituted C cycloalkyl, and 3- to 6-membered heterocyclyl.

43. The compound of claim 28, where the substituent on Z is unsubstituted or substituted heterocyclyl having from 1 to 2 substituents independently selected from the group consisting of unsubstituted or substituted C$_{1-8}$ alkyl, C$_{1-8}$ haloalkyl, —OH, —C(O)R$^7$, —CONR$^7$R$^8$, —NR$^7$R$^8$, and —SO$_2$R$^7$.

44. The compound of claim 28, where each R$^7$, R$^8$ and R$^9$ is unsubstituted.

45. The compound of claim 28, where each R$^7$, R$^8$ and R$^9$, when substituted, can have from 1 to 3 substituents independently selected from the group consisting of halogen, —OH, —OR', —OCONHR', —OCONR'$_2$, —SH, —SR', —CN, —SO$_2$NH$_2$, —CONH$_2$, —NHC(O)NH$_2$, —NR'C(O)NH$_2$, —CO$_2$H, —NO$_2$, —NH$_2$, —NHR' and —NR'$_2$, —S(O)R', —S(O)$_2$R', —CO$_2$R', —CONR'$_2$, —CONHR', —C(O)R', —NR'COR', —NHCOR', —NR'CO$_2$R', —NHCO$_2$R', —CO$_2$R', —NR'C(O)NR'$_2$, —NHC(O)NR'$_2$, —NR'C(O)NHR', —NHC(O)NHR', —NR'SO$_2$R', —NHSO$_2$R', —SO$_2$NR'$_2$, and —SO$_2$NHR', where R' is C$_{1-6}$alkyl.

46. The compound of claim 3, where Y represents from 1 to 3 substituents, each independently selected from the group consisting of halogen, —CN, —NO$_2$, —OH, —C(O)R$^4$, —CO$_2$R$^4$, —SR$^4$, —SOR$^4$, —SO$_2$R$^4$, and unsubstituted or substituted C$_{1-4}$ alkyl.

47. The compound of claim 3, where at least one Y is halogen.

48. The compound of claim 46, where X is C$_{1-8}$ alkyl.

49. The compound of claim 3, where Z represents unsubstituted or substituted, monocyclic or bicyclic C$_{5-10}$ heteroaryl or unsubstituted or substituted, monocyclic or bicyclic C$_{3-10}$ heterocyclyl.

50. The compound of claim 3, where Z is pyridinyl with from 0 to 3 substituents; pyrimidinyl with from 0 to 3 substituents; pyrazinyl with from 0 to 3 substituents; or pyridazinyl with from 0 to 3 substituents.

51. The compound of claim 49, where X is C$_{1-8}$ alkyl.

52. The compound of claim 17, where Z represents unsubstituted or substituted, monocyclic or bicyclic C$_{5-10}$ heteroaryl or unsubstituted or substituted, monocyclic or bicyclic C$_{3-10}$ heterocyclyl.

53. The compound of claim 17, where Z is pyridinyl with from 0 to 3 substituents; pyrimidinyl with from 0 to 3 substituents; pyrazinyl with from 0 to 3 substituents; or pyridazinyl with from 0 to 3 substituents.

54. The compound of claim 52, where at least one Y is halogen.

55. The compound of claim 46, where Z represents unsubstituted or substituted, monocyclic or bicyclic C$_{5-10}$ heteroaryl or unsubstituted or substituted, monocyclic or bicyclic C$_{3-10}$ heterocyclyl.

56. The compound of claim 46, where Z is pyridinyl with from 0 to 3 substituents; pyrimidinyl with from 0 to 3 substituents; pyrazinyl with from 0 to 3 substituents; or pyridazinyl with from 0 to 3 substituents.

57. The compound of claim 56, where X is C$_{1-8}$ alkyl.

58. The compound of claim 56, where at least one Y is halogen.

59. The compound of claim 2, which has one of the following formulae:

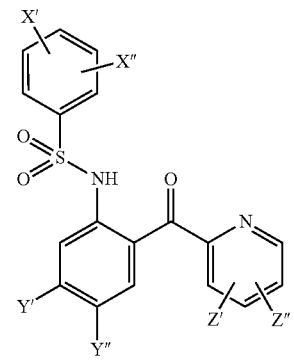

IIa

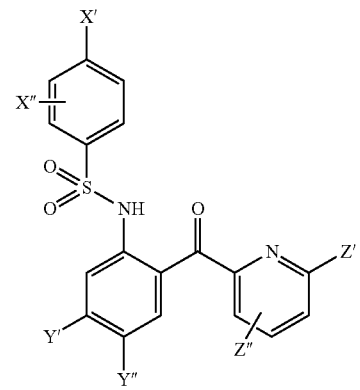

IIb

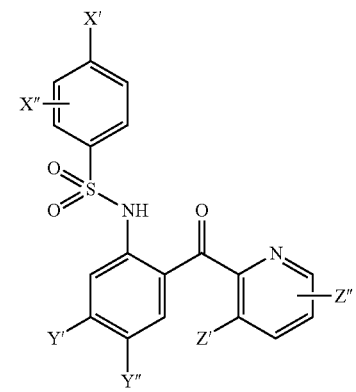

IIc

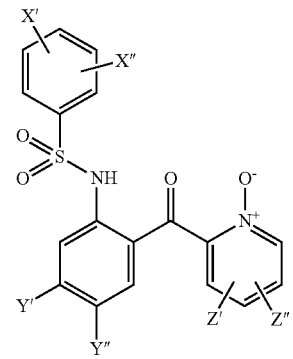

IId

IIe
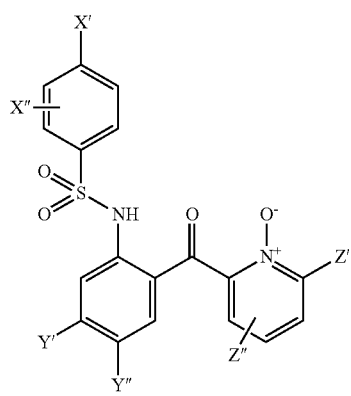
IIf
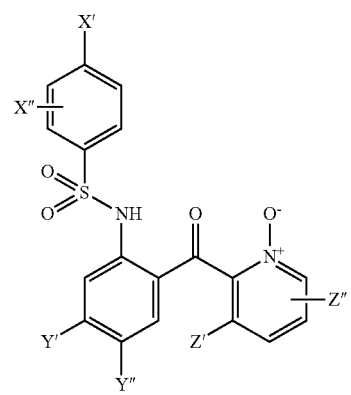
IIIa
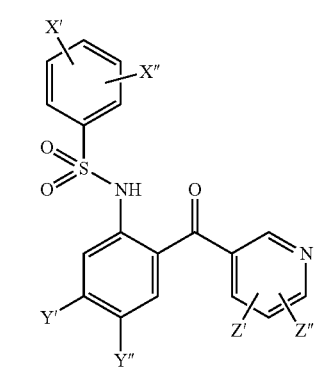
IIIb
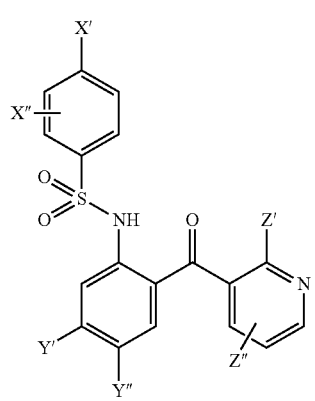
IIIc
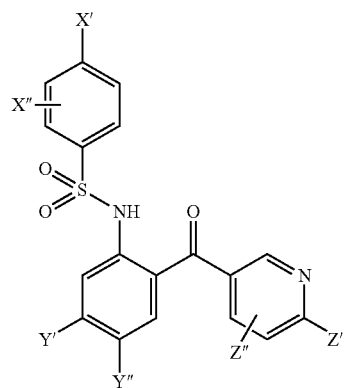
IIId
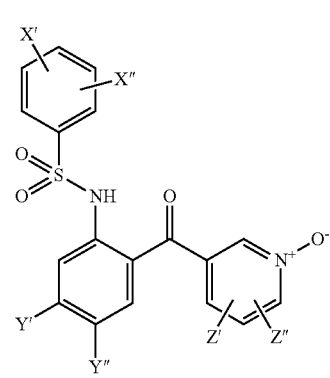
IIIe
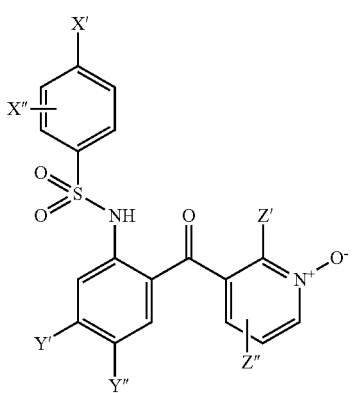
IIIf
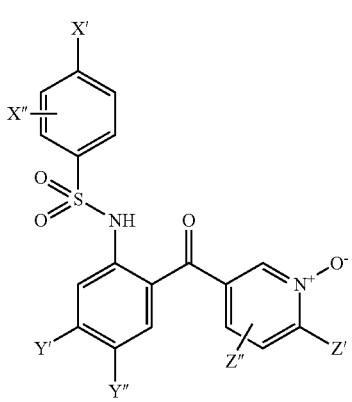

-continued
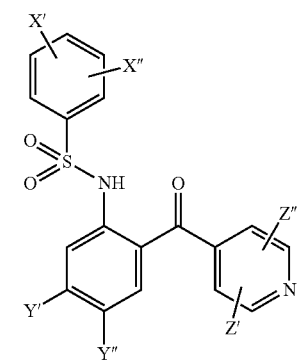
IVa
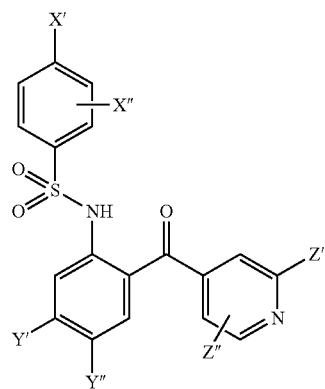
IVb
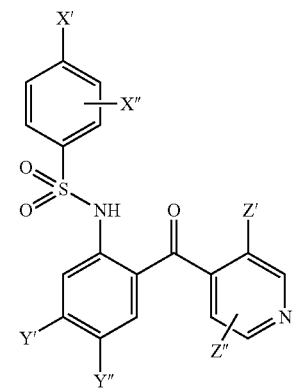
IVc
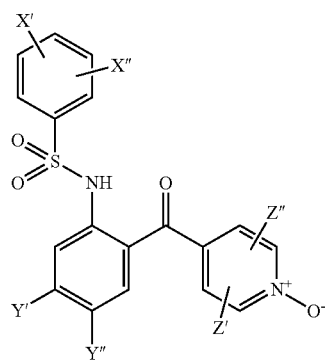
IVd
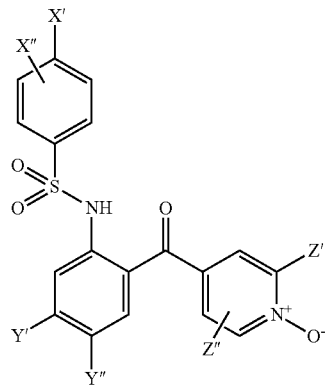
IVe
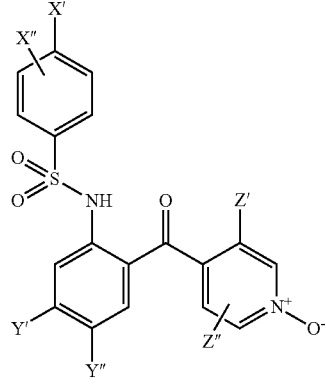
IVf
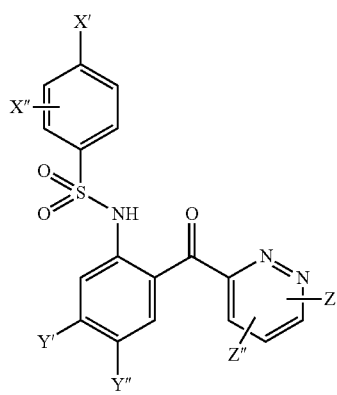
V
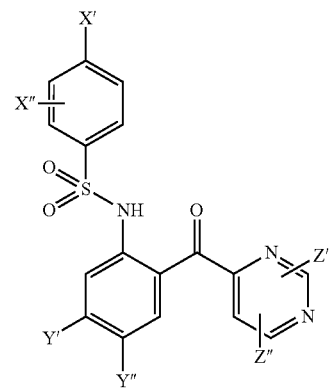
VI -continued

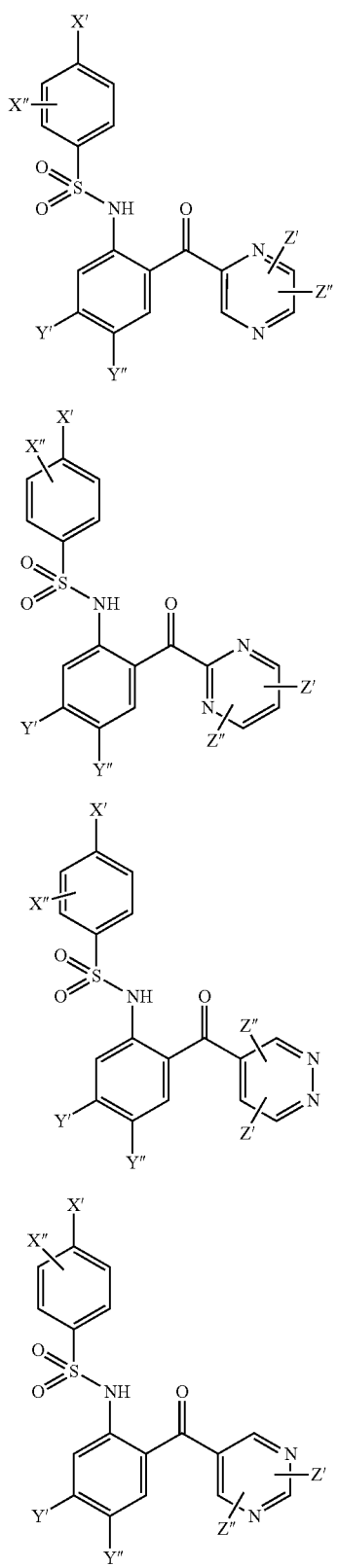

where X' and X" are each independently selected from the group consisting of hydrogen, halogen, —CN, —NO₂, —OH, —C(O)R¹, —CO₂R¹, —O(CO)R¹, —C(O) NR¹R², —OC(O)NR¹R², —SR¹, —SOR¹, —SO₂R¹, —SO₂NR¹R², —NR¹R², —NR¹C(O)R², —NR¹C (O)₂R², —NR¹SO₂R², —NR¹(CO)NR²R³, unsubstituted or substituted $C_{1-8}$ alkyl, unsubstituted or substituted $C_{1-8}$ haloalkyl, unsubstituted or substituted $C_{2-8}$ alkenyl, unsubstituted or substituted $C_{2-8}$ alkynyl, unsubstituted or substituted $C_{3-8}$ cycloalkyl, unsubstituted or substituted $C_{6-10}$ aryl, unsubstituted or substituted 5- to 10-membered heteroaryl, and unsubstituted or substituted 3- to 10-membered heterocyclyl, with the proviso that X' and X" cannot both be hydrogen simultaneously;

R¹, R² and R³ are each independently selected from the group consisting of hydrogen, $C_{1-6}$ haloalkyl, $C_{1-6}$ alkyl, $C_{3-6}$ cycloalkyl, $C_{2-6}$ alkenyl, $C_{2-6}$ alkynyl, $C_{6-10}$ aryl, 5- to 10-membered heteroaryl, aryl-$C_{1-4}$ alkyl, aryl-$C_{1-4}$ alkyl, and aryloxy-$C_{1-4}$ alkyl; or two of R¹, R² and R³ together with the atom(s) to which they are attached, may form a 5-, 6- or 7-membered ring;

Y' and Y" are each independently selected from the group consisting of hydrogen, halogen, —CN, —NO₂, —OH, —OR⁴, —C(O)R⁴, —CO₂R⁴, —SR⁴, —SOR⁴, —SO₂R⁴, unsubstituted or substituted $C_{1-4}$ alkyl, and unsubstituted or substituted $C_{1-4}$ haloalkyl, with the proviso that Y' and Y" cannot both be hydrogen simultaneously;

R⁴ is selected from the group consisting of hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, and unsubstituted or substituted $C_{2-6}$ alkynyl;

Z' and Z" are each independently selected from the group consisting of hydrogen, halogen, unsubstituted or substituted $C_{1-8}$ alkyl, unsubstituted or substituted $C_{3-8}$ cycloalkyl, unsubstituted or substituted $C_{2-8}$ alkenyl, unsubstituted or substituted $C_{2-8}$ alkynyl, unsubstituted or substituted $C_{1-8}$ alkoxy, =O, —CN, —NO₂, —OH, —OR⁷, —OC(O)R⁷, —CO₂R⁷, —C(O)R⁷, —CONR⁷R⁸, —OC(O)NR⁷R⁸, —NR⁷C(O)R⁸, —NR⁷C(O)NR⁸R⁹, —NR⁷R⁸, —NR⁷CO₂R⁸, —SR⁷, —SOR⁷, —SO₂R⁷, —SO₂NR⁷R⁸, —NR⁷SO₂R⁸, unsubstituted or substituted $C_{6-10}$ aryl, unsubstituted or substituted 5- or 6-membered heteroaryl and unsubstituted or substituted 3- to 7-membered heterocyclyl; and where R⁷, R⁸ and R⁹ are each independently hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted phenyl, unsubstituted or substituted heteroaryl, unsubstituted or substituted aryl-$C_{1-4}$ alkyl, and unsubstituted or substituted aryloxy-$C_{1-4}$ alkyl; or where any two of R⁷, R⁸ and R⁹ together with the atom(s) to which they are attached, may form a 5-, 6- or 7-membered ring.

60. The compound of claim 59, where X' and X" are each independently selected from the group consisting of hydrogen, —NO₂, —OR¹, —C(O)R¹, —SO₂R¹, —NR¹R², unsubstituted or substituted $C_{1-8}$ alkyl, unsubstituted or substituted $C_{1-8}$ haloalkyl, unsubstituted or substituted $C_{3-8}$ cycloalkyl, unsubstituted or substituted $C_{2-8}$ alkenyl, unsubstituted or substituted phenyl, unsubstituted or substituted 5- or 6-membered heteroaryl, unsubstituted or substituted 5- or 6-membered heterocyclyl, with the proviso that X' and X" cannot both be hydrogen simultaneously.

61. The compound of claim 59, where X' and X" are each independently selected from the group consisting of hydrogen, —$CF_3$, —CH=$CH_2$, isoamyl, phenylacetylene, t-butyl, ethyl (Et), i-propyl ($^i$Pr), —C($CH_3$)$_2$$CH_2$$CH_3$, hydroxybutyl, —C($CH_3$)$_2$$CH_2$$CH_2$OH, —$CH_2$$CH_2$$CO_2$Me, —$OCF_3$, —OMe, —O—$^i$Pr, —C(O)Me, —$SO_2$Me, phenyl (Ph), —OEt, pyrazole, oxazole, and morpholinyl, with the proviso that X' and X" cannot both be hydrogen simultaneously.

62. The compound of claim 59, where Y' and Y" are each independently hydrogen or halogen, with the proviso that one or both are halogen.

63. The compound of claim 62, where Y' is hydrogen and Y" is chloro; Y' and Y" are both fluoro; Y' is hydrogen and Y" is fluoro; or Y' is hydrogen and Y" is bromo.

64. The compound of claim 59, where at least one of Y' or Y" is a halogen atom and is para to the sulfonamide bond in formula (I).

65. The compound of claim 59, where Z' and Z" are each independently selected from the group consisting of hydrogen, halogen, unsubstituted or substituted $C_{1-8}$ alkyl, unsubstituted or substituted $C_{1-8}$ cycloalkyl, —CN, —OH, —C(O)$R^7$, —$CO_2$$R^7$, —OC(O)$R^7$, —CON$R^7$$R^8$, —$NR^7$$R^8$, —$NR^7$$CO_2$$R^8$, —$SR^7$, —$SOR^7$, —$SO_2$$R^7$, —$NR^7$$SO_2$$R^8$, unsubstituted or substituted $C_{6-10}$ aryl, and unsubstituted or substituted 5- or 6-membered heteroaryl, unsubstituted or substituted 3- to 7-membered heterocycyl.

66. The compound of claim 59, where Z' and Z" are each independently hydrogen, halogen, —CN, —$NR^7$$R^8$, —$SR^7$, —$SOR^7$, and —$SO_2$$R^7$, unsubstituted or substituted $C_{1-6}$ alkoxyl, unsubstituted or substituted $C_{1-6}$ alkyl, unsubstituted or substituted phenyl, or unsubstituted or substituted 5- or 6-membered heterocyclyl.

67. The compound of claim 60, where Y' and Y" are each independently hydrogen or halogen, with the proviso that one or both are halogen.

68. The compound of claim 60, where Z' and Z" are each independently selected from the group consisting of hydrogen, halogen, unsubstituted or substituted $C_{1-8}$ alkyl, unsubstituted or substituted $C_{1-8}$ cycloalkyl, —CN, —OH, —$OR^7$, —C(O)$R^7$, —$CO_2$$R^7$, —OC(O)$R^7$, —CON$R^7$$R^8$, —$NR^7$$R^8$, —$NR^7$$CO_2$$R^8$, —$SR^7$, —$SOR^7$, —$SO_2$$R^7$, —$NR^7$$SO_2$$R^8$, unsubstituted or substituted $C_{6-10}$ aryl, and unsubstituted or substituted 5- or 6-membered heteroaryl, unsubstituted or substituted 3- to 7-membered heterocycyl.

69. The compound of claim 62, where Z' and Z" are each independently selected from the group consisting of hydrogen, halogen, unsubstituted or substituted $C_{1-8}$ alkyl, unsubstituted or substituted $C_{1-8}$ cycloalkyl, —CN, —OH, —$OR^7$, —C(O)$R^7$, —$CO_2$$R^7$, —OC(O)$R^7$, —CON$R^7$$R^8$, —$NR^7$$R^8$, —$NR^7$$CO_2$$R^8$, —$SR^7$, —$SOR^7$, —$SO_2$$R^7$, —$NR^7$$SO_2$$R^8$, unsubstituted or substituted $C_{6-10}$ aryl, and unsubstituted or substituted 5- or 6-membered heteroaryl, unsubstituted or substituted 3- to 7-membered heterocycyl.

70. The compound of claim 67, where Z' and Z" are each independently selected from the group consisting of hydrogen, halogen, unsubstituted or substituted $C_{1-8}$ alkyl, unsubstituted or substituted $C_{1-8}$ cycloalkyl, —CN, —OH, —$OR^7$, —C(O)$R^7$, —$CO_2$$R^7$, —OC(O)$R^7$, —CON$R^7$$R^8$, —$NR^7$$R^8$, —$NR^7$$CO_2$$R^8$, —$SR^7$, —$SOR^7$, —$SO_2$$R^7$, —$NR^7$$SO_2$$R^8$, unsubstituted or substituted $C_{6-10}$ aryl, and unsubstituted or substituted 5- or 6-membered heteroaryl, unsubstituted or substituted 3- to 7-membered heterocycyl.

71. A composition comprising a pharmaceutically acceptable carrier and a compound of claim 2.

72. A method for treating inflammatory bowel disease comprising administering to a subject a safe and effective amount of the compound of claim 2.

73. A method for treating condition or disease is selected from the group consisting of an allergic disease, psoriasis, atopic dermatitis, asthma, fibrotic diseases and graft rejection, comprising administering to a subject a safe and effective amount of the compound of claim 2.

74. A method for treating Celiac disease or rheumatoid arthritis, comprising administering to a subject a safe and effective amount of the compound of claim 2.

75. The method of claim 72, 73 or 74, where the administering is oral, parenteral, rectal, transdermal, sublingual, nasal or topical.

76. The method of claim 72, 73 or 74, where the compound is administered in combination with an anti-inflammatory or analgesic agent.

77. A method of modulating CCR9 function in a cell, comprising contacting the cell in vitro with a CCR9 modulating amount of the compound of claim 2.

78. The method of claim 72, 73 or 74, further comprising administering an anti-inflammatory or analgesic agent.

\* \* \* \* \*